(12) United States Patent
Zhao et al.

(10) Patent No.: US 12,220,435 B2
(45) Date of Patent: Feb. 11, 2025

(54) SWINE ORIGIN PROBIOTICS THAT PROMOTE HEALTH AND GROWTH PERFORMANCE IN PIGS

(71) Applicant: THE BOARD OF TRUSTEES OF THE UNIVERSITY OF ARKANSAS, Little Rock, AR (US)

(72) Inventors: Jiangchao Zhao, Fayetteville, AR (US); Xiaofan Wang, Fayetteville, AR (US); Tsungcheng Tsai, Fayetteville, AR (US); Charles V. Maxwell, Springdale, AR (US)

(73) Assignee: THE BOARD OF TRUSTEES OF THE UNIVERSITY OF ARKANSAS, Little Rock, AR (US)

(*) Notice: Subject to any disclaimer, the term of this patent is extended or adjusted under 35 U.S.C. 154(b) by 0 days.

(21) Appl. No.: 17/344,372

(22) Filed: Jun. 10, 2021

(65) Prior Publication Data

US 2021/0386801 A1 Dec. 16, 2021

Related U.S. Application Data

(60) Provisional application No. 63/037,435, filed on Jun. 10, 2020.

(51) Int. Cl.

| A61K 35/747 | (2015.01) |
| A23K 10/16 | (2016.01) |
| A23K 10/18 | (2016.01) |
| A23K 50/30 | (2016.01) |
| A23K 50/60 | (2016.01) |
| A61K 9/00 | (2006.01) |
| A61K 9/19 | (2006.01) |
| A61K 35/741 | (2015.01) |
| A61K 35/744 | (2015.01) |

(52) U.S. Cl.
CPC ............ *A61K 35/747* (2013.01); *A23K 10/16* (2016.05); *A23K 10/18* (2016.05); *A23K 50/30* (2016.05); *A23K 50/60* (2016.05); *A61K 9/19* (2013.01); *A61K 35/741* (2013.01); *A61K 35/744* (2013.01); *A61K 9/0053* (2013.01)

(58) Field of Classification Search
CPC .............................. A23K 50/30; A61K 35/744
See application file for complete search history.

(56) References Cited

U.S. PATENT DOCUMENTS

| 11,122,828 B2 | 9/2021 | Jayamani et al. |
| 2013/0064928 A1 | 3/2013 | Iino et al. |
| 2014/0147425 A1 | 5/2014 | Henn et al. |

FOREIGN PATENT DOCUMENTS

| WO | WO-2016086209 A1 * | 6/2016 | ......... A61K 31/7004 |

OTHER PUBLICATIONS

Yang et al., "Effect of probiotic containing Lactobacillus plantarum on growth performance, nutrient digestibility, and fecal microbiota in weaning pigs", Canadian Journal of Animal Science, vol. 100(1), p. 205-209. (Year: 2020).*
McCartney, A.L., "Application of molecular biological methods for studying probiotics and the gut flora", British Journal of Nutrition, vol. 88, Suppl. 1, p. S29-S37. (Year: 2002).*
Edgar, "Updating the 97% identity threshold for 16S ribosomal RNA OTUs", Bioinformatics, vol. 34(14), p. 2371-2375. (Year: 2018).*
Fouhse, J.M., et al., "The role of gut microbiota in the health and disease of pigs", Animal Frontiers, vol. 6, Issue 3, pp. 30-36. (Year: 2016).*
Turck, et al., Age and diet affect the composition of porcine colonic mucins. Pediatric Research 1993, 33:564.
Wang, et al., (2019). Longitudinal investigation of the swine gut microbiome from birth to market reveals stage and growth performance associated bacteria. Microbiome, 7(1), 109. doi:10.1186/s40168-019-0721-7.
Wilczyńska, et al., Meconium microbiome as a new source of information about long-term health and disease: questions and answers. The Journal of Maternal-Fetal & Neonatal Medicine 2019, 32:681-686.
Wu, et al., Linking long-term dietary patterns with gut microbial enterotypes. Science 2011, 334:105-108.
Xiao, et al., A reference gene catalogue of the pig gut microbiome. Nat Microbiol 2016:16161.
Xiao, et al., Comparative biogeography of the gut microbiome between Jinhua and Landrace pigs. Sci Rep 2018, 8:5985.
Yang, et al., Gut Microbiota Is a Major Contributor to Adiposity in Pigs. Frontiers in Microbiology 2018, 9.
Amir, et al., Deblur rapidly resolves single-nucleotide community sequence patterns. mSystems 2017, 2: e00191-00116.
Anderson, Permutational multivariate analysis of variance (Permanova). In Wiley StatsRef: Statistics Reference Online. 2017: 1-15.
Bäckhed, et al., Dynamics and stabilization of the human gut microbiome during the first year of life. Cell host microbe 2015, 17:690-703.
Balasubramanian, et al., (2016). Effects of supplementing growing-finishing pig diets with *Bacillus* spp. probiotic on growth performance and meat-carcass grade qualitytraits. Revista Brasileira de Zootecnia, 45, 93-100.

(Continued)

*Primary Examiner* — Michelle F. Paguio Frising
*Assistant Examiner* — Grant C Currens
(74) *Attorney, Agent, or Firm* — Quarles & Brady, LLP

(57) ABSTRACT

The present invention provides probiotic compositions comprising isolated bacterial strains, referred to herein as LactX, StrepX1 and StrepX3. Methods of using the compositions to increase growth rate in pigs and enhance pig production are also provided.

4 Claims, 41 Drawing Sheets
(22 of 41 Drawing Sheet(s) Filed in Color)
Specification includes a Sequence Listing.

(56) References Cited

OTHER PUBLICATIONS

Bian, et al., Age, introduction of solid feed and weaning are more important determinants of gut bacterial succession in piglets than breed and nursing mother as revealed by a reciprocal cross-fostering model. Environmental Microbiology 2016, 18:1566-1577.

Breiman, Random forests. J Machine learning 2001, 45:5-32.

Brown, et al., The influence of different management systems and age on intestinal morphology, immune cell numbers and mucin production from goblet cells in post-weaning pigs. Veterinary immunology immunopathology 2006, 111:187-198.

Burnett, et al., (2010). A note on the effect of Probioticum feed additive on the live-weight gain, feed conversion and carcass quality of bacon pigs. Animal Science, 25(1), 95-98. doi: 10.1017/S0003356100039088.

Chen, et al., Effects of dietary Clostridium butyricum supplementation on growth performance, intestinal development, and immune response of weaned piglets challenged with lipopolysaccharide. Journal of animal science biotechnology 2018, 9:62.

Chen, et al., The maturing development of gut microbiota in commercial piglets during the weaning transition. Front Microbiol 2017, 8:1688.

Chen, et al., Fiber-utilizing capacity varies in Prevotella-versus Bacteroides-dominated gut microbiota. Scientific reports 2017, 7:2594.

Chen, et al., Lactation stage-dependency of the sow milk microbiota. Frontiers in microbiology 2018, 9:945.

Chong, et al., Factors affecting gastrointestinal microbiome development in neonates. Nutrients 2018, 10:274.

Curley, et al., The meaning of weaning: influence of the weaning period on behavioral development in mice. Developmental neuroscience 2009, 31:318-331.

De Filippis, et al., Distinct genetic and functional traits of human intestinal prevotella copri strains are associated with different habitual diets. Cell Host Microbe 2019, 25:444-453 e443.

De Rodas, et al., Microbiome profiling of commercial pigs from farrow to finish. Anim Sci 2018, 96:1778-1794.

Dimitriu, et al., Temporal stability of the mouse gut microbiota in relation to innate and adaptive immunity. Environmental microbiology reports 2013, 5:200-210.

El Kaoutari, et al., The abundance and variety of carbohydrate-active enzymes in the human gut microbiota. Nature reviews Microbiology 2013, 11:497.

Etherton, et al., Effects of cell size and animal age on glucose metabolism in pig adipose tissue. Journal of lipid research 1981, 22:72-80.

Everaert, et al., A review on early gut maturation and colonization in pigs, including biological and dietary factors affecting gut homeostasis. Animal Feed Science Technology 2017, 233:89-103.

Frese, et al., Diet shapes the gut microbiome of pigs during nursing and weaning. Microbiome 2015, 3:28-28.

Girvan, et al., Community structure in social and biological networks. Proc Natl Acad Sci U S A 2002, 99:7821-7826.

Grosicki, et al., Gut microbiota contribute to age-related changes in skeletal muscle size, composition, and function: biological basis for a gut-muscle axis. Calcified tissue international 2018, 102:1-10.

Han, et al., Tracing of the fecal microbiota of commercial pigs at five growth stages from birth to shipment. Scientific reports 2018, 8:6012.

He, et al., Effects of oat bran on nutrient digestibility, intestinal microbiota, and inflammatory responses in the hindgut of growing Pigs. International Journal of Molecular Sciences 2018, 19.

Houghteling, et al., Why is initial bacterial colonization of the intestine important to the infant's and child's health? Journal of pediatric gastroenterology nutrition 2015, 60:294.

Kellermayer, et al., Colonic mucosal DNA methylation, immune response, and microbiome patterns in Toll-like receptor 2-knockout mice. The FASEB Journal 2011, 25:1449-1460.

Kim, et al., Nutrition and pathology of weaner pigs: nutritional strategies to support barrier function in the gastrointestinal tract. Animal feed science technology 2012, 173:3-16.

Kong, et al., Identification of gut microbiome signatures associated with longevity provides a promising modulation target for healthy aging. Gut microbes 2018, 10:1-6.

Kozich, et al., Development of a dual-index sequencing strategy and curation pipeline for analyzing amplicon sequence data on the MiSeq Illumina sequencing platform. Applied environmental microbiology 2013, 79:AEM. 01043-01013.

Lallès, et al., Gut function and dysfunction in young pigs: physiology. Animal Research 2004, 53:301-316.

Liu, et al., (2018). Non-antibiotic feed additives in diets for pigs: A review. Animal Nutrition, 4(2), 113-125. doi:https://doi.org/10.1016/j.aninu.2018.01.007.

Lu, et al., Host contributes to longitudinal diversity of fecal microbiota in swine selected for lean growth. Microbiome 2018, 6:4.

Mach, et al., Early-life establishment of the swine gut microbiome and impact on host phenotypes. Environmental microbiology reports 2015, 7:554-569.

Markowiak, et al., (2018). The role of probiotics, prebiotics and synbiotics in animal nutrition. Gut Pathogens, 10(1), 21. doi:10.1186/s13099-018-0250-0.

McCormack, et al., Exploring a Possible Link between the Intestinal Microbiota and Feed Efficiency in Pigs. Applied and Environmental Microbiology 2017, 83.

Meng, et al., Influence of probiotics in different energy and nutrient density diets on growth performance, nutrient digestibility, meat quality, and blood characteristics in growing-finishing pigs. Animal science 2010, 88:3320-3326.

Moeser, et al., Weaning stress and gastrointestinal barrier development: Implications for lifelong gut health in pigs. Animal Nutrition 2017, 3:313-321.

Pajarillo, et al., Assessment of fecal bacterial diversity among healthy piglets during the weaning transition. The Journal of general applied microbiology 2014, 60:140-146.

Pluske, et al., Gastrointestinal tract (gut) health in the young pig. Animal Nutrition 2018, 4:187-196.

Rachagani, et al., Mucin (Muc) expression during pancreatic cancer progression in spontaneous mouse model: potential implications for diagnosis and therapy. Journal of hematology oncology 2012, 5:68.

Ramayo-Caldas, et al., Phylogenetic network analysis applied to pig gut microbiota identifies an ecosystem structure linked with growth traits. Isme Journal 2016, 10:2973-2977.

Rodriguez, et al., The composition of the gut microbiota throughout life, with an emphasis on early life. Microbial ecology in health disease 2015, 26:26050.

Roos, et al., *Lactobacillus mucosae* sp. nov., a new species with in vitro mucus-binding activity isolated from pig intestine. Int J Syst Evol Microbiol 2000, 50 Pt 1:251-258.

Ross, et al., (2012). Fatty Acid Profile of Pig Meat after Probiotic Administration. Journal of Agricultural and Food Chemistry, 60(23), 5974-5978. doi:10.1021/jf205360h.

Rybarczyk, et al., (2020). Effect of EM® probiotic on gut microbiota, growth performance, carcass and meat quality of pigs. Livestock Science, 241, 104206. doi:https://doi.org/10.1016/j.livsci.2020.104206.

Segata, et al., Metagenomic biomarker discovery and explanation. Genome Biol 2011, 12:R60.

Shetty, et al., Comparative genome analysis of *Megasphaera* sp. reveals niche specialization and its potential role in the human gut. PLOS one 2013, 8:e79353.

Tsai, et al., Isolated rearing at lactation increases gut microbial diversity and post-weaning performance in pigs. Front Microbiol 2018, 9:2889.

Genbank KX648726.1. Lactobacillus plantarum strain 1.2.11 16S ribosomal RNA gene, partial sequenc [online] Feb. 20, 2017 [retrieved Oct. 21, 2021]. Available on the internet: <URL: https://.ncbi.nlm.nih.gov/nuccore/KS648726.1>.

International Search Report and Written Opinion issued in corresponding International Patent Application No. PCT/US2021/036804, mailing date Dec. 7, 2021.

Li, Y. et al., Life-long dynamics of the swine gut microbiome and their implications in probiotics development and food safety. Gut Microbes. Nov. 1, 2020;11(6):1824-1832.

(56) References Cited

OTHER PUBLICATIONS

Vera-Mejía et al., "Lactobacillus plantarum strains with probiotic potentials isolated from Creole pigs," Revista de Salud Animal, May-Aug. 2020, 42(2): 1-9.

* cited by examiner

Fig. 8

Lactation % 25.9

| Feature | |
|---|---|
| F77 | ○ (≈27) |
| F323 | ○ (≈22) |
| F363 | ○ (≈20) |
| F190 | ○ |
| F182 | ○ |
| F450 | ○ |
| F264 | ○ |
| F876 | ○ |
| F360 | ○ |
| F295 | ○ |
| F162 | ○ |
| F694 | ○ |
| F35 | ○ |
| F1 | ○ |
| F270 | ○ |
| F298 | ○ |
| F168 | ○ |
| F22 | ○ |
| F2 | ○ |
| F130 | ○ |
| F253 | ○ |
| F340 | ○ |
| F249 | ○ |
| F413 | ○ |
| F446 | ○ |
| F346 | ○ |
| F166 | ○ |
| F257 | ○ |
| F92 | ○ |
| F317 | ○ |
| F224 | ○ |
| F502 | ○ |
| F138 | ○ |
| F714 | ○ |
| F65 | ○ |
| F141 | ○ |
| F21 | ○ |
| F123 | ○ |
| F172 | ○ |
| F233 | ○ |
| F68 | ○ |
| F408 | ○ |
| F157 | ○ |
| F216 | ○ |
| F486 | ○ |
| F356 | ○ |
| F421 | ○ |
| F235 | ○ |
| F53 | ○ |
| F247 | ○ |

5  15  25
%IncMSE

Nursery % 69.21

| Feature | |
|---|---|
| F234 | ○ |
| F17 | ○ |
| F47 | ○ |
| F222 | ○ |
| F202 | ○ |
| F347 | ○ |
| F1 | ○ |
| F604 | ○ |
| F2 | ○ |
| F205 | ○ |
| F195 | ○ |
| F7 | ○ |
| F104 | ○ |
| F223 | ○ |
| F379 | ○ |
| F221 | ○ |
| F319 | ○ |
| F439 | ○ |
| F333 | ○ |
| F233 | ○ |
| F12 | ○ |
| F48 | ○ |
| F545 | ○ |
| F154 | ○ |
| F339 | ○ |
| F36 | ○ |
| F245 | ○ |
| F42 | ○ |
| F180 | ○ |
| F283 | ○ |
| F228 | ○ |
| F348 | ○ |
| F336 | ○ |
| F274 | ○ |
| F242 | ○ |
| F301 | ○ |
| F299 | ○ |
| F35 | ○ |
| F13 | ○ |
| F102 | ○ |
| F287 | ○ |
| F43 | ○ |
| F93 | ○ |
| F362 | ○ |
| F131 | ○ |
| F367 | ○ |
| F454 | ○ |
| F177 | ○ |
| F77 | ○ |
| F268 | ○ |

10  30  50
%IncMSE

Growing % 56.43

| Feature | |
|---|---|
| F4 | ○ |
| F18 | ○ |
| F26 | ○ |
| F27 | ○ |
| F121 | ○ |
| F309 | ○ |
| F22 | ○ |
| F127 | ○ |
| F445 | ○ |
| F100 | ○ |
| F382 | ○ |
| F330 | ○ |
| F13 | ○ |
| F484 | ○ |
| F473 | ○ |
| F395 | ○ |
| F215 | ○ |
| F73 | ○ |
| F505 | ○ |
| F188 | ○ |
| F581 | ○ |
| F40 | ○ |
| F414 | ○ |
| F103 | ○ |
| F381 | ○ |
| F231 | ○ |
| F29 | ○ |
| F338 | ○ |
| F66 | ○ |
| F433 | ○ |
| F19 | ○ |
| F335 | ○ |
| F464 | ○ |
| F446 | ○ |
| F348 | ○ |
| F75 | ○ |
| F196 | ○ |
| F269 | ○ |
| F74 | ○ |
| F431 | ○ |
| F221 | ○ |
| F252 | ○ |
| F68 | ○ |
| F12 | ○ |
| F281 | ○ |
| F33 | ○ |
| F237 | ○ |
| F38 | ○ |
| F118 | ○ |
| F173 | ○ |

10  30  50
%IncMSE

Fig. 12
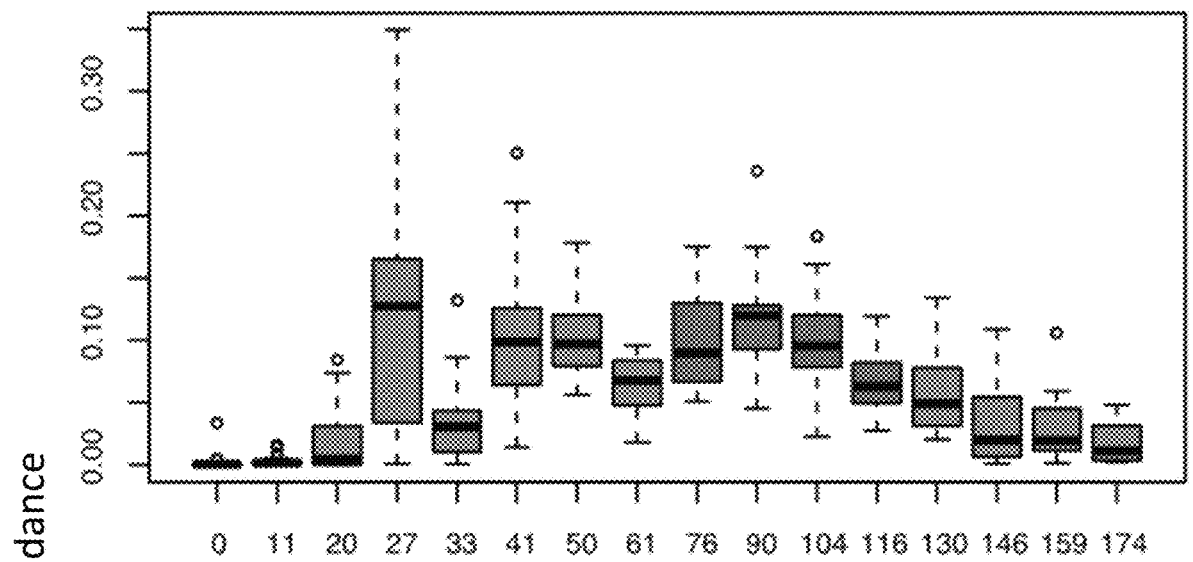
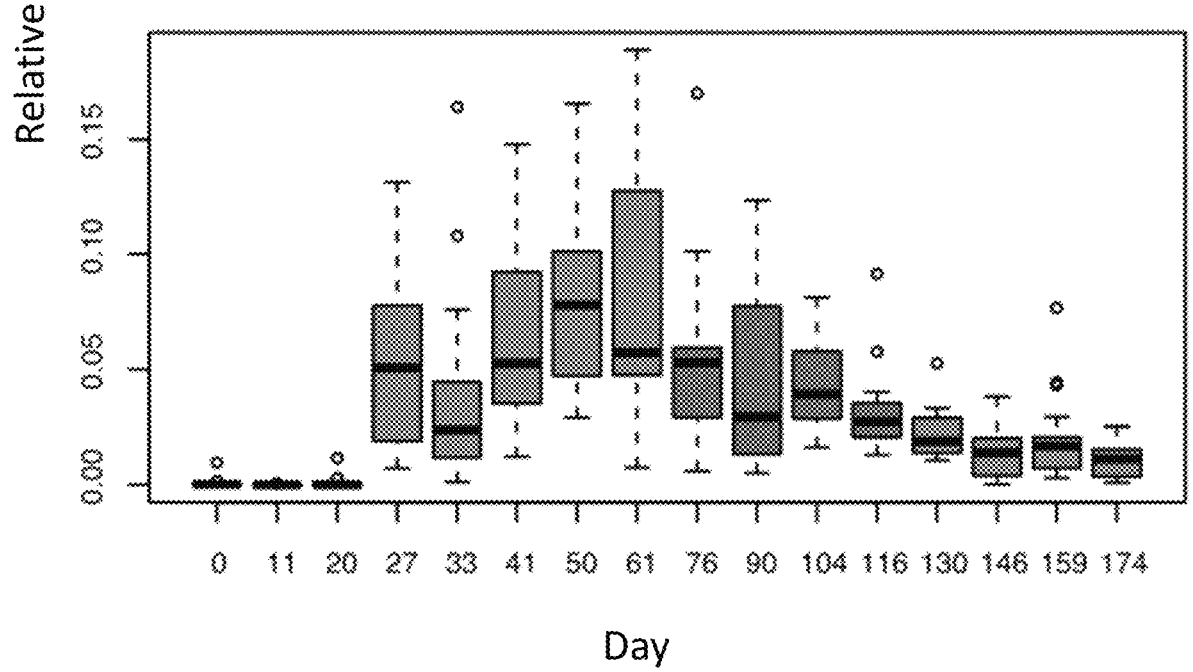
Day

Fig. 12 (continued)
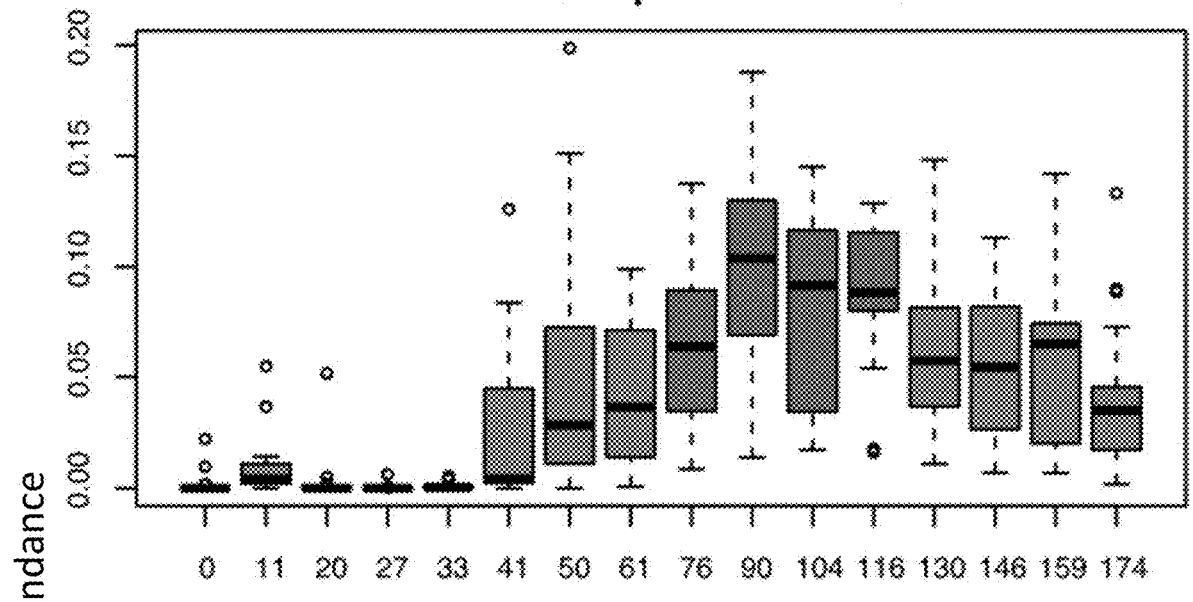
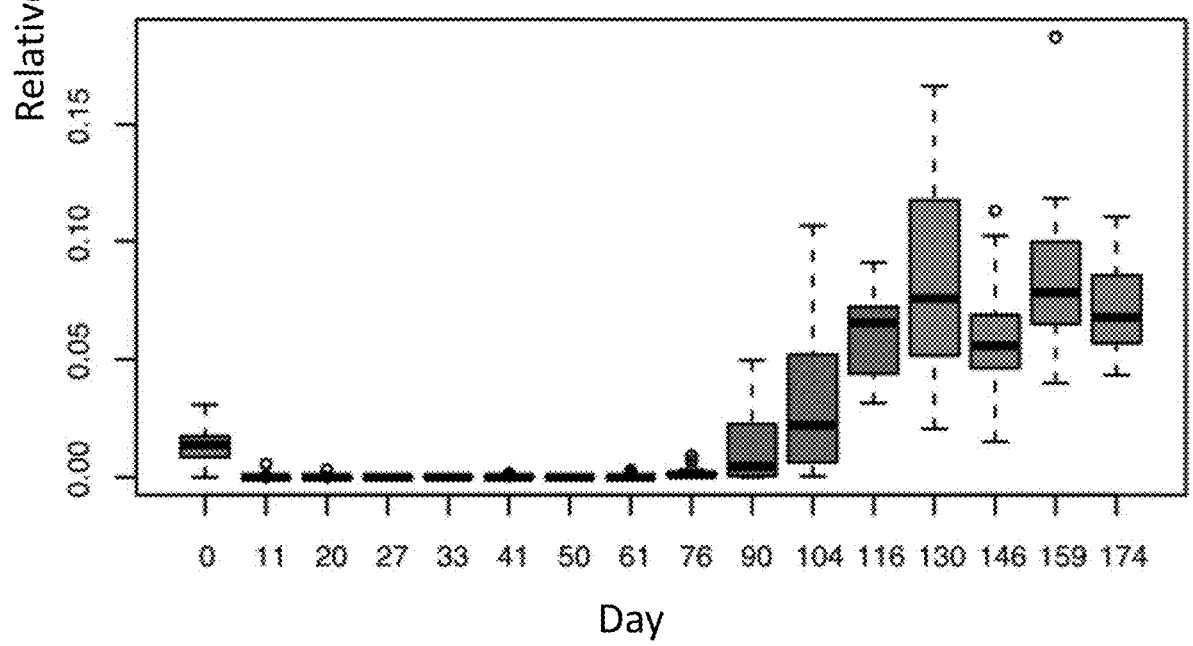
Day

Fig. 12 (continued)
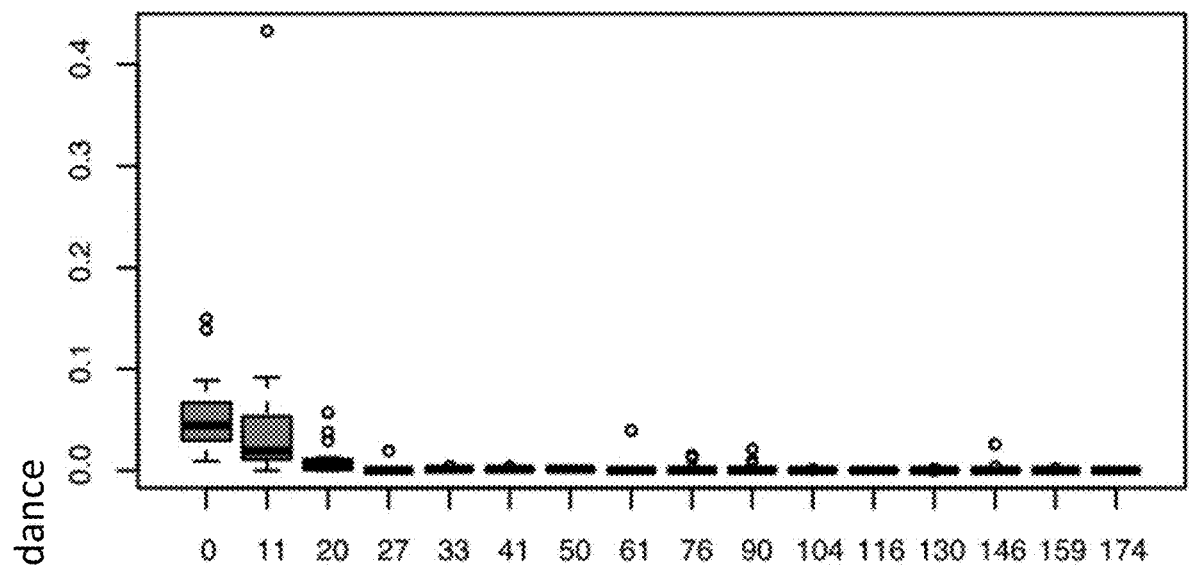
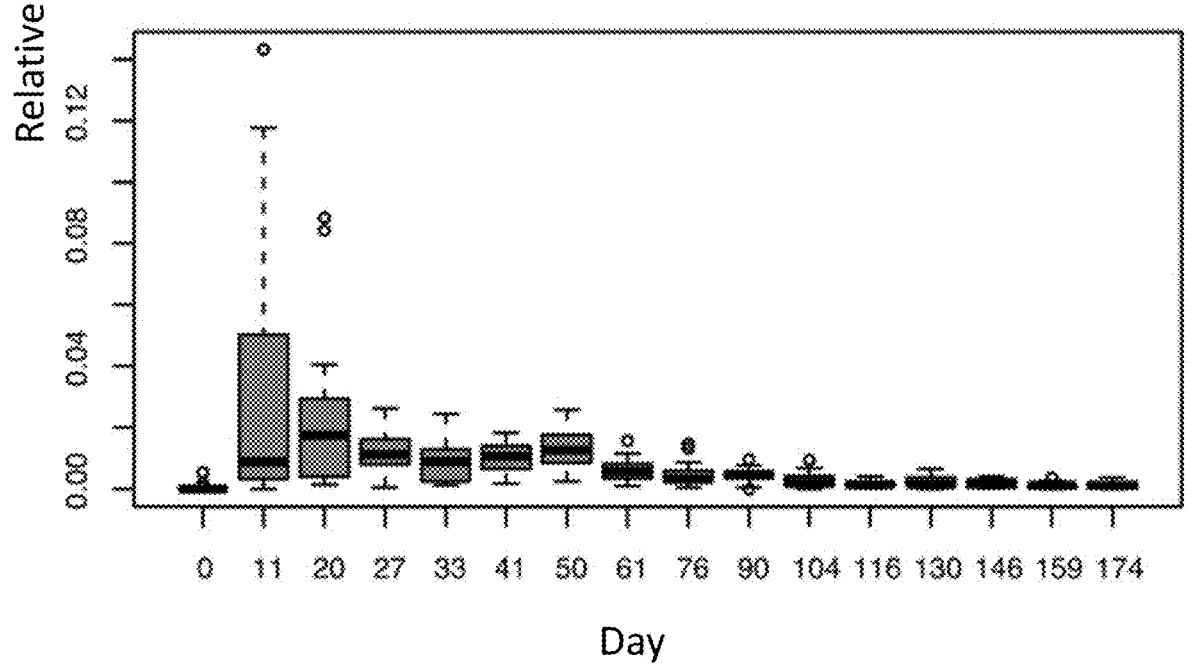

Fig. 12 (continued)
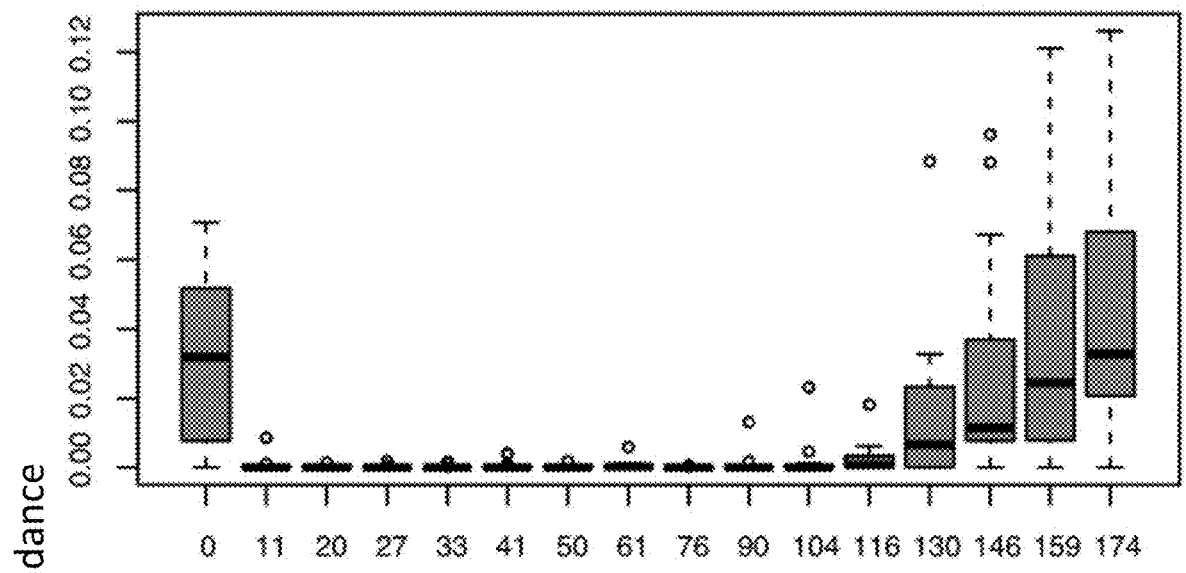
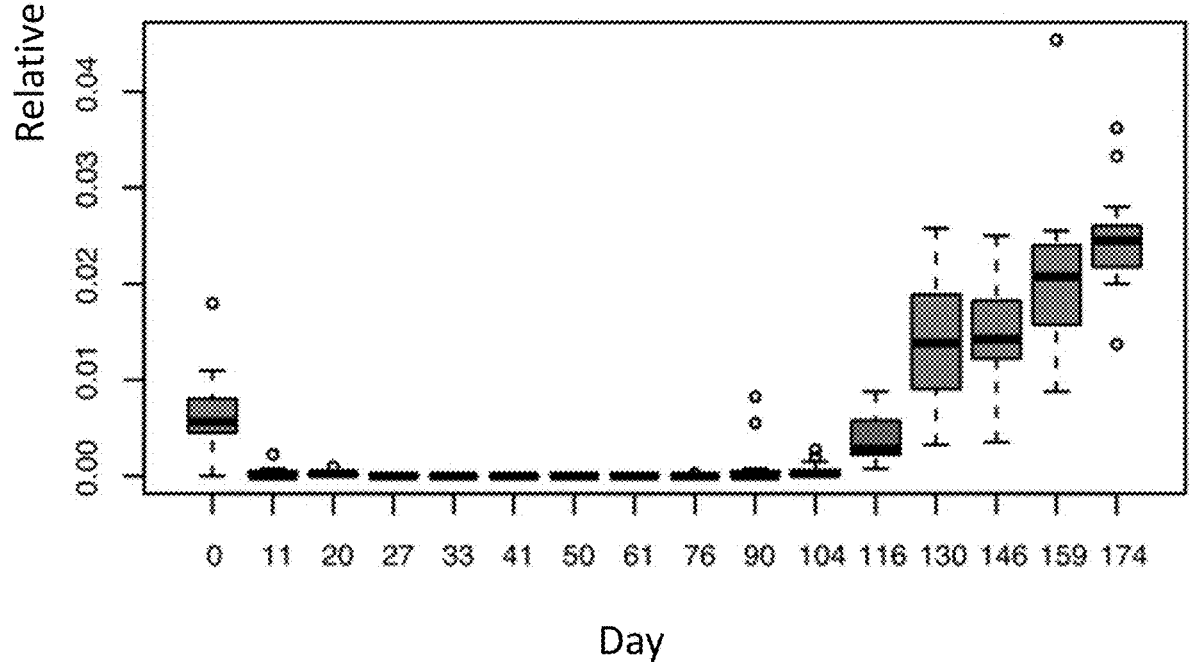
Day

Fig. 13
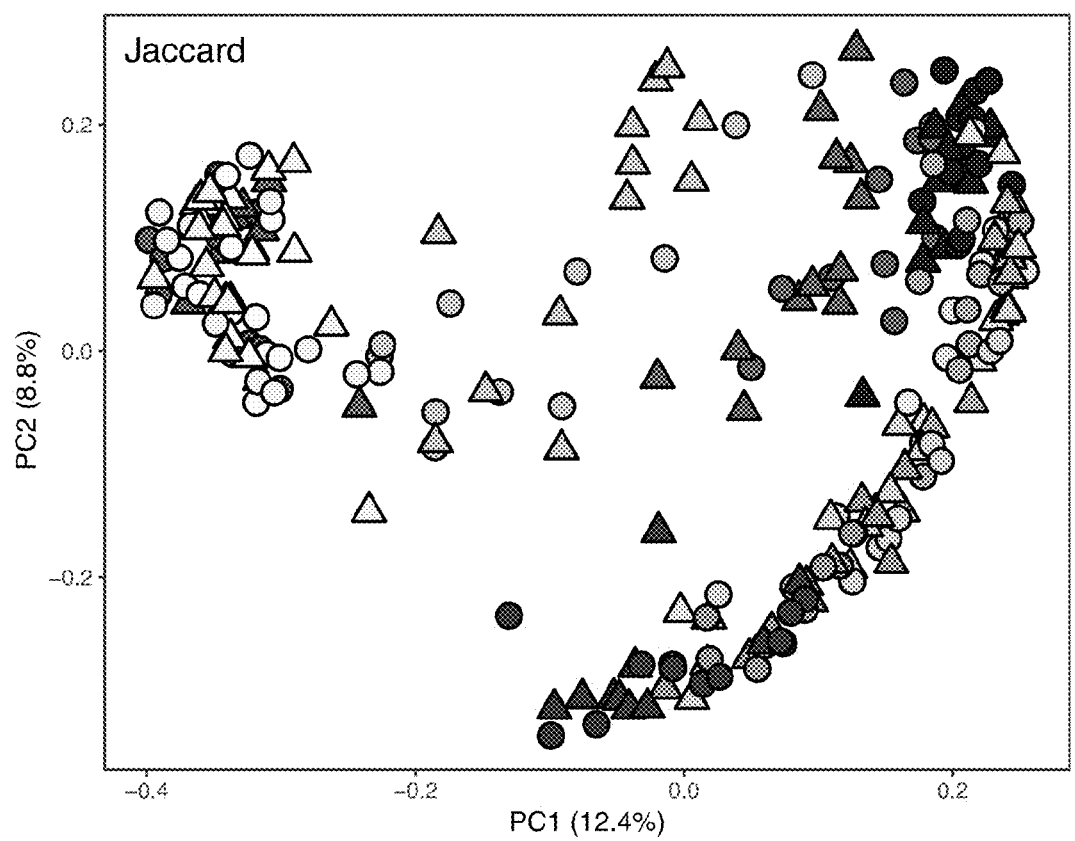
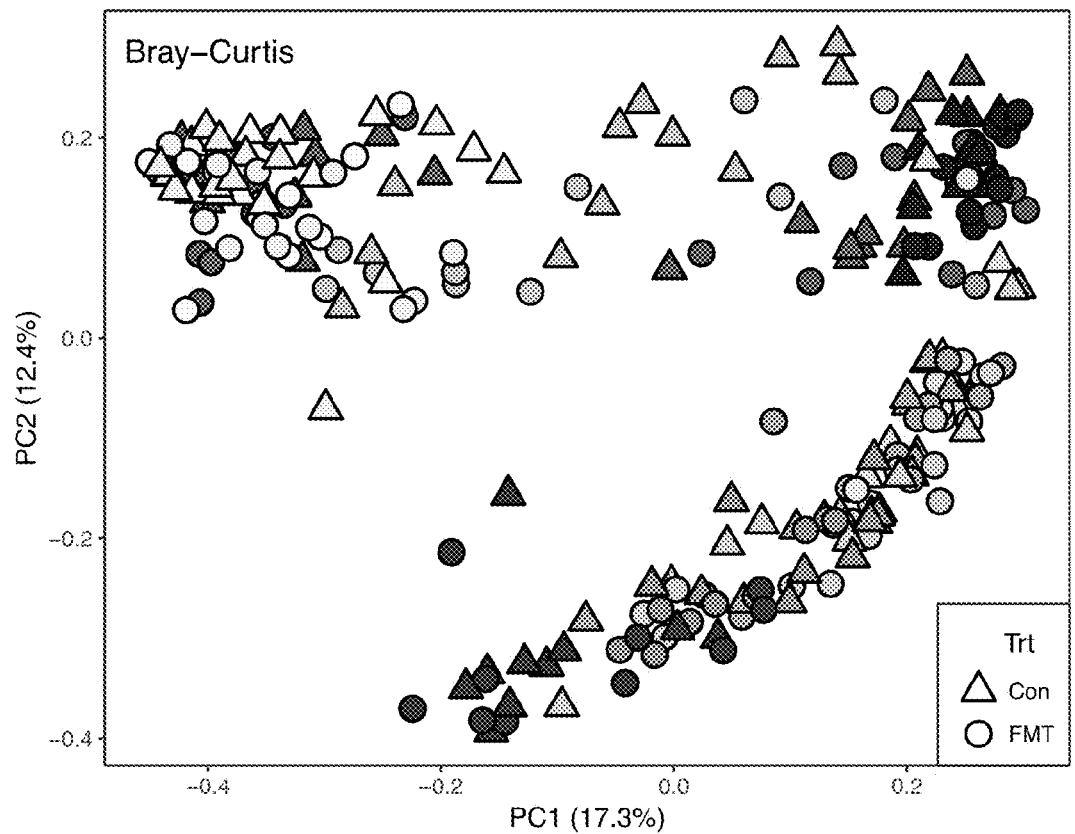

d. Validation-FMT

Bray-Curtis

Fig. 21 (continued)
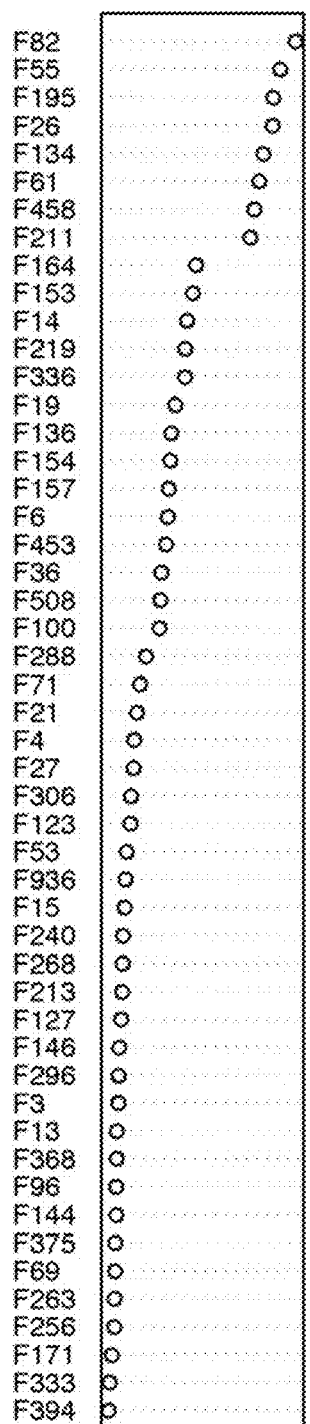
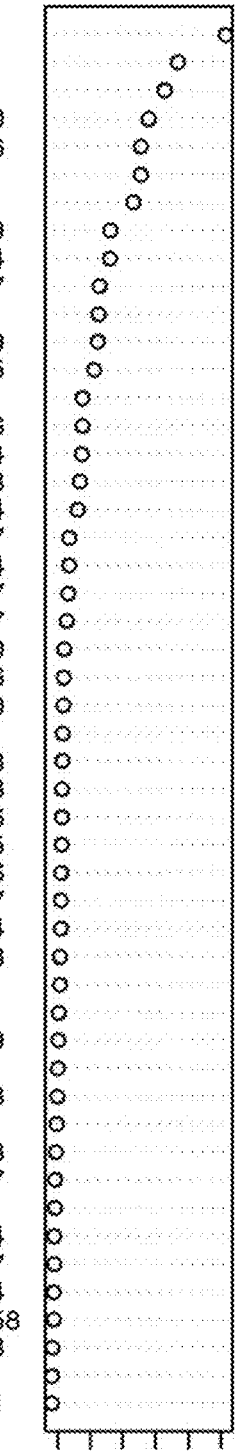

SEQUENCE LISTING

<160> NUMBER OF SEQ ID NOS: 6

<210> SEQ ID NO 1
<211> LENGTH: 240
<212> TYPE: DNA
<213> ORGANISM: Streptococcus sp.
<220> FEATURE:
<221> NAME/KEY: misc_feature
<222> LOCATION: (1)..(240)
<223> OTHER INFORMATION: 16s rDNA v4 region of bacterial feature "F2"

<400> SEQUENCE: 1
tacgtaggtc ccgagcgttg tccggattta ttgggcgtaa agcgagcgca ggcggtttaa    60
taagtctgaa gttaaaggca gtggcttaac cattgttcgc tttggaaact gttaaacttg   120
agtgcagaag gggagagtgg aattccatgt gtagcggtga aatgcgtaga tatatggagg   180
aacaccggtg gcgaaagcgg ctctctggtc tgtaactgac gctgaggctc gaaagcgtgg   240

<210> SEQ ID NO 2
<211> LENGTH: 949
<212> TYPE: DNA
<213> ORGANISM: Streptococcus sp.
<220> FEATURE:
<221> NAME/KEY: misc_feature
<223> OTHER INFORMATION: 16s rRNA sequence of bacterial isolate "StrepX"

<400> SEQUENCE: 2
ccagcagccg cggtaatacg taggtcccga gcgttgtccg gatttattgg gcgtaaagcg    60
agcgcaggcg gtttaataag tctgaagtta aaggcagtgg cttaaccatt gttcgctttg   120
gaaactgtta aacttgagtg cagaagggga gagtggaatt ccatgtgtag cggtgaaatg   180
cgtagatata tggaggaaca ccggtggcga aagcggctct ctggtctgta actgacgctg   240
aggctcgaaa gcgtggggag caaacaggat tagataccct ggtagtccac gccgtaaacg   300
atgagtgcta ggtgttaggc cctttccggg gcttagtgcc gcagctaacg cattaagcac   360
tccgcctggg gagtacgacc gcaaggttga aactcaaagg aattgacggg ggcccgcaca   420
agcggtggag catgtggttt aattcgaagc aacgcgaaga accttaccag gtcttgacat   480
cccgatgcta tttctagaga tagaaagttt cttcggaaca tcggtgacag gtggtgcatg   540
gttgtcgtca gctcgtgtcg tgagatgttg ggttaagtcc cgcaacgagc gcaaccccta   600
ttgttagttg ccatcattca gttgggcact ctagcgagac tgccggtaat aaaccggagg   660
aaggtgggga tgacgtcaaa tcatcatgcc ccttatgacc tgggctacac acgtgctaca   720
atggttggta caacgagtcg caagtcggtg acggcaagca aatctcttaa agccaatctc   780
agttcggatt gtaggctgca actcgcctac atgaagtcgg aatcgctagt aatcgcggat   840
cagcacgccg cggtgaatac gttcccgggc cttgtacaca ccgcccgtca caccacgaga   900
gtttgtaaca cccgaagtcg gtgaggtaac ctttagga ccagccgcc                949

<210> SEQ ID NO 3
<211> LENGTH: 240
<212> TYPE: DNA
<213> ORGANISM: Lactobacillus sp.
<220> FEATURE:
<221> NAME/KEY: misc_feature
<222> LOCATION: (1)..(240)
<223> OTHER INFORMATION: 16s rDNA v4 region of bacterial feature "F3546"

<400> SEQUENCE: 3
tacgtaggtg gcaagcgttg tccggattta ttgggcgtaa agcgagcgca ggcggttttt    60

```
taagtctgat gtgaaagcct tcggctcaac cgaagaagtg catcggaaac tgggaaactt    120
gagtgcagaa gaggacagtg gaactccatg tgtagcggtg aaatgcgtag atatatggaa    180
gaacaccagt ggcgaaggcg ctgtctggt ctgtaactga cgctgaggct cgaaagtatg     240

<210> SEQ ID NO 4
<211> LENGTH: 684
<212> TYPE: DNA
<213> ORGANISM: Lactobacillus sp.
<220> FEATURE:
<221> NAME/KEY: misc_feature
<222> LOCATION: (1)..(684)
<223> OTHER INFORMATION: 16s rRNA sequence of bacterial isolate "LactX"

<400> SEQUENCE: 4
tcgacgactc tggtattgat tggtgcttgc ctcatgattt acatttnant gantggcgaa    60
ctggtgagta acacgtggga aacctgccca gaagcggggg ataacacctg gaaacagatg    120
ctaataccgc ataacaactt ggaccgcatg gtccaagttt gaaagatggc ttcggctatc    180
acttttggat ggtcccgcgg cgtattagct agatggtggg gtaacggctc accatggcaa    240
tgatacgtag ccgacctgag agggtaatcg gccacattgg gactgagaca cggcccaaac    300
tcctacggga ggcagcagta gggaatcttc cacaatggac gaaagtctga tggagcaacg    360
ccgcgtgagt gaagaagggt ttcggctcgt aaaactctgt tgttaaagaa gaacatatct    420
gagagtaact gttcaggtat tgacggtatt taaccagaaa gccacggcta actacgtgcc    480
agcagccgcg gtaatacgta ggtggcaagc gttgtccgga tttattgggc gtaaagcgag    540
cgcaggcggt tttttaagtc tgatgtgaaa gccttcggct caaccgaaga agtgcatcgg    600
aaactgggaa acttgagtgc agaagaggac agtggaactc catgtgtagc ggtgaaatgc    660
gtagatatat ggaagaacac cagt                                           684

<210> SEQ ID NO 5
<211> LENGTH: 19
<212> TYPE: DNA
<213> ORGANISM: Artificial Sequence
<220> FEATURE:
<223> OTHER INFORMATION: Synthetic - Forward primer for amplifying the
      16s rDNA v4 region

<400> SEQUENCE: 5
gtgccagcmg ccgcggtaa                                                 19

<210> SEQ ID NO 6
<211> LENGTH: 20
<212> TYPE: DNA
<213> ORGANISM: Artificial Sequence
<220> FEATURE:
<223> OTHER INFORMATION: Synthetic - Reverse primer for amplifying the
      16s rDNA v4 region

<400> SEQUENCE: 6
ggactachvg ggtwtctaat                                                20
```

US 12,220,435 B2

SWINE ORIGIN PROBIOTICS THAT PROMOTE HEALTH AND GROWTH PERFORMANCE IN PIGS

CROSS-REFERENCE TO RELATED APPLICATIONS

This application claims priority to U.S. Provisional Application No. 63/037,435 filed on Jun. 10, 2020, the contents of which are incorporated by reference in their entireties.

SEQUENCE LISTING

A Sequence Listing accompanies this application and is submitted as an ASCII text file of the sequence listing named "169946_00625_ST25.txt" which is 4,393 bytes in size and was created on May 26, 2021. The sequence listing is electronically submitted via EFS-Web with the application and is incorporated herein by reference in its entirety.

INTRODUCTION

In the swine production industry, weaning and the subsequent nursery stage represents a time of gastrointestinal and immune instability in pigs. Diets are rapidly changed from a pre-weaning milk diet to a corn-soybean meal based diet containing complex carbohydrates by the end of the nursery period. Drastic dietary shifts require the pig's digestive tract to rapidly adjust to newly available substrates, which is complicated by low feed intakes at early weanling. These stressors provide the perfect environment for pathogenic bacteria to colonize the gastrointestinal tract, leading to disruption of gut barrier integrity and increased susceptibility to infectious diseases. In the growing and finishing stages, gut microbiome dysbiosis, pathogen infection, and feed efficiency are major threats to pig health and growth performance.

To prevent colonization by detrimental pathogenic microorganisms, antibiotics are routinely fed to nursery pigs to improve growth performance. However, the use of antibiotics is under increasing public scrutiny as a result of concerns over antibiotic resistance, and the livestock industry is under pressure to find alternatives.

The gut microbiome exerts important effects on host immune system homeostasis, nutrient utilization, and the integrity of gastrointestinal tract barrier. Thus, modulation of the swine gut microbiome using probiotics or prebiotics has become a promising means to prevent pathogen entry and promote the residency of beneficial bacteria. However, studies that have investigated the ability of probiotics to improve health and growth performance have reported inconsistent results. Thus, there remains a need in the swine industry for a probiotic supplement that can improve the growth performance of pigs.

SUMMARY

The present invention provides compositions comprising one or more isolated bacterial strains, wherein at least one of the bacterial strains is selected from: (a) *Lactobacillus* strain LactX, (b) *Streptococcus* strain StrepX3 and (c) *Streptococcus* strain StrepX1.

In a second aspect, the present invention provides methods to increase the growth rate in pigs. The methods comprise administering to the pig the compositions disclosed herein.

In a third aspect, the present invention provides methods to alleviate detrimental growth effects of pig weaning. The methods comprise administering to the pig the compositions disclosed herein.

In a fourth aspect, the present invention provides methods to reduce the time from birth to marketable weight for a pig. The methods comprise administering to the pig the compositions disclosed herein.

BRIEF DESCRIPTION OF THE DRAWINGS

The patent or patent application file contains at least one drawing in color. Copies of this patent or patent application publication with color drawings will be provided by the Office upon request and payment of the necessary fee.

FIG. 12 shows box plots showing the dynamics of 8 of the top 10 bacterial features in the swine gut microbiome of the test trial from birth to market.

FIG. 13 shows PCoA plots showing the swine gut microbiome of the control and FMT groups in the validation trial. Lactation, nursery, growing, and finishing stages are distinguished by colors (blue, purple, green, and red, respectively). Samples with same color densities were collected on the same day. The control group (Con) and the fecal microbiota transplantation (FMT) group are indicated by a triangle and a circle, respectively. Pig donor is indicated in yellow.

DETAILED DESCRIPTION

Figure 1:
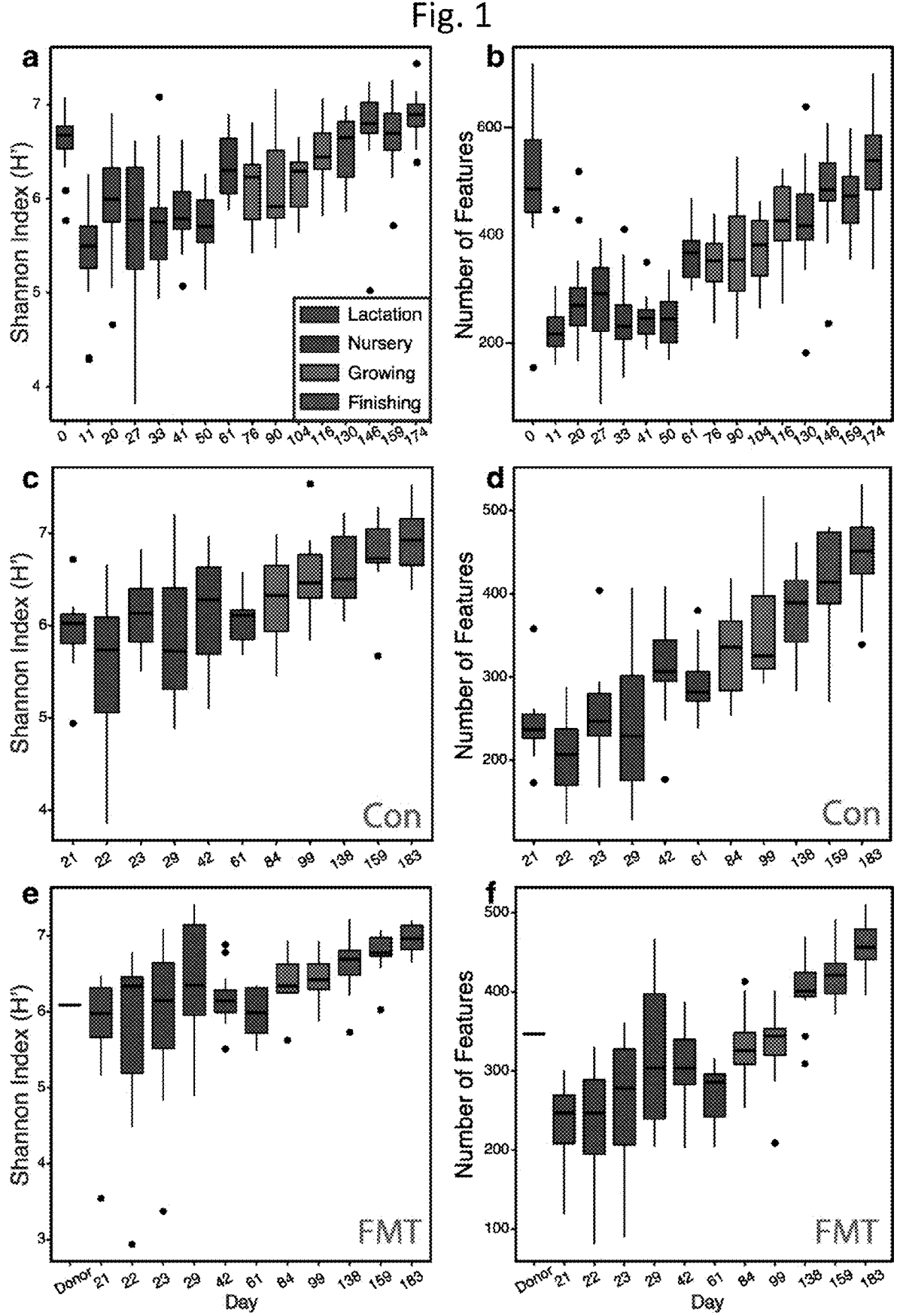
FIG. 1 shows longitudinal changes in the swine gut microbiome community diversity (a, c, e) and richness (b, d, f) from birth to market in the test trial (a and b), and the control group (c and d) and fecal microbiota transplantation (FMT) group (e and f) from the validation trial. Lactation, nursery, growing, and finishing stages are depicted in blue (days 1-20), purple (days 27-61), green (days 76-116) and red (days 130-174), respectively.

The relationship between the swine gut microbiome and animal health and production has been characterized in several studies [1-6]. An imbalanced gut microbiome (dysbiosis) has been associated with high mortality rates during weaning, reduced gut barrier function, and increased pathogen infection, which contribute to substantial losses in the swine industry. Modulation of the swine gut microbiome using probiotics or prebiotics is a promising means of preventing pathogen infections and promoting colonization of beneficial bacteria [7]. Recent studies have expanded our understanding of the swine gut microbiome by exploring its relation to the biogeography of the gastrointestinal tract [5], adiposity [3], nutrient digestibility [4], and growth performance [6]. In particular, the presence of bacterial taxa such as Christensenellaceae, Oscillibacter, Defluviitaleaceae incertae sedis, *Cellulosilyticum*, and *Corynebacterium* has been positively correlated with feed efficiency [8], which is a critical metric for the swine industry.

In the present application, the inventors characterized longitudinal changes in the swine gut microbiome from birth to market, covering the lactation, nursery, growing, and finishing stages of development. They observed significant changes in the swine gut microbiome between these stages and identified stage- and growth-associated bacteria. To validate their discoveries, the inventors inoculated weaning pigs with gut microbiota from a mature, growing stage pig. Although fecal microbiota transplantation (FMT) significantly increased the growth performance of the weaning pigs, it did not change their overall gut microbiome structure. However, a few taxa, including those associated with *Streptococcus* and Clostridiaceae, were enriched in the FMT pigs, suggesting that these bacteria may play a role in promoting animal growth performance.

The inventors then identified bacterial strains that are positively associated with growth performance in pigs at different stages using random forest machine learning. Using a culturomics approach, they isolated 15 of the identified bacterial strains from pigs. After screening for the ability of these strains to tolerate acidic pH and bile acid, the inventors selected three bacterial strains as potential probiotics. By feeding the selected strains to pigs, they found that two of the strains, referred to herein as LactX and StrepX3, significantly increased the body weight of pigs.

Definitions

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

A range includes each individual member. Thus, for example, a group having 1-3 members refers to groups having 1, 2, or 3 members.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

As used herein, the term "probiotic" refers to a live microbial feed supplement which beneficially affects the host animal by improving its intestinal microbial balance. Generally, probiotics are live microorganisms. Different probiotics can have different actions in the gut, and different probiotics may therefore act individually or synergistically to provide a beneficial effect. Although benefits associated with probiotics are favorable, researchers are cautious about drawing general conclusions because benefits vary, depending on type and amount of probiotic consumed, as well as specific combinations of specific probiotics. Thus, specific strains of probiotic bacteria, or specific combinations of strains, can lead to an important health benefit to a mammal. The probiotic compositions of the present invention include the isolated bacterial strains LactX, StrepX3, StrepX1 and combinations thereof.

As used herein the term "prebiotic" refers to non-digestible food components that increase the growth of specific microorganisms in the gastrointestinal tract. "Synbiotics" are compositions comprising at least one probiotic and at least one prebiotic. Such compositions are understood to encourage the growth of beneficial bacteria (e.g., the probiotics). As an illustrative example, fermented dairy products are oftentimes considered synbiotics because they contain live bacteria and the food source needed for them.

The present invention uses bacteria to improve the health of animals, farm animals in particular. Preferably, the animal is a domestic, domesticated animal or an animal which itself is not domestic or domesticated (i.e., wild) but which belongs to the same species or genus as a domestic animal. A wild pig for example would be included in this definition since it belongs to the same species as a domestic pig. Some examples of domestic animals that can be treated include without limitation dogs, cats and other pets, horses, cattle, chicken and other poultry, swine, sheep, and goats. The animal may be a farm or agricultural animal, and these animals include without limitation horses, cattle, chicken and other poultry, swine, sheep, goats. More preferably, the animal is from the suborder Suina. The suborder Suina (also known as Suiformes) is a lineage of mammals that includes the pigs and peccaries of the families Suidae and Tayassuidae. Swine or pig, either wild or domestic, are particularly preferred.

As used herein, the term "isolated" refers to a material that is substantially or essentially free from components that normally accompany it in its native state. For example, an isolated bacterial strain may refer to a bacterial strain that has been purified or removed from naturally or non-naturally occurring components that are present in its naturally occurring environment.

As used herein, the term "body weight" (BW) describes the mass or weight of a pig, and the term "body weight gain" (BWG) refers to an increase in the body weight of a pig. The body weight or body weight gain of a pig may be measured in pounds (lbs). A pig administered a probiotic composition may demonstrate an increase in body weight or body weight gain compared to the body weight or body weight gain of a pig that was not administered a probiotic composition.

As used herein, the term "feed conversion ratio" or "feed conversion rate" is a measurement of the conversion of feed to body weight. The feed conversion ratio may be measured, for example, as the feed intake in grams divided by the body weight gain of a pig in grams. An improvement is measured as a decrease in the feed conversion ratio. Without being bound by theory, a pig with an improved feed conversion ratio may be able to absorb nutrients more effectively due to a change in the absorptive capacity of the pig and/or the availability of more nutrients in the gastrointestinal tract of the pig.

As used herein, the term "feed intake" may include the amount of feed ingested by an animal during regular feeding intervals. The feed intake of an animal may be measured as the amount of feed (e.g., in grams) ingested by an animal. The feed intake of an animal may decrease in an animal provided a feed that includes a probiotic composition without a negative or detrimental effect to body weight or body weight gain of the animal. A reduction in feed intake may correspond with an increase in body weight or body weight gain in an animal provided a feed that includes a probiotic composition.

The terms "increase growth rate," "increase growth production," and "increase growth" refer to the ability of a probiotic composition to produce an increase in body weight, body weight gain, or feed intake or a decrease in feed conversion ratio of a pig relative to the response of a control pig (i.e., a comparable pig that was raised under the same conditions but was not administered the probiotic compositions of the present invention). An "increased" amount is typically a statistically significant amount.

Methods for Enhancing Pig Production:

The present invention provides methods to increase the growth rate in pigs. The methods comprise administering to the pig a probiotic composition described herein.

In some embodiments, an increase in growth rate comprises an increase in body weight of the pig as compared to a control pig. As used herein, the term "control pig" refers to a comparable pig (e.g., of the same breed, sex, and age) that was raised under the same or comparable conditions (e.g., diet, weaning protocol, etc.) but was not administered the probiotic compositions of the present invention. In some embodiments, the body weight of the pig is increased by at least about 2%, 3%, 4%, 5%, 10%, 12%, 15%, 20%, or 25% as compared to the control pig.

The present invention also provides methods to alleviate detrimental growth effects of pig weaning. The methods comprise administering to the pig the probiotic compositions described herein. Weaning is characterized by abrupt transitions, including transitions in diet, maternal environment, and housing facilities. These disruptions often lead to diarrhea, stress, reduced food intake, slow growth, impaired intestinal barrier function, and susceptibility to pathogens in piglets. The bacterial strains of the present invention were selected based on their ability to improve growth performance in pigs. Without wishing to be bound by theory, the probiotic compositions of the present disclosure may improve growth performance by, among other functions, improving gastrointestinal function (e.g., via improved nutrient availability and/or feed conversion ratio). Thus, in some embodiments, the methods of the present invention reduce the overgrowth of opportunistic pathogens, reduce gut inflammation, reduce leakage of bacteria across the gastrointestinal tract barrier, reduce diarrhea, and/or improve immune function. These measures of gut function can be assessed using standard techniques that are known in the art. As is discussed in the Examples, the growth of opportunistic pathogens can be monitored by extracting and sequencing DNA (e.g., 16S rRNA sequencing) from a fecal swab. Gut inflammation can be assessed, for example, by looking at immune cell infiltration (e.g., using immunohistochemistry to label T cells) or at pro-inflammatory cytokine gene expression (e.g., using qPCR). Barrier function can be assessed using a dye penetration assay (e.g., measuring FITC-dextran concentration in the serosal side of intestine), by measuring transepithelial electrical resistance (TEER), by measuring the expression levels of tight junctions proteins, or by evaluating paracellular migration of glucose or mannitol.

Additionally, the present invention provides methods to reduce the time from birth to marketable weight for a pig by administering the compositions disclosed herein. A pig converts feed to meat at a fairly consistent rate until hitting a point where rations are no longer efficiently converted to muscle (i.e., the feed conversion ratio bottoms out). At this point, the return on the investment in feed drops dramatically. Thus, a pig reaches ideal market weight when its metabolism changes and it no longer puts on meat muscle at a rapid rate. The top hog weight varies widely depending on market demand, and is typically anywhere from 250-300 pounds. In some embodiments, the top hog weight is increased by about 2-5%, by about 5-10%, by about 10-15%, by about 15-20%, by about 20-25%, by about 25-30%, by about 30-35%, by about 35-40%, or by greater than 40%. In other embodiments, the time from birth to marketable weight is decreased by about 1-3 days, by about 3-5 days, by about 1 week, by about 2 weeks, or by about 3 weeks.

Exemplary growth phase or growth stage categories and feeding regimens are provided below and in the examples. It is understood that feeding regimens and growth rates will vary for different swine species and agricultural conditions; however, the skilled artisan will be able to draw parallels between the growth phases and feeding regimens outlined herein, and other specific conditions.

Pig production is categorized by the industry into four general stages. First, when pregnant sows reach approximately day 110 of gestation, they are moved to farrowing crates for approximately 3-4 weeks, where the sow gives birth (farrows) and rears her piglets in a protected environment. During this period (i.e., from birth to weaning), the piglets are fed milk from lactating sows and are referred to as being in the "lactation phase." Piglets are weaned (i.e., separated from the sows and given solid food) when they are about 20 days old (d 20). Once weaned, the piglets are moved to a nursery facility for an 8-10 week "nursery phase", in which body weights range from 8 to 25 kg. In the last two stages of pig production, known as the growing (25 to 71 kg) and finishing (71 to 130 kg) stages, pigs are fed until they reach market weight. Pigs normally reach market weight at about six months of age. The "pre-harvest period" includes all four of these stages (i.e., lactation, nursery, growing, and finishing).

In Example 1, the inventors followed a 7- and 8-stage feeding regime in animal trial 1 and 2, respectively. The 7-stage regimen, used in Animal Trial 1, consisted of: a nursery stage comprising three nursery phases (NP1: d 20-33; NP2: d 33-50; NP3: d 50-61), a growing stage comprising two growing phases (GP1: d 61-90; GP2: d 90-116), and a finishing stage comprising two finishing phases (FP1: d 116-146; FP2: d 146-174). Individual pig body weight (BW) and rectal swabs were collected at 3 time points in the lactation phase (d 0, d 11, and d 20), at the end of each phase during nursery stage (d 27, d 33, d 41, d 50, and d 61), at the middle and end of each phase during the growing stage (d 76, d 90, d 104, and d 116), and at the middle and end of each phase during the finishing stage (d 130, d 146, d 159, and d 174).

The 8-stage regimen, used in Animal Trial 2, consisted of: a nursery stage comprising three nursery phases (NP1: d 21-29; NP2: d 29-42; NP3: d 42-61), a growing stage comprising two growing phases (GP1: d 61-84; GP2: d 84-99), and a finishing stage comprising three finishing phases (FP1: d 99-138; FP2: d 138-159; FP3: 159-187). In this trial, each pig was gavaged with a fecal microbiota mixture (FMT) from a healthy growing phase 2 pig for two consecutive days (d 21 and d 22). Individual pig BW and rectal swabs were collected at weaning (d 21) and at the end of each phase, specifically at 4 additional time points in nursery stage (d 22, d 23, d 29, d 42, and d 61), at 2 time points in growing stage (d 84 and d 99), and at 3 time points in finishing stage (d 138, d 159, and d 183).

A third trial was performed to assess the ability of particular bacterial strains (i.e., StrepX and LactX), which were associated with enhanced growth performance in animal trial 2, to be used as swine probiotics. In this trial the pigs were fed using the same 7-stage feeding regimen used in animal trial 1. In this study, the inventors measured the body weight of the pigs at weaning, and at the end of each nursery phase, and at two time points in growing phase (d 66, and d 94). In Example 2, the inventors continued this trial, evaluating the growth of pigs treated with StrepX across the entire pre-harvest period. They demonstrate that treatment with Strep X at weaning increases the growth rate of pigs comparably to treatment with antibiotics, without affecting carcass characteristics. Thus, in some embodiments, the body weight of the pig is determined at one or more of a nursery stage, a growing stage, and a finishing stage.

Pre-weaning and nursery stages are critical periods for swine production, especially the first couple of weeks post-weaning. The stress caused by weaning often results in delayed growth during early nursery stage, which can extend into growing stage. Accordingly, in some embodiments, the probiotic compositions of the present invention are administered to alleviate, lessen, or eliminate the growth lag observed at this critical phase.

In some embodiments, the probiotic compositions are administered to the pig in a single administration. In other embodiments, a booster supplementation of the probiotic compositions is provided after the first administration. In other embodiments, a booster supplementation is administered one or more additional times. In some embodiments, the pig is supplemented continuously with the probiotic compositions.

In some embodiments, the single or first administration is given when the pig is at a pre-weaning stage, at weaning, or at a nursery stage. In specific embodiments, the single or first administration is given when the pig is between about 1 and about 61 days old, between about 18 and about 28 days old, or between about 18 and about 22 days old.

As noted above, in some cases, it will be advantageous to provide the probiotic compositions via multiple administrations. In the Examples, the inventors orally gavaged piglets with LactX or StrepX3 at weaning (i.e., when the pig is about 21 days old) for two consecutive days, and administered a final booster at the end of nursery phase 2 (d 50). Thus, in some embodiments, at least one additional administration is given when the pig is at a nursery stage or is at the end of nursery stage 2. In specific embodiments, at least one additional administration is given when the pig is between about 45 and about 60 days old or is between about 48 and about 52 days old.

Figure 26:
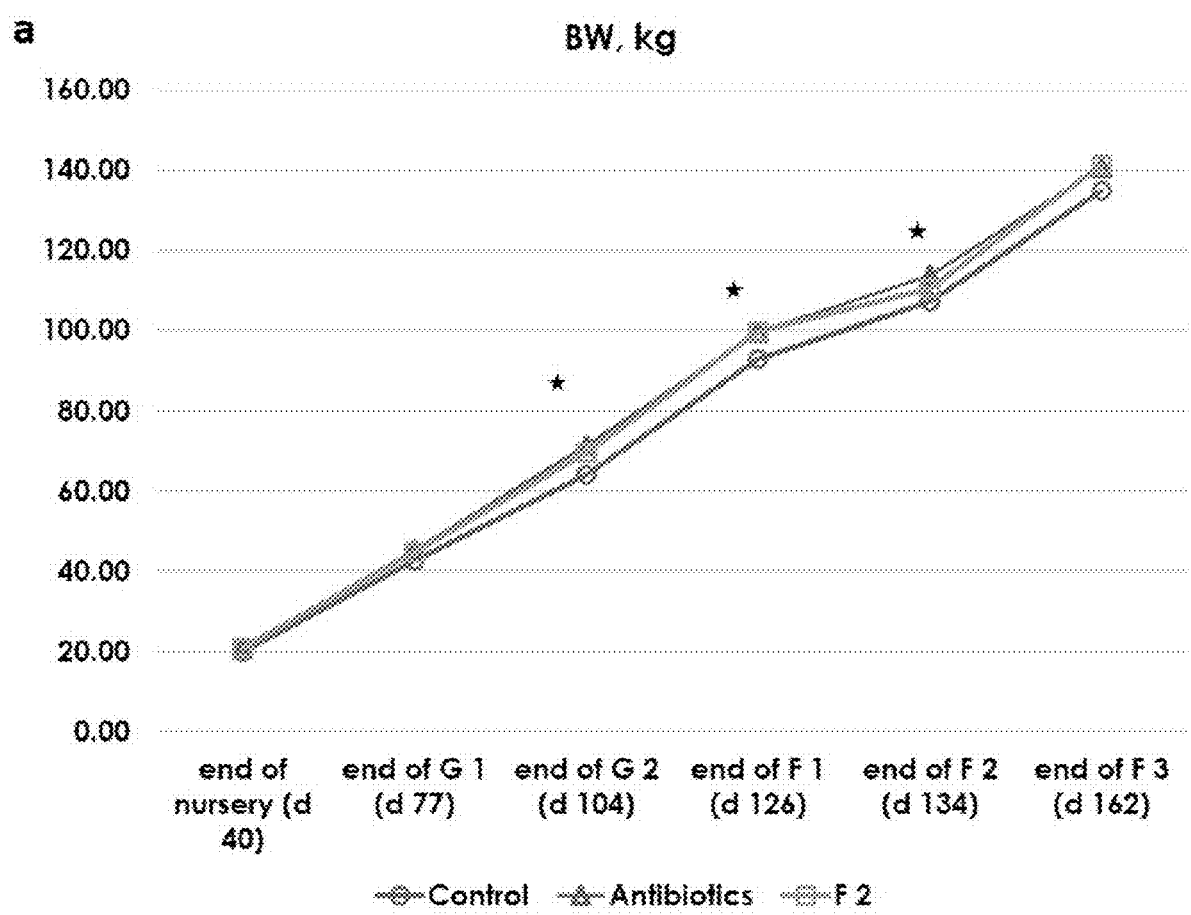
FIG. 26 shows the effect of F2 supplementation and antibiotics on body weight (BW) in wean to market pigs in the third animal trial. Pigs were treated as described in the description of FIG. 25, above. (a) Body weight of the three treatment groups from the end of nursery stage to the end of finishing phase 3. (b) Body weight of the three treatment groups at the final time point (d 162). x.y. The LSmeans without a common superscript tend to be different at 0.05<p≤0.1. ★ indicates a statistically significant difference at p≤0.05.
Figure 26:
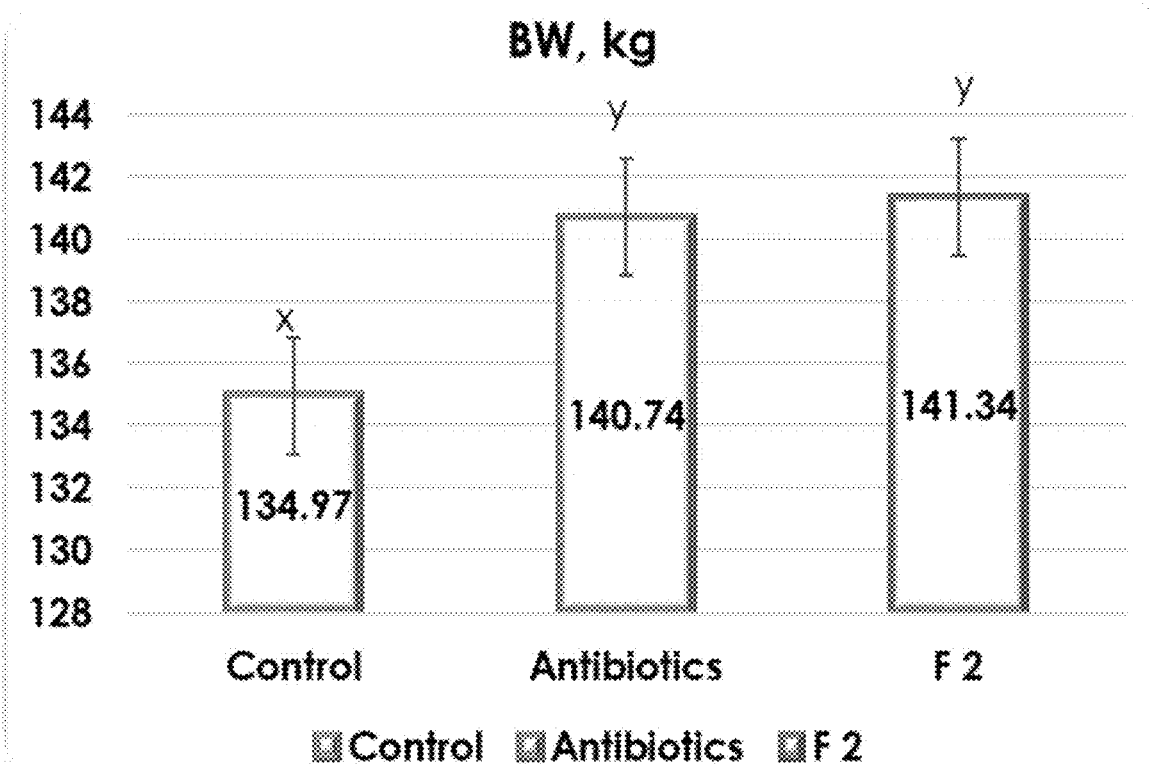

In some embodiments, a measurable improvement (i.e., increased growth rate, reduced growth of opportunistic pathogens, reduced gut inflammation, reduced leakage of bacteria across the gastrointestinal tract barrier, reduced diarrhea, and/or improved immune function) is noted at 13-73 days after a single administration of a probiotic composition or at 12-72 days after a multiple administration regime. For example, when the single administration or the first administration is given at weaning, the measurable improvement may be noted at d 34 and d 53 in the nursery phase, and d 66, and d 94 in the growing phase. However, when the single administration or the first administration is given at a pre-weaning stage, measurable improvements may be noted at earlier points in development, whereas when it is given at a nursery stage the measureable improvements may manifest later in development. In other embodiments, the measurable improvement is a decrease in the time from birth to marketable weight or an increase in the top hog weight, and it is necessarily measured in the finishing stage when the pig reaches the top hog weight. As shown in FIG. 26 measurable improvements in body weight may occur at later stages of development such as between days 104 and 134 or as late as Day 162.

Compositions:

The present invention provides compositions comprising one or more isolated bacterial strains, wherein at least one of the bacterial strains is selected from the *Lactobacillus* bacteria LactX and the *Streptococcus* bacteria StrepX3 or Strep X1. The bacteria may be included in these compositions in several forms including, for example, as live bacteria, dead or inactivated bacteria, or replication incompetent bacteria. These compositions are referred to herein as "probiotic compositions" or "probiotic formulations."

The bacteria described herein, i.e., LactX, StrepX3 and StrepX1, were classified based on current classifications of bacteria from the Ribosomal Database Project using ribosomal RNA gene sequencing data. The sequences of ribosomal RNA (rRNA) genes, including 16S rRNA and 23S rRNA, are commonly used to identify and compare the bacteria or fungi present within a sample since they are found across nearly all forms of life. Those of skill in the art will appreciate that the names and strain designations of bacteria sometimes change over time as more information becomes available. Thus, the present application also provides the specific ribosomal sequences (i.e., the sequence of the V4 regions of 16S rRNA genes) that were detected in the samples in addition to the names of the bacterial strains that were associated with these sequences at the time these experiments were completed. Notably, the 16s rDNA v4 region identified as feature 2 (F2; SEQ ID NO:1) was associated with the bacteria strain StrepX (SEQ ID NO: 2), and the 16s rDNA v4 region identified as feature 3546

(F3546; SEQ ID NO:3) was associated with the bacterial strain LactX (SEQ ID NO:4).

*Lactobacillus* refers to a genus of Gram-positive, facultative anaerobic or microaerophilic, rod-shaped, non-spore-forming, lactic acid bacteria. *Lactobacillus* form biofilms in the gut, allowing them to persist in harsh environmental conditions. As used herein, "LactX" refers to a *Lactobacillus* bacteria having one or more of the following characteristics: (a) the 16S rRNA sequence of SEQ ID NO:4; or (b) ATCC deposit accession number PTA-127487.

*Streptococcus* refers to a genus of Gram-positive coccus or spherical bacteria. Many *Streptococcus* are facultative anaerobes, capable of growth both aerobically and anaerobically. As used herein, "StrepX3" and "StrepX1" refers to *Streptococcus* bacteria having the following characteristics: (a) the 16S rRNA sequence of SEQ ID NO:2; or (b) ATCC deposit accession number PTA-127486 or PTA-127485, respectively.

In some embodiments, the probiotic composition contains between about $10^7$ to $10^{10}$ colony forming units (cfu) of the bacteria (e.g., $10^7$ to $10^{10}$ cfu of LactX, $10^7$ to $10^{10}$ cfu StrepX3 or StrepX1, or $10^7$ to $10^{10}$ cfu of a combination of the three bacterial isolates), between about $10^8$ to $10^{10}$ cfu of the bacteria, or between about $10^8$ to $10^9$ cfu of the bacteria. In embodiments in which the bacteria are included in an animal feed, the animal feed may comprise about $1\times10^7$, about $1\times10^8$, about $1\times10^9$ or about $1\times10^{10}$ cfu of bacteria per gram of animal feed. In some embodiments, the probiotic composition is formulated to include about $1\times10^7$, about $1\times10^8$, about $1\times10^9$ or about $1\times10^{10}$ cfu of bacteria per dose. In one particular embodiment, the probiotic composition is formulated to include about $3\times10^8$ cfu per dose. The animal feed may comprise a probiotic composition including one bacterial strain or a combination of two or more bacterial strains.

The probiotic composition disclosed herein may include, in addition to one or more of LactX, StrepX1 and StrepX3, one or more pharmaceutically acceptable excipients. The phrase "pharmaceutically acceptable" is employed herein to refer to those compounds, materials, compositions, and/or dosage forms which are, within the scope of sound agricultural and/or animal husbandry industry standards and/or medical/veterinary judgment, suitable for use in contact with the tissues of the subject with toxicity, irritation, allergic response, or other problems or complications, commensurate with a reasonable benefit/risk ratio.

The phrase "pharmaceutically acceptable excipient" as used herein refers to an acceptable material, composition or vehicle, such as surfactants, preservatives, stabilizers, flavor enhancers, coloring agents, vitamins, nutrients, prebiotics, additional probiotics, liquid or solid filler, diluent, manufacturing aid (e.g., lubricant, talc magnesium, calcium or zinc stearate, or steric acid), solvent or encapsulating material, involved in carrying or transporting the therapeutic compound for administration to the subject. Each excipient should be "acceptable" in the sense of being compatible with the other ingredients of the formulation and not injurious to the subject. Agriculturally acceptable carriers include, for example, mineral earth (e.g., silicas, lime, calcium carbonate, chalk, clay, etc.) and crushed products of vegetable origin (e.g., cereal meal, wood meal, rice hulls, wheat bran, cellulose powders, etc.). Suitable surfactants may be non-ionic, cationic and/or anionic in nature, and surfactant mixtures that have emulsifying, dispersing and wetting properties, depending on the nature of the active ingredient to be formulated. A probiotic formulation may also include an oil (e.g., mineral oil). Additional examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain flavoring and/or coloring agents may be added.

One of skill in the art will recognize that probiotic compositions are routinely formulated according to their intended use, i.e., route of administration. The probiotic compositions disclosed herein, i.e., compositions including one or more of LactX and StrepX3, can be formulated for oral administration, in a dry or liquid form. By way of example, the present oral probiotic compositions may be in the form of a chewable formulation, a dissolving or dissolved formulation, an encapsulated/coated formulation, a multi-layered lozenge (to separate active ingredients and/or active ingredients and excipients), a slow release/timed release formulation, or other forms suitable for oral delivery known in the art. It may be in the form of a tablet, lozenges, pill, capsule, powders, granules, and aqueous or non-aqueous solutions or suspensions, sprays, drenches, or syrups, frozen, or freeze-dried forms. The probiotic formulations may be flavored, and may be in a variety of shapes or colors.

For oral administration, in some embodiments, the probiotic compositions, are in a lyophilized or dried form, e.g., a dried powder. In some embodiments, the probiotic compositions are formulated as a dry powder that is soluble in water or an organic solvent, or may be directly added to an animal feed during processing or manufacturing. In other embodiments, the probiotic compositions are in a liquid form, e.g., a suspension or solution. In some embodiments, the probiotic compositions are formulated for example, in the form of a paste, cream, a gel, a capsule, an aerosol spray, or a tablet. In some embodiments, the probiotic compositions are formulated to be delivered by oral gavage or drenched. In some embodiments, the probiotic compositions are encased in a coating formulated for release in the gastrointestinal tract. In some embodiments, the probiotic compositions are provided in water consumed by the pig.

In some embodiments, the probiotic composition comprises a direct-fed microbial composition. As used herein, a "direct-fed microbial (DFM)" refers to live (viable) microorganisms that are supplied through feed. A DFM composition may be added to an animal's diet continuously and/or administered as a bolus at particular developmental stage (e.g., at weaning).

The probiotic compositions may be incorporated into pig feed prior to, during, or after feed processing. For example, the compositions may be dusted on the feed product after the pelleting stage. Importantly, at least a portion of the bacteria added to the feed must be able to survive any aspect of feed processing and preparation that they are subjected to (e.g., exposure to high temperatures used in the pelleting stage).

In further embodiments, the compositions are formulated to be applied to the teats of a sow nursing the pig (e.g., as a spray, cream, paste, gel, liquid, etc.).

Advantages of the Present Compositions:

There are several probiotic products that are commercially available for piglets (e.g., SynGenX® from Diamond V). However, most of these marketed products are designed to improve immune function and gut health, and the ability of these products to directly enhance growth performance has yet to be demonstrated. Moreover, most probiotic products lack complete characterization, leaving their optimal delivery time and effect on growth performance unknown. By contrast, the compositions and methods of the present invention offer several, exemplary, non-limiting advantages: (1) they improve growth performance, which directly impacts industry profits; (2) the selected strains (e.g., StrepX) are dominant species within swine gut microbiome (i.e., ranked the 4th most abundant strain across pig lifetime), making it more feasible that they can colonize the swine gut; (3) the selected strains are tough (e.g., tolerate bile acids and HCl), aerobic, and simple to culture, making them relatively easy to manufacture and orally administer.

EXAMPLES

Example 1. Identification of Bacteria within the Swine Microbiome that Predict Growth Performance Despite recent advances in the understanding of the swine gut microbiome at different growth stages, a comprehensive longitudinal study of the dynamics of the gut microbiome across the lifetime (birth to market) of swine is lacking.

To fill in this gap of knowledge, the present inventors collected a total of 273 rectal swabs from 18 pigs during the lactation (day 0, 11, 20), nursery (day 27, 33, 41, 50, 61), growing (day 76, 90, 104, 116), and finishing (day 130, 146, 159, 174) stages of development. DNA was extracted and subjected to sequencing using an Illumina Miseq sequencer targeting the V4 region of the 16S rRNA gene. Sequences were analyzed with the Deblur algorithm in the QIIME2 package. Seventeen phyla were detected in the pig gut microbiome across the tested developmental stages, with Firmicutes and Bacteroidetes being the most abundant. Alpha diversity, measured as community richness (e.g., number of observed features) and diversity (e.g., Shannon Index), increased overall across the lifetime of the pigs. Distinct shifts in the microbiome structure were observed at different growth stages, and LEfSe analysis revealed 91 bacterial features that are stage-specific. Therefore, the inventors sought to identify growth performance-associated bacterial taxa to be used as potential probiotics.

To this end, the inventors first performed a regression-based random forest analysis to identify the top 50 bacterial features that predict growth performance at each stage. To validate these discoveries, they performed fecal microbiota transplantation (FMT) by inoculating weanling pigs with mature fecal microbiota from a growing stage pig. While FMT remarkably increased growth performance, it did not change the overall swine gut microbiome. Similar stage-specific patterns in microbiome diversity and structures were also observed in the FMT pigs and their littermates, and diet (especially crude fiber from corn) was shown to be a more important determinant of the swine gut microbiome. However, a few taxa including those associated with *Streptococcus* and Clostridiaceae, were enriched in the FMT pigs, suggesting that these bacteria may play a role in promoting animal growth performance. Thus, this study underscores the importance of optimizing stage-specific probiotics to improve animal health and production.

Materials and Methods

Study Design and Animals
Animal Trial 1 (Test Trial):

Pigs were managed according to the Institutional Animal Care and Use Committee (IACUC) approved protocol #19017. Rectal swabs were collected from 18 pigs (PIC29*380) born from 3 sows (second parity). Among these pigs, 17 were followed throughout all the different growth stages. The piglets were sow fed during lactation till weaning at day 20 (d 20), when they were transferred to an offsite nursery facility. Piglets were stratified by sow with two littermates housed in a pen. On d 61, pigs were moved to a growing and finishing facility together with their penmates. All pigs were fed with a seven-feeding-phase regime including three nursery phases (NP1: d 20-33; NP2: d 33-50; NP3: d 50-61), two growing phases (GP1: d 61-90; GP2: d 90-116), and two finishing phases (FP1: d 116-146; FP2: d 146-174). All diets were antibiotics-free and dietary nutrients met or exceeded the NRC (2012) recommendation. Individual pig body weight (BW) and rectal swabs were collected on d 0, 11, and 20 during lactation, at the end of each phase during nursery period, in the middle and the end of each phase during growing/finishing period (Table 1).

TABLE 1

Fecal swab samples collected and used for data analysis in animal trial 1

| Age (day) | Feed phase | Growth stage | Number of samples |
|---|---|---|---|
| 0 | NA | Lactation | 18 |
| 11 | NA | Lactation | 18 |
| 20 | NA | Lactation | 17 |
| 27 | phase 1 | Nursery | 17 |
| 33 | phase 1 | Nursery | 17 |
| 41 | phase 2 | Nursery | 17 |
| 50 | phase 2 | Nursery | 16 |
| 61 | phase 3 | Nursery | 16 |
| 76 | phase 1 | Growing | 17 |
| 90 | phase 1 | Growing | 17 |
| 104 | phase 2 | Growing | 16 |
| 116 | phase 2 | Growing | 17 |
| 130 | phase 1 | Finishing | 16 |
| 146 | phase 1 | Finishing | 17 |
| 159 | phase 2 | Finishing | 17 |
| 174 | phase 2 | Finishing | 17 |

Animal Trial 2 (Validation Trial):

To validate the discoveries from Trial 1, a total of 24 weaned pigs (PIC29*380) were selected. Pigs were blocked by sow, and assigned to one of four pens in an onsite nursery facility (6 pigs per pen). On weaning day (d 21 of age), half of the pigs (n=12) were treated with fecal microbiota transplantation (FMT). For the FMT, freshly defecated feces from a mature healthy pig from growing stage phase 2 were collected from anus after rectal massage, and were then transferred into a sterile Whirl-Pak® filter bag with a pore size of 0.33 mm (Nasco Fort Atkinson, WI) filled with 20% glycerol in PBS. Bacterial cells were detached from fecal matter after shaking at high speed for 2 minutes using a Stomacher™400 (Seward Ltd, West Sussex, UK). Filtrates were then transferred into 50 ml conical tubes and stored at −80° C. freezer. Each pig was gavaged with 3 ml filtrates for two consecutive days (d 21 and d 22). Pigs were fed a total of 8 feeding phases regimes in this trial: three nursery phases (NP1: d 21-29; NP2: d 29-42; NP3: d 42-61), two growing phases (GP1: d 61-84; GP2: d 84-99), and three finishing phases (FP1: 99-138; FP2: d 138-159; FP3: 159-187). All diets were antibiotic-free and met or exceeded NRC (2012)

recommendation on nutrient requirement for each stage of pigs. Individual pig BW and rectal swab was collected at weaning and at the end of each phase (Table 2).

TABLE 2

Fecal swab samples collected and used for data analysis in animal trial 2

| Age (day) | Feed Phase | Growth stage | # samples (control) | # samples (FMT) |
|---|---|---|---|---|
| 21 | phase 1 | Nursery | 12 | 11 |
| 22 | phase 1 | Nursery | 11 | 11 |
| 23 | phase 1 | Nursery | 12 | 12 |
| 29 | phase 1 | Nursery | 12 | 11 |
| 42 | phase 2 | Nursery | 12 | 12 |
| 61 | phase 3 | Nursery | 12 | 12 |
| 84 | phase 1 | Growing | 10 | 12 |
| 99 | phase 2 | Growing | 11 | 11 |
| 138 | phase 1 | Finishing | 10 | 11 |
| 159 | phase 2 | Finishing | 11 | 10 |
| 183 | phase 3 | Finishing | 10 | 10 |

Sample Collection, DNA Extraction, and Sequencing

A total of 273 rectal swabs (Puritan®Opti-Swab® Liquid Amies Collection & transport System; Puritan LLC, Guilford, ME) were collected from 17 pigs repeatedly during lactation (d 0, 11, 20), nursery (d 27, 33, 41, 50, 61), growing (d 76, 90, 104, 116), and finishing (d 130, 146, 159, and 174) stages in animal Trial 1, with two more samples collected from the 18th pig that died during lactation stage. In Trial 2, a total of 246 rectal swabs were collected from 24 pigs repeatedly at the end of lactation (d 21), nursery (d 22, 23, 29, 42, and 61), growing (d 84 and 99), and finishing (d 138, 159 and 183) periods (Table 2) to validate the findings from Trial 1. These swabs were stored at −80° C. until DNA extraction was performed.

A total of 200 μL fecal swab solution was used for DNA extraction with PowerLyzer PowerSoil DNA Isolation Kit (Qiagen, Hilden, Germany) according to the manufacturer's protocol. Extracted DNA was quantified using NanoDrop (Thermo Fisher Scientific, Wilmington, DE, USA) and diluted to 10 ng/μL with DNase- and RNase-free water. Libraries were constructed according to published protocol [14]. Briefly, the V4 region of the bacterial 16S rRNA gene was amplified using universal primers (F: 5'-GTGCCAGCMGCCGCGGTAA-3' (SEQ ID NO:5) and R: 5'-GGACTACHVGGGTWTCTAAT-3' (SEQ ID NO:6)). Agarose gel electrophoresis was performed to verify the size of amplicons. The SequalPrep Normalization Plate Kit (Invitrogen, Carlsbad, CA, USA) was used to clean up and normalize PCR products. Normalized amplicons were pooled in equal volume and their quality and quantity were measured with Agilent bioanalyzer 2100 (Agilent, Santa Clara, CA, USA) and quantitative RT-PCR, respectively. Illumina MiSeq 2×250 bp paired-end sequencing (MiSeq Reagent Kit v2, 500 cycles, 20% PhiX) was used to sequence pooled amplicons. Negative controls for DNA extraction and PCR amplification, mock community (Zymo-BIOMICS™ Microbial Community Standard (Zymo, Irvine, CA, USA)) and a generous donor were included in each MiSeq run for quality control.

Microbiome Data Analysis

Illumina MiSeq fastq reads were imported into the QIIME2 platform (version 2.4) and were processed by the Deblur program [15], which obtains single-nucleotide resolution based on error profiles within samples. Deblur denoised sequences are usually called amplicon sequence variants (ASVs), exact sequence variants (ESVs), or sub-operational taxonomic units (sub-OTUs). In this study, these sequences were assigned to bacterial features, which are synonymous to ASVs, ESVs, and sub-OTUs and sequences between different features differed at the single-nucleotide level. Deblur generates unique features that could be compared between different studies. To minimize the effects of sequencing depth on alpha and beta diversity measure the number of reads from each sample was rarefied to 4,000, which still yielded an average Good's coverage of 97.90%. The taxonomy of these features was assigned to the Greengenes reference database (13-8 version) classifier with 99% similarity. A features table was generated using Qiime2's qiime vsearch cluster-features-closed-reference command. Determination of alpha and beta diversities and analysis of similarity (ANOSIM) were also conducted in qiime2. This data analysis pipeline yielded high quality sequences as suggested by the eight bacterial taxa from the mock communities that were detected in each run with consistent relative abundance as expected.

Permutational multivariate analysis of variance (PERMANOVA) was performed to identify the factors shaping the dynamics of the swine gut microbiome. PERMANOVA, a distribution-free algorithm, accommodates random effects, repeated measures, and unbalanced datasets [16]. For PERMANOVA analysis, we used the adonis function in the vegan package of R including different independent variables (e.g., age, gender, diet) with default settings (Bray-Curtis distance and 999 permutations). We used strata=pigID to account for the random effects of pigs for repeated measures. Stage-dependent features were identified by using the Linear Discriminant Analysis (LDA) effect size (LEfSe) with default settings (e.g., LDA score>2) [17]. Regression-based Random Forest models were developed to identify bacterial features that correlate with growth performance (body weight), using the default settings in the randomForest package the R project [18]. LEfSe was also used to identify bacterial features differentially represented between the control and the FMT groups in the validation trial.

The SparCC algorithm that is able to estimate the correlations from compositional network was used for network analysis. The network was demonstrated by using the igraph package in R with edges connecting nodes (bacterial taxa) with a correlation co-efficiency over 0.6 or less than-0.6. Clusters were generated based on the betweenness centrality calculated with the Girvan-Newman algorithm [19].

Growth Performance Data Analysis

Data were analyzed using general linear model of SAS (Cary, NC) as complete block design with treatment as a fixed effect. Each individual pig was used as the experimental unit. PDIFF option was used to test differences between least square means of the factor levels.

Data Availability

The datasets generated and analyzed in the current study are available in the Sequence Read Archive (SRA) repository, www.ncbi.nlm.nih.gov/bioproject/531671 (SRA accession #: PRJNA531671, made available on May 30, 2019).

Results:

The Dynamics of the Swine Gut Microbiome from Birth to the Market

We first characterized the dynamics of the swine gut microbiome in the test trial by analyzing a total of 273 rectal swabs collected from birth (d 0) to market (d 174). A total of 2,980,303 high-quality reads from 3,358 features at the single nucleotide resolution were generated with an average of 10,916 reads per sample. After rarefaction of sample reads to 4,000, a total of 3,254 features (1,080,000 total reads) from 270 samples were included for downstream analysis of the swine gut microbial community dynamics. The other three samples with sequence reads number below 4,000 were excluded from further analysis.

Figure 9:
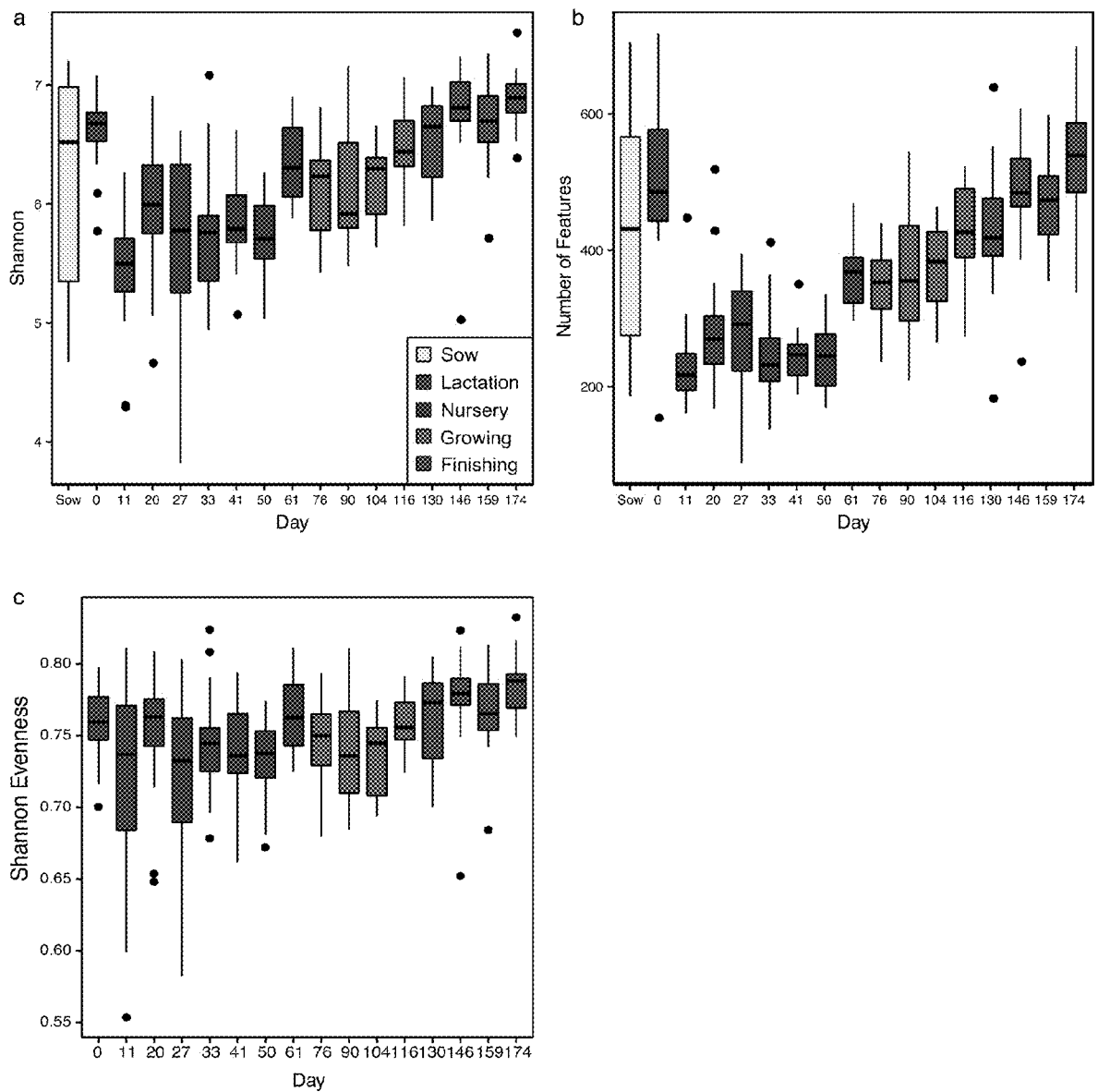
FIG. 9 shows longitudinal changes in swine gut microbiome community diversity (a) and richness (b) in sows and pre-harvest pigs that were followed from birth to market in the test trial, as well as the community evenness (Shannon Evenness) (c). Lactation, nursery, growing, and finishing stages are based on dietary formation and physiological development, and are color-coded with blue (days 1-20), purple (days 27-61), green (days 76-116), and red (days 130-174), respectively. Sow rectal swabs that were collected on farrowing day from another breeding group are coded in yellow.

A high microbial diversity including the number of observed bacterial features and the Shannon index was observed in the meconium (d 0), comparable to the diversity of the adult pigs in this study (FIGS. 1a and b), as well as to those of sows from other trials (FIG. 9). The high microbial diversity dropped dramatically on day 11 and increased on day 20 before weaning. No significant changes in alpha diversity were observed during the first 4 weeks of the nursery stages, even though solid food was provided post-weaning. The overall alpha diversity increased over time starting from the end of the nursery stage, as demonstrated by the Shannon index (H', FIG. 1a) and the number of observed features (FIG. 1b) during the observation period (except d 0). No significant changes in community evenness were observed despite the slight increase in the finishing stage (FIG. 9c).

Significant shifts in community membership and structure from lactation, nursery, growing and finishing stages were observed on the principal coordinates analysis (PCoA) plots based on Bray-Curtis (FIG. 2a) and Jaccard (FIG. 10a) distances. Day 0 samples were distinct from those of the other two lactation time points (day 11 and day 20). The swine gut microbiomes were different between nursery, growing and finishing stages when pigs were fed solid diets (Table 3 and 4), but they were more similar to each other (ANOSIM, nursery vs growing: R=0.425; growing vs finishing: R=0.554, P=0.001 for both) than to the lactation microbiomes when the pigs were fed sow milk (ANOSIM, R>0.97, P=0.001 for all solid feed stages vs lactation; Table 3 and FIG. 10a).

TABLE 3

Dissimilarities in the swine gut microbiome at different growth stages and meconium (d0) revealed by Analysis of similarity (ANOSIM) based on Bray-Curtis distances

| Group 1 | Group 2 | Sample size | R value | p-value | q-value |
| --- | --- | --- | --- | --- | --- |
| Finishing | Growing | 134 | 0.554 | 0.001 | 0.001 |
| Finishing | Lactation | 102 | 0.974 | 0.001 | 0.001 |
| Finishing | Meconium | 85 | 0.903 | 0.001 | 0.001 |
| Finishing | Nursery | 150 | 0.829 | 0.001 | 0.001 |
| Growing | Lactation | 102 | 0.991 | 0.001 | 0.001 |
| Growing | Meconium | 85 | 0.989 | 0.001 | 0.001 |
| Growing | Nursery | 150 | 0.425 | 0.001 | 0.001 |
| Lactation | Meconium | 53 | 0.905 | 0.001 | 0.001 |
| Lactation | Nursery | 118 | 0.981 | 0.001 | 0.001 |
| Meconium | Nursery | 101 | 0.995 | 0.001 | 0.001 |

TABLE 4

Analysis of similarity (ANOSIM) was used to determine swine gut microbiome dissimilarities between the four growth stages and meconium (d 0) in the test study based on the Jaccard distances

| Group 1 | Group 2 | Sample size | Permutations | R value | p-value | q-value |
| --- | --- | --- | --- | --- | --- | --- |
| Finishing | Growing | 134 | 999 | 0.600 | 0.001 | 0.001 |
| Finishing | Lactation | 102 | 999 | 0.995 | 0.001 | 0.001 |
| Finishing | meconium | 85 | 999 | 0.916 | 0.001 | 0.001 |
| Finishing | Nursery | 150 | 999 | 0.810 | 0.001 | 0.001 |
| Growing | Lactation | 102 | 999 | 0.999 | 0.001 | 0.001 |
| Growing | meconium | 85 | 999 | 0.986 | 0.001 | 0.001 |
| Growing | Nursery | 150 | 999 | 0.492 | 0.001 | 0.001 |
| Lactation | meconium | 53 | 999 | 0.907 | 0.001 | 0.001 |
| Lactation | Nursery | 118 | 999 | 0.981 | 0.001 | 0.001 |
| meconium | Nursery | 101 | 999 | 0.987 | 0.001 | 0.001 |

The "Core" and Stage-Associated Microbiomes

Figure 3:
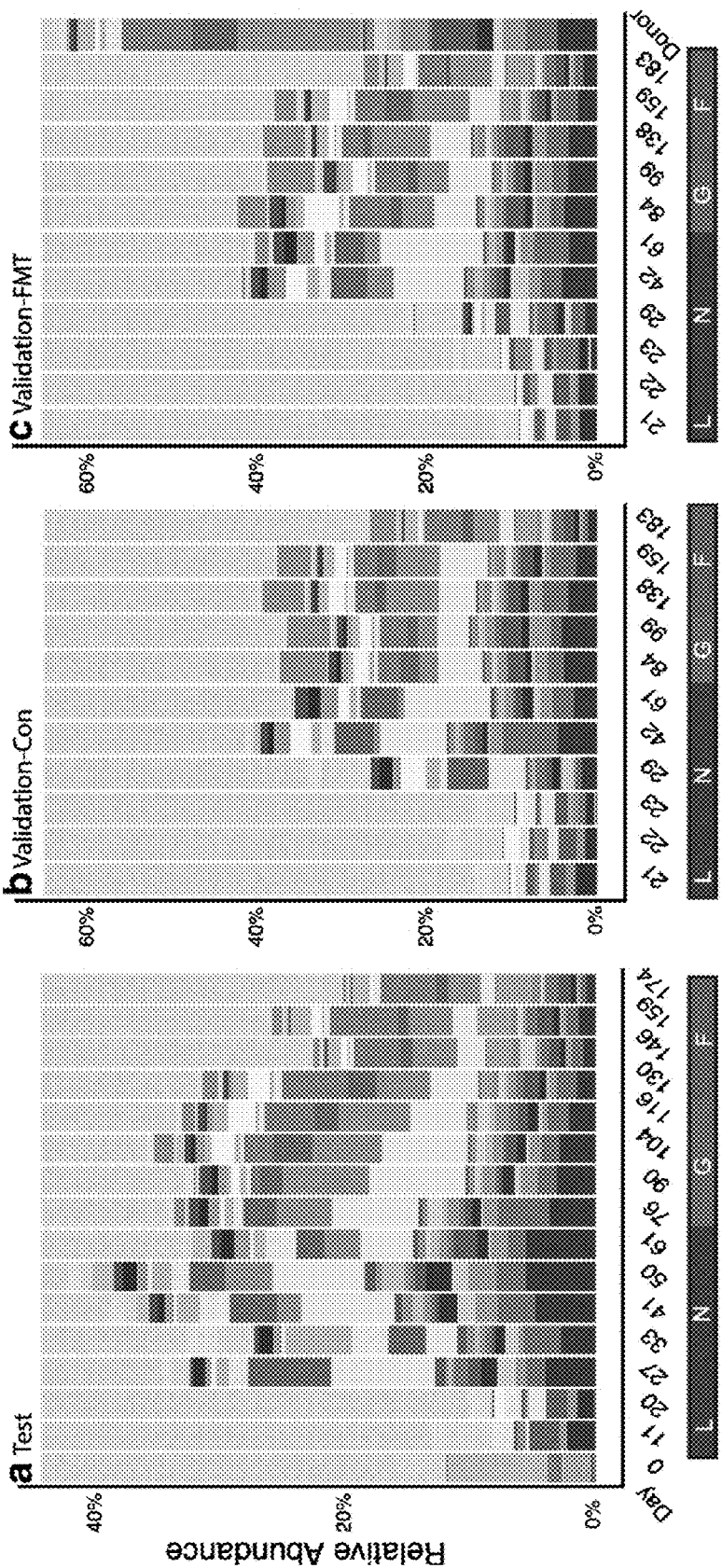
FIG. 3 shows the top 30 features identified in the test trial (a), as well as the control group (b), and the FMT group (c) from the validation trial. Each color represents the relative abundance of a bacterial taxon on the stacked bar chart.
Figure 11:
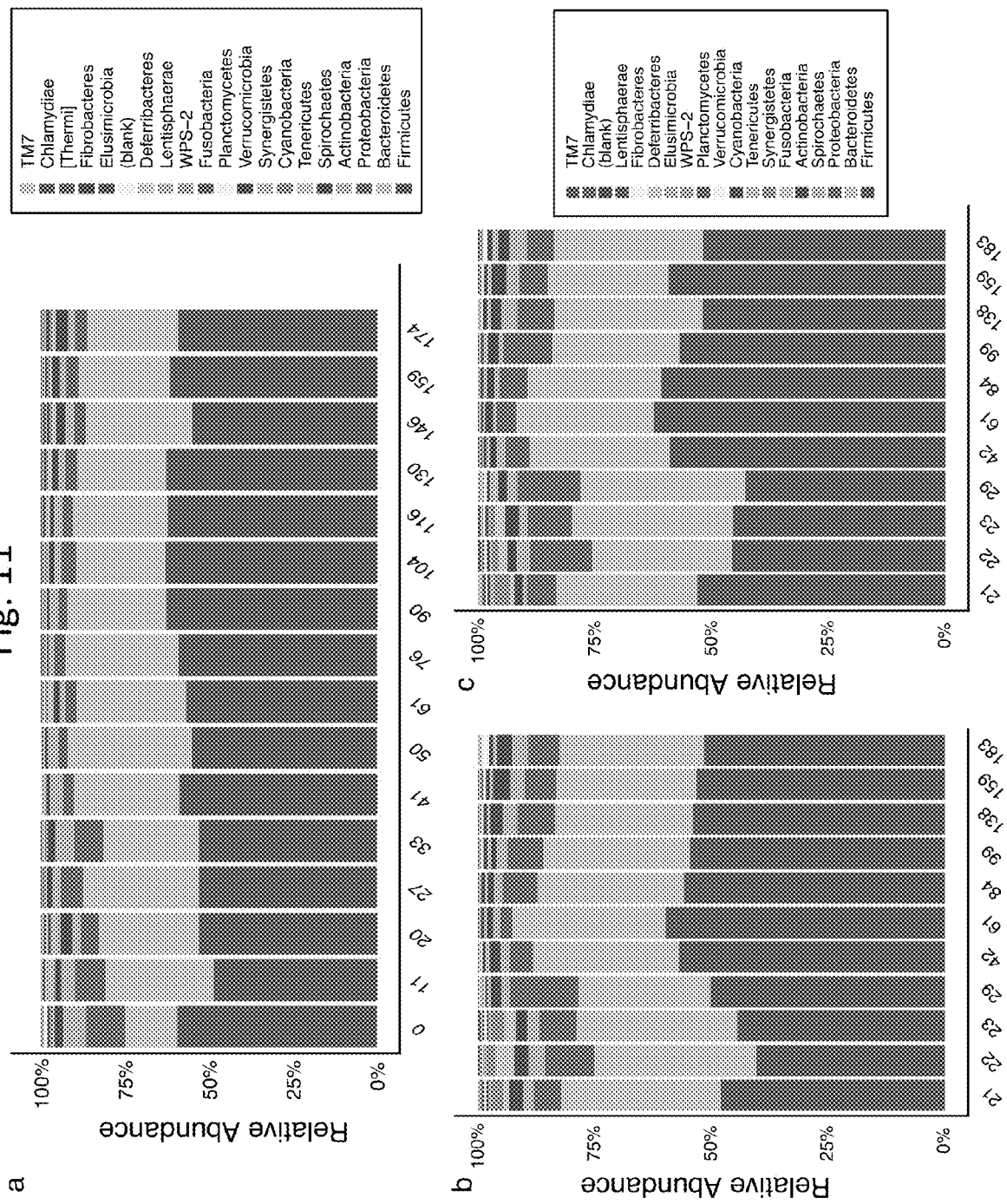
FIG. 11 shows stacked bar charts depicting the longitudinal changes in the swine gut microbiome composition at the phylum level in the test trial (a), the control group (b) and the fecal microbiota transplantation (FMT) group of the validation trial (c).

We next examined the order and timing of bacterial taxa arrival during different stages of the pre-harvest section. At the phylum level, a total of 19 phyla including Firmicutes, Bacteroidetes, Proteobacteria, Actinobacteria were observed, with Firmicutes being the most abundant phylum followed by Bacteroidetes across each stage (FIG. 11a). These two phyla accounted for 70% of the total sequences. At the sub-OTUs level, the top 30 most abundant bacterial features are displayed on stacked bar charts. Among these top 30 taxa, 11 belong to genus *Prevotella*, the most diverse and dominant genus throughout most of the stages, especially after the introduction of solid feed (FIG. 3a).

Figure 4:
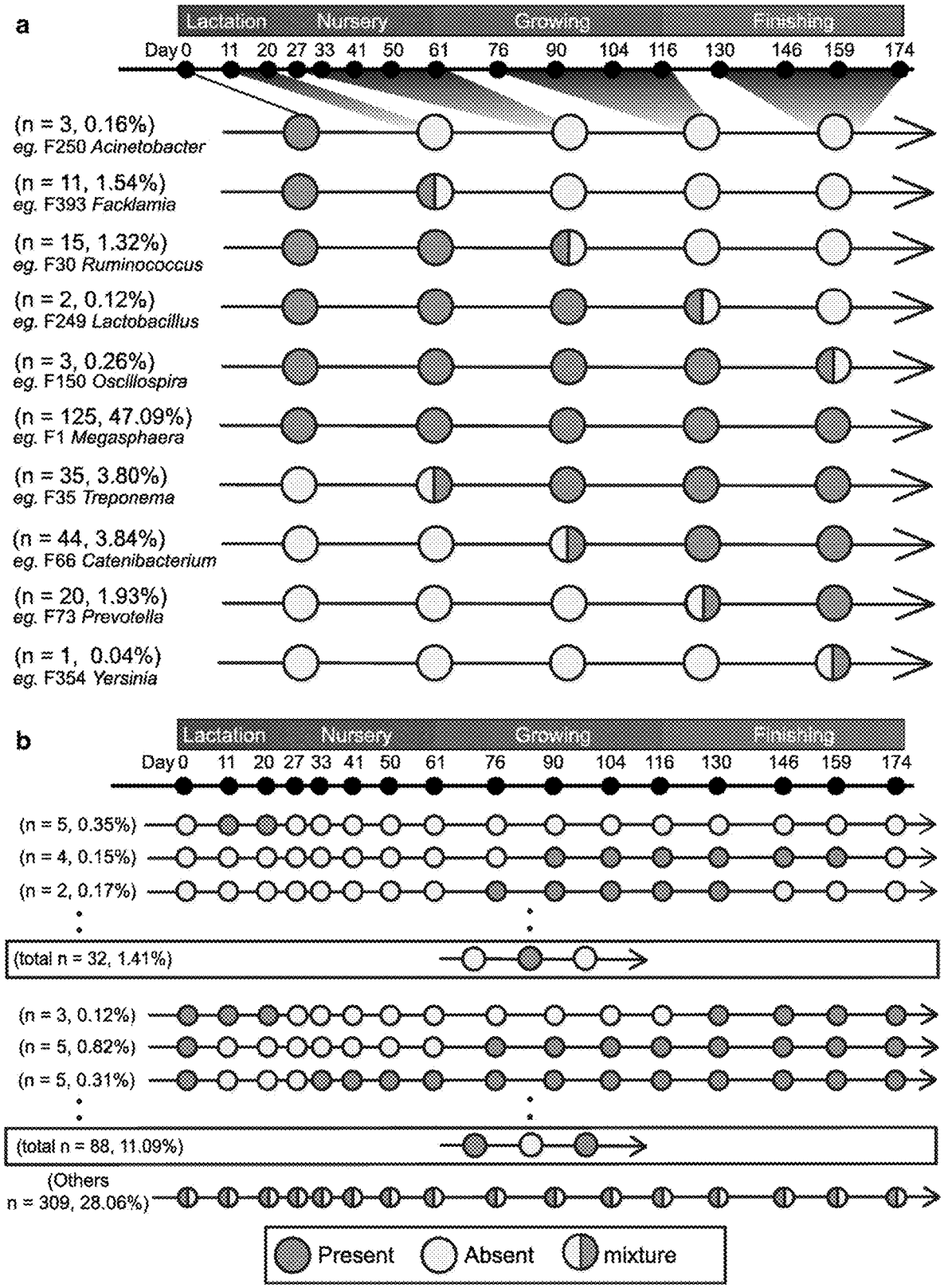
FIG. 4 shows longitudinal occurrence patterns of the swine gut microbiome. The top 700 features based on averaged relative abundance on each day were used to summarize the occurrence patterns. A dark circle indicates the presence of a bacterial taxon while a light circle shows the absence. Mixed color circles mean transition between "presence" and "absence" during each stage or time period.

The appearance order and timing of the swine gut microbiome members are summarized in FIG. 4. Among the top 700 features, 125 features were present, based on their average relative abundance, throughout the entire pre-harvest lifetime and are defined as "core" microbiome or residents of the swine GI-tract. Features that appeared only at certain stages are referred to as "stage-associated." For instance, F250 (*Acinetobacter*) was observed only at birth (d 0). Feature 20 (*Prevotella stercorea*) was abundant during lactation but remarkably decreased in subsequent stages. Feature 7 (*Escherichia coli*) was present during the lactation stage and persisted until the end of nursery phase before phasing out. On the other hand, F3, which is associated with *Prevotella copri*, dramatically increased at the end of the first nursery phase after the introduction of solid food. Other features such as F4 (unclassified Clostridiaceae), 10 (Bacteroidetes YRC22), and 27 (*Clostridium butyricum*), which were rarely observed during lactation and nursery stages, increased rapidly during the growing and finishing stages (FIG. 3*a*). Fluctuations in the relative abundance of bacterial features belonging to other dominant genera such as *Megaphaera*, *Lactobacillus*, and *Streptococcus* were also observed at various time points (FIG. 3*a* and FIG. 12). Finally, features that appeared sporadically at certain stages but disappeared later are called "passengers" (FIG. 4*b*).

Figure 5:
FIG. 5 is a heat map showing the 91 stage-associated bacterial taxa identified by linear discriminant analysis effect size (LEfSe; LDA>2) in the test trial. The top 1000 features (excluding d 0 samples) were used for LEfSe analysis. The heat map shows the average relative abundances on a log scale.

Stage-associated bacterial features were identified by using LEfSe [17], an algorithm that focuses not only on statistical significance but also on biological consistency. The abundance of these features is visualized on a heatmap (FIG. 5). Of note, day 0 samples were not included in the LEfSe analysis since meconium microbiomes were remarkably different from the typical lactation microbiomes on day 11 and day 20 and might bias the stage-specific data. LEfSe analysis confirmed most of the observations mentioned above. For example, F20 was classified as a lactation-associated bacterium whereas F3 was nursery-specific, although both of these taxa belong to *Prevotella* genus. Of note, although the core microbiome members persisted throughout the entire pre-harvest section, their presence also followed a stage-specific pattern. For example, Megasphaera (F1) and *Streptococcus luteciae* (F2) were detected starting d0 until the end of the study but their abundance was relatively low during the lactation stage. Their abundance showed a unimodal pattern: increased starting nursery phase 1, peaked during the end of the nursery phase 3 and growing stage, and started to decrease thereafter (FIG. 5 and FIG. 12).

Figure 6:
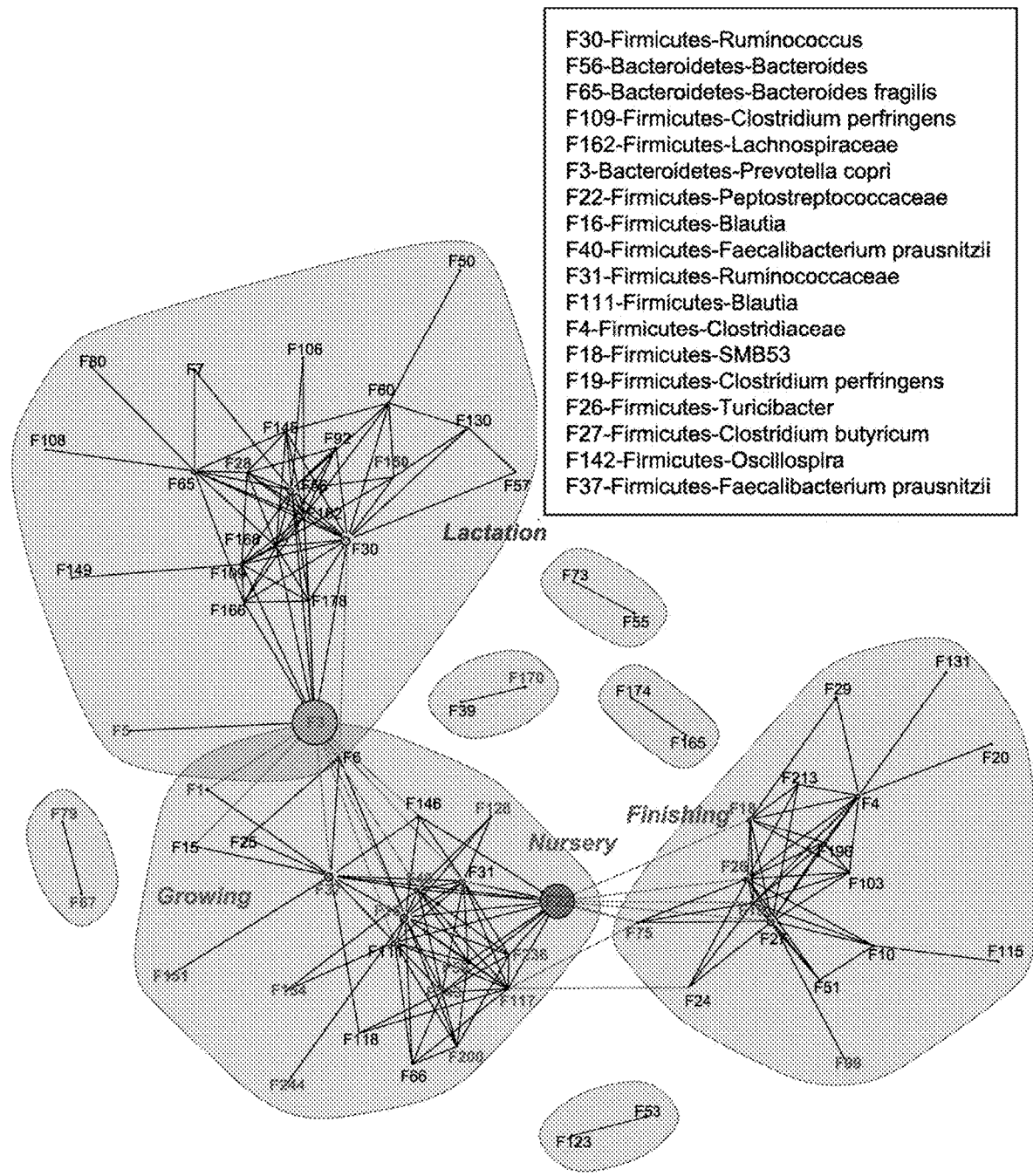
FIG. 6 shows a network analysis of the interactions between bacterial taxa at different growth stages. SparCC was used to calculate the relationships between bacterial taxa. The R package igraph was used to draw the network.

Network analysis using the SparCC algorithm also showed stage-associated interactions between bacterial features (FIG. 6). Three large clusters within the network were observed with stage-associated features connected to one another. The yellow and green clusters connected nodes (bacterial features) associated with the lactation stage and finishing stages, respectively, whereas the pink cluster serves as a bridge connecting these two clusters by two hub nodes, F3 (*Prevotella copri*) and 22 (Peptostreptococcaceae). Bacterial features enriched in the nursery and growing stages were grouped in this cluster.

Validation of the Stage-Associated Swine Gut Microbiome

Figure 7:
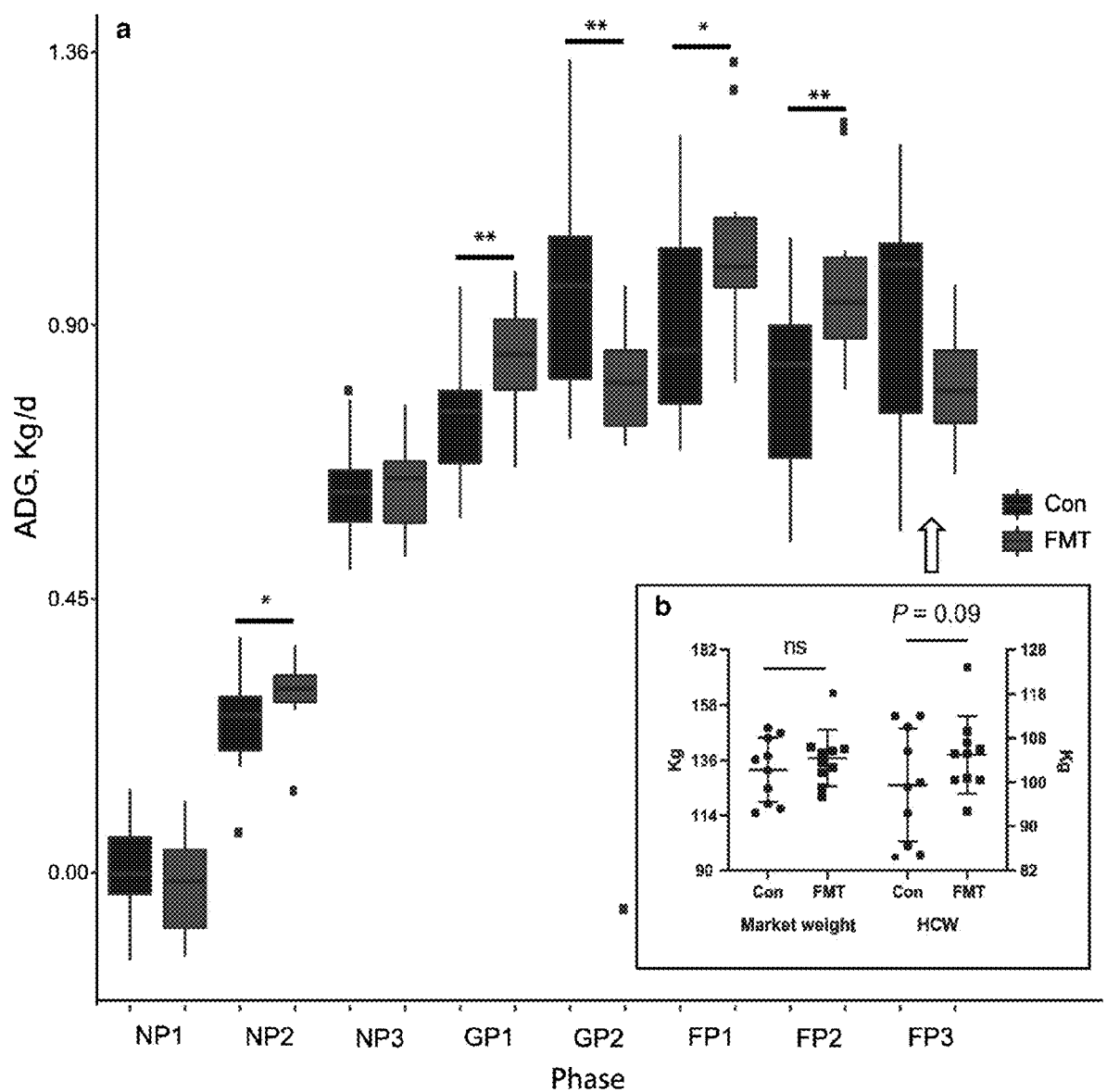
FIG. 7 shows the effect of fecal microbiota transplantation (FMT; the bar on the right side at each phase) as compared to control (CON; left bar on the graph at each phase) on (a) the average daily gain (ADG) at weaning and in subsequent stages of growth, and on (b) the final body weight and hot carcass weight (HCW) of pigs. All pigs were weighed at the beginning and the end of each phase to determine ADG and the market weight. At the end of this trial, all pigs were transferred to a plant where carcass characteristic data were collected. An asterisk (*) indicates a tendency towards a significant difference (0.05<P<0.10); two asterisks (**) indicates a significant difference (P≤0.05).

We next validated the stage-associated swine gut microbiome in a second animal trial (i.e., the validation trial; animal trial 2). At weaning, we inoculated 12 pigs with mature gut microbiota isolated from a growing stage pig (growing phase 2). When compared to their littermates in the control group, FMT recipients had greater average daily gain (ADG) during nursery phase 2 (0.30 vs 0.25 kg, P=0.087), growing phase 1 (0.60 vs 0.53 kg, P=0.042), finishing phase 1 (1.05 vs 0.9 kg, P=0.068), and finishing phase 2 (0.98 vs 0.81 kg, P=0.018), but not at growing phase 2 (0.75 vs 0.96 kg, P=0.042) Although not statistically significant, FMT pigs were 2.3 kg heavier at the end of the second trial and their hot carcass weight (HCW) was 3.5 kg heavier than their littermates (P=0.09, FIG. 7).

Figure 2:
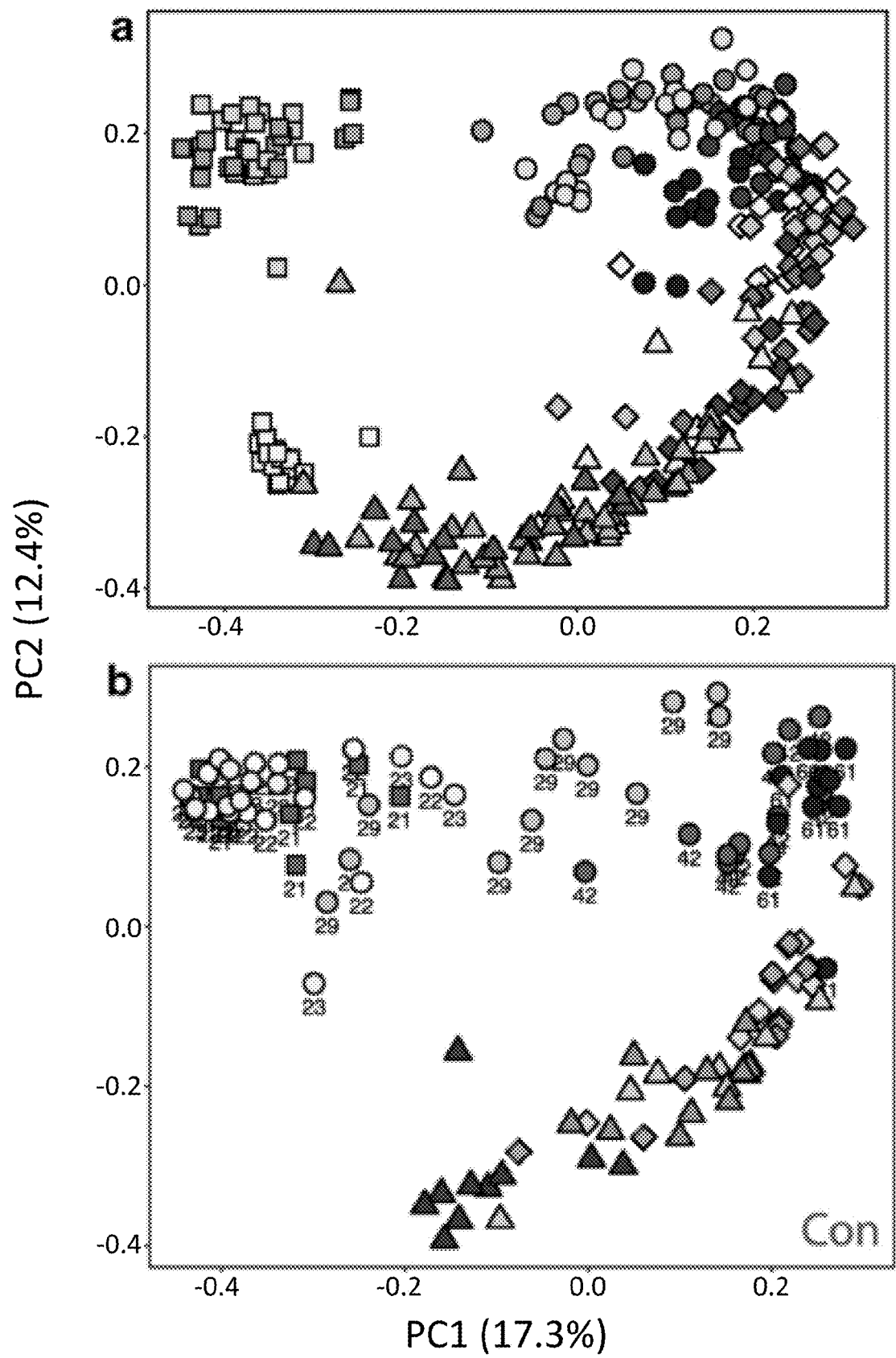
FIG. 2 shows longitudinal changes in the swine gut microbiome structure at different growth stages. Principal coordinate analysis (PCoA) plots based on the Bray-Curtis distances showed distinct clusters in the test trial (a), and the control group (b) and the fecal microbiota transplantation (FMT) group (c) from the validation trial, and all the groups combined (d). Lactation, nursery, growing and finishing stages are differentiated by colors (blue, purple, green and red, respectively) and shapes (square, circle, diamond, and triangle, respectively). The pig donor in the FMT group is indicated with a yellow diamond. Samples with same color densities were collected on the same day.
Figure 2:
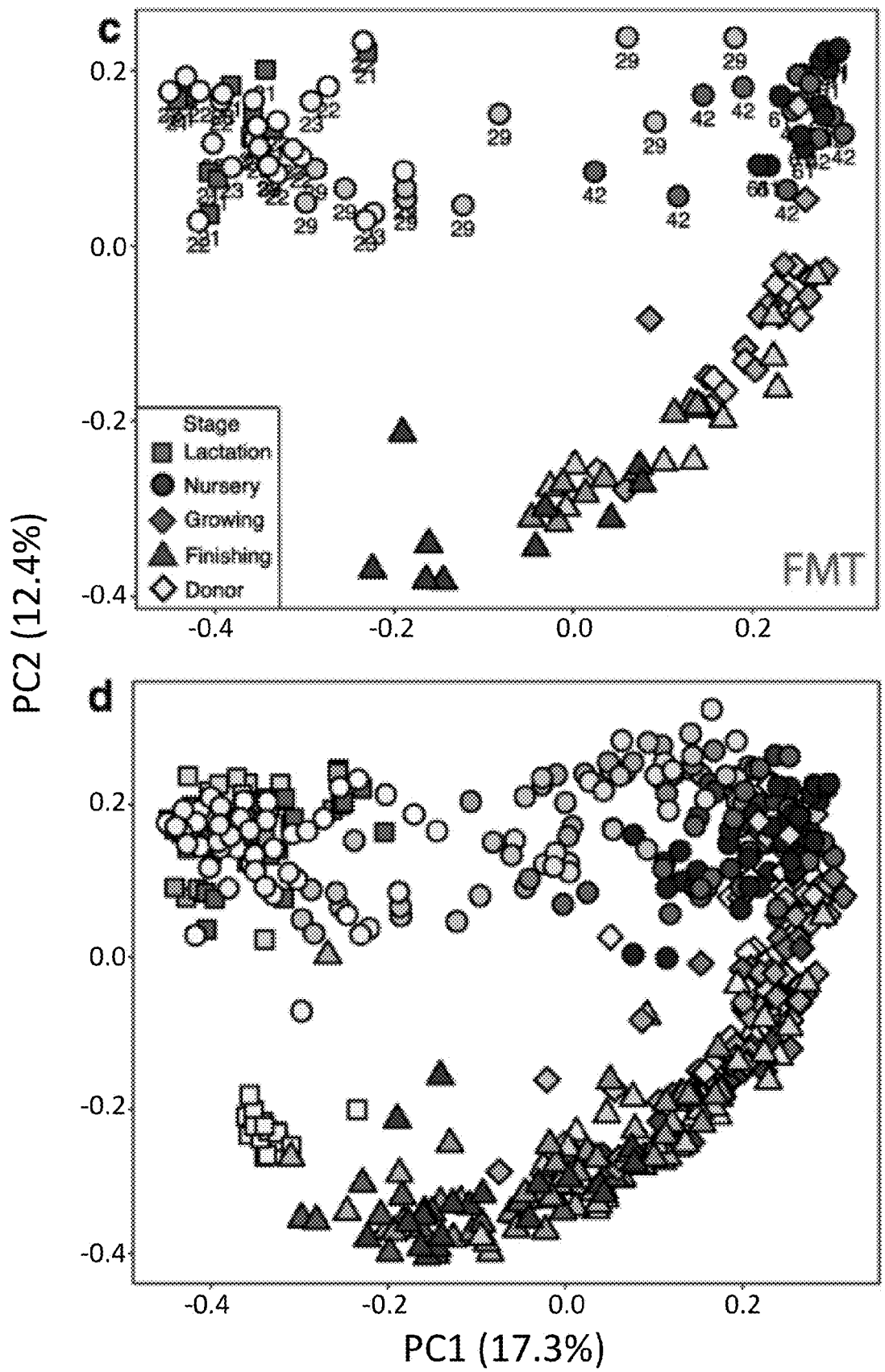
Figure 10:
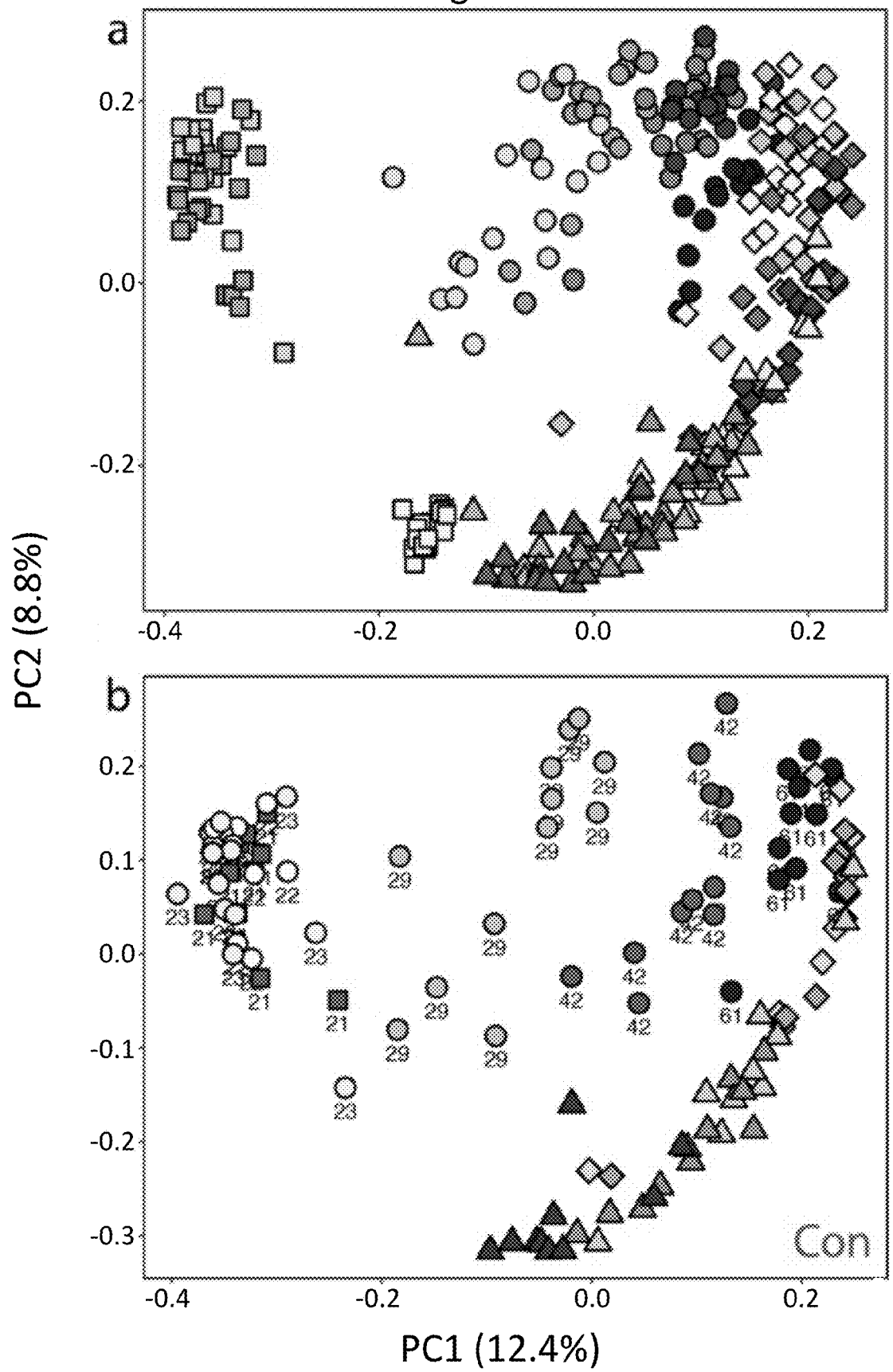
FIG. 10 shows longitudinal changes in the swine gut microbiome structure during different growth stages. Principal coordinate analysis (PCoA) plots based on Jaccard distances showed distinct clusters in the test trial (a), the control group (b), the FMT group of the validation trial (c), and all the samples from the three groups combined (d). Lactation, nursery, growing, and finishing stages are labeled by colors (blue, purple, green and red, respectively) and shapes (square, circle, diamond, and triangle, respectively). Samples with same color densities were collected on the same day. The pig donor in the FMT group is indicated with a yellow diamond.
Figure 10:
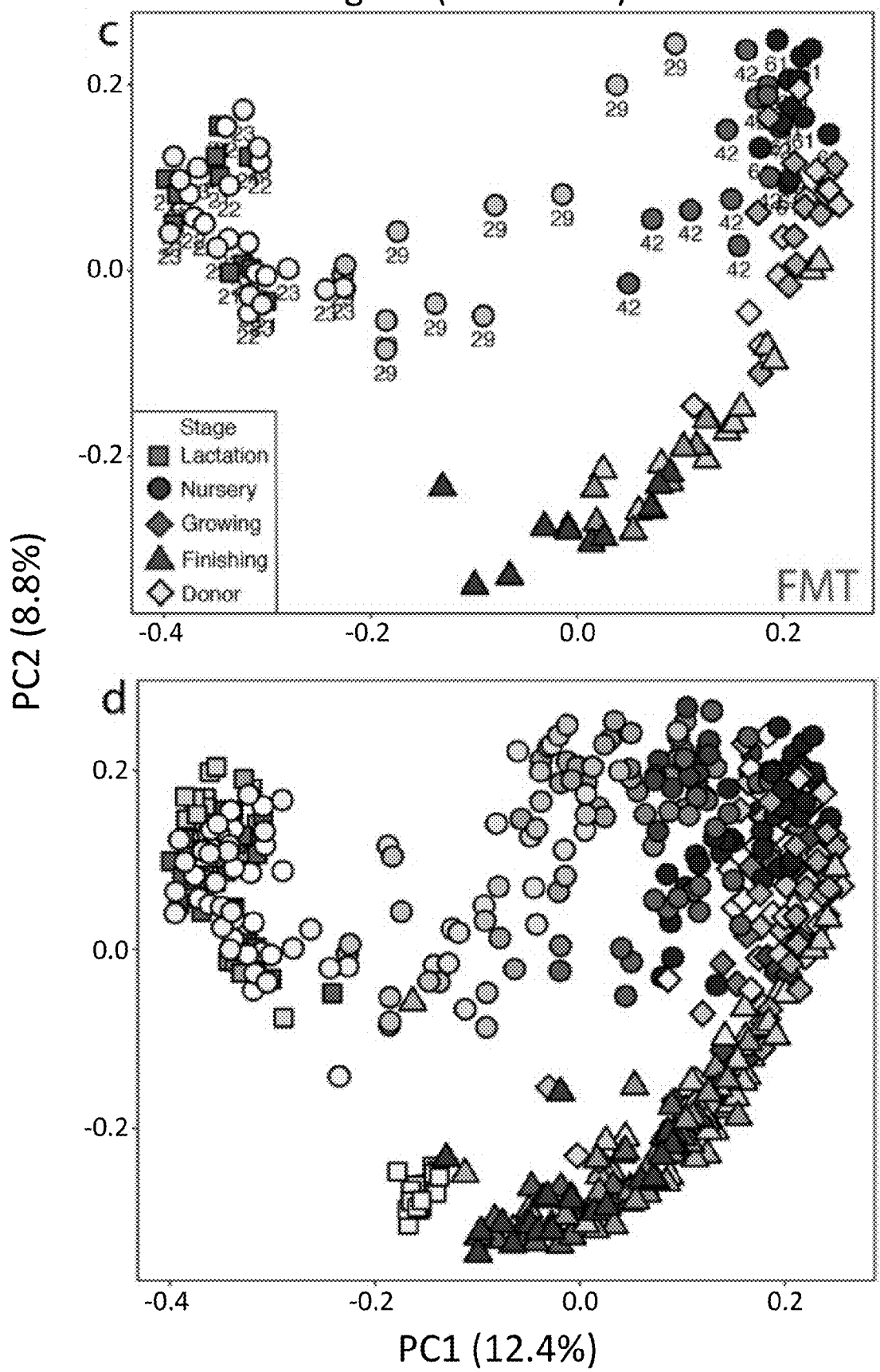

Similar patterns in the development of the gut microbiome were also observed in the validation trial in both the control and the FMT groups. Alpha diversity sustained an increasing trend starting at weaning (d 21) until the end of the finishing stage in both groups (FIG. 1*c-f*). Introduction of solid food did not change the swine gut microbiome immediately. Microbiota on the first two days of the nursery stage (d 22 and 23) were still clustered with those collected from weaning (ANOSIM, R<0.1, P>0.05; Table 5). Significant changes in community structure were observed at the end of nursery phase 1 on d 29 after 8 days of solid feed consumption (Table 5, FIGS. 2*b* and *c*), consistent with animal Trial 1 (FIG. 2*a*). In general, distinct clusters of the swine gut microbiome were observed in both individual animal trials and when combined together (FIG. 2*d* and FIG. 10*d*). Although FMT increased animal growth performance, it did not drastically change the swine gut microbiome (FIG. 13). Only minor changes in swine gut microbiome were observed on d 42 (ANOSIM, R=0.24, P<0.05) and 61 (ANOSIM, R=0.16, P<0.05).

TABLE 5

ANOSIM analysis of changes in the swine gut microbiome structures within the first nursery phase after solid feed supplementation

| Group 1 | Group 2 | Sample size | Permutations | R value | p value |
| --- | --- | --- | --- | --- | --- |
| d21BT | d22BT | 23 | 999 | −0.01 | 0.57 |
| d21BT | d23BT | 24 | 999 | −0.05 | 0.83 |
| d22BT | d23BT | 23 | 999 | −0.03 | 0.66 |
| d21BT | d29BT | 24 | 999 | 0.78* | <0.01* |

Figure 14:
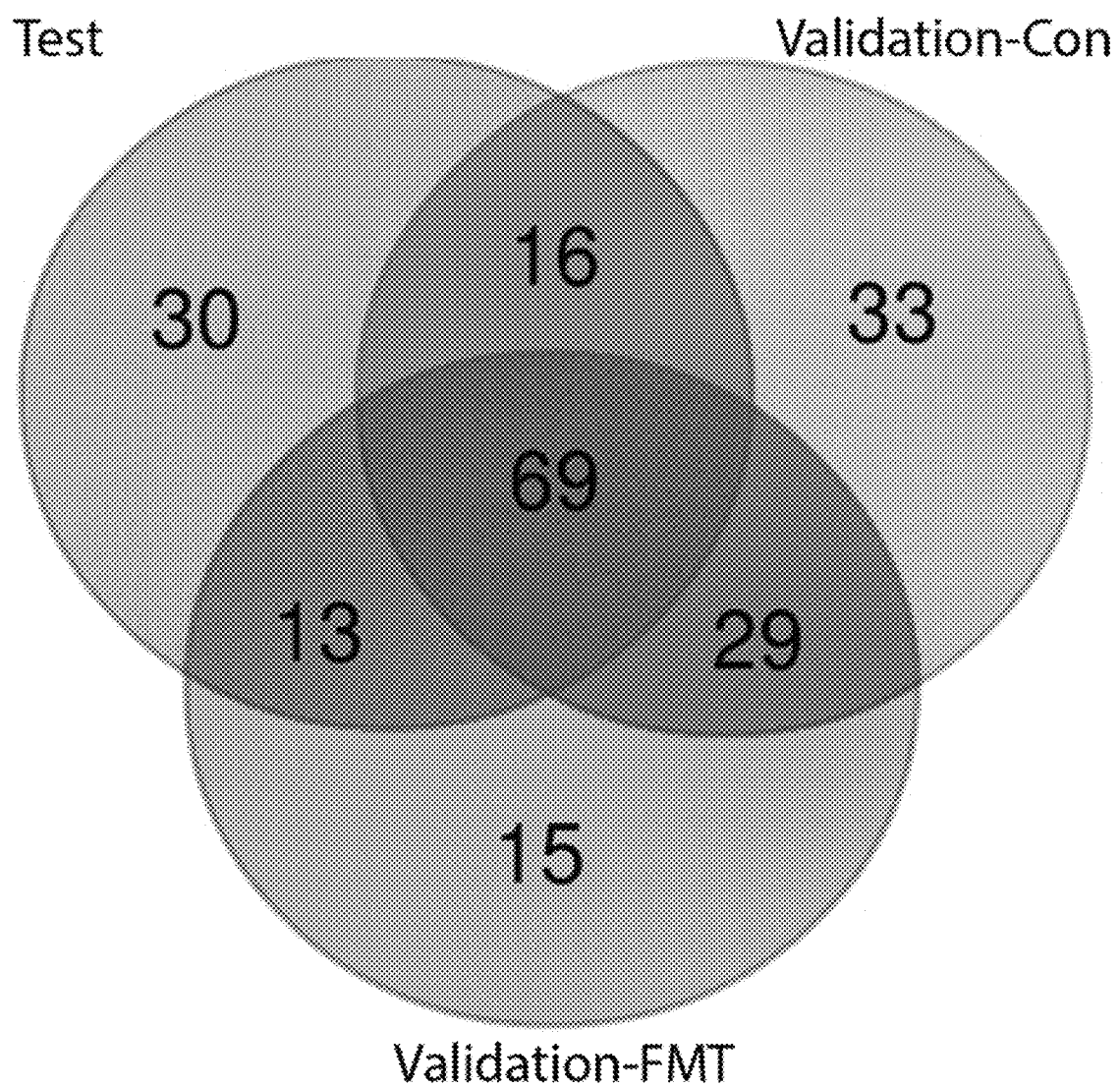
FIG. 14 shows a Venn diagram, which reveals a "core" microbiome, identified as pre-harvest residents shared by the test, validation-Con, and validation-FMT groups.
Figure 15:
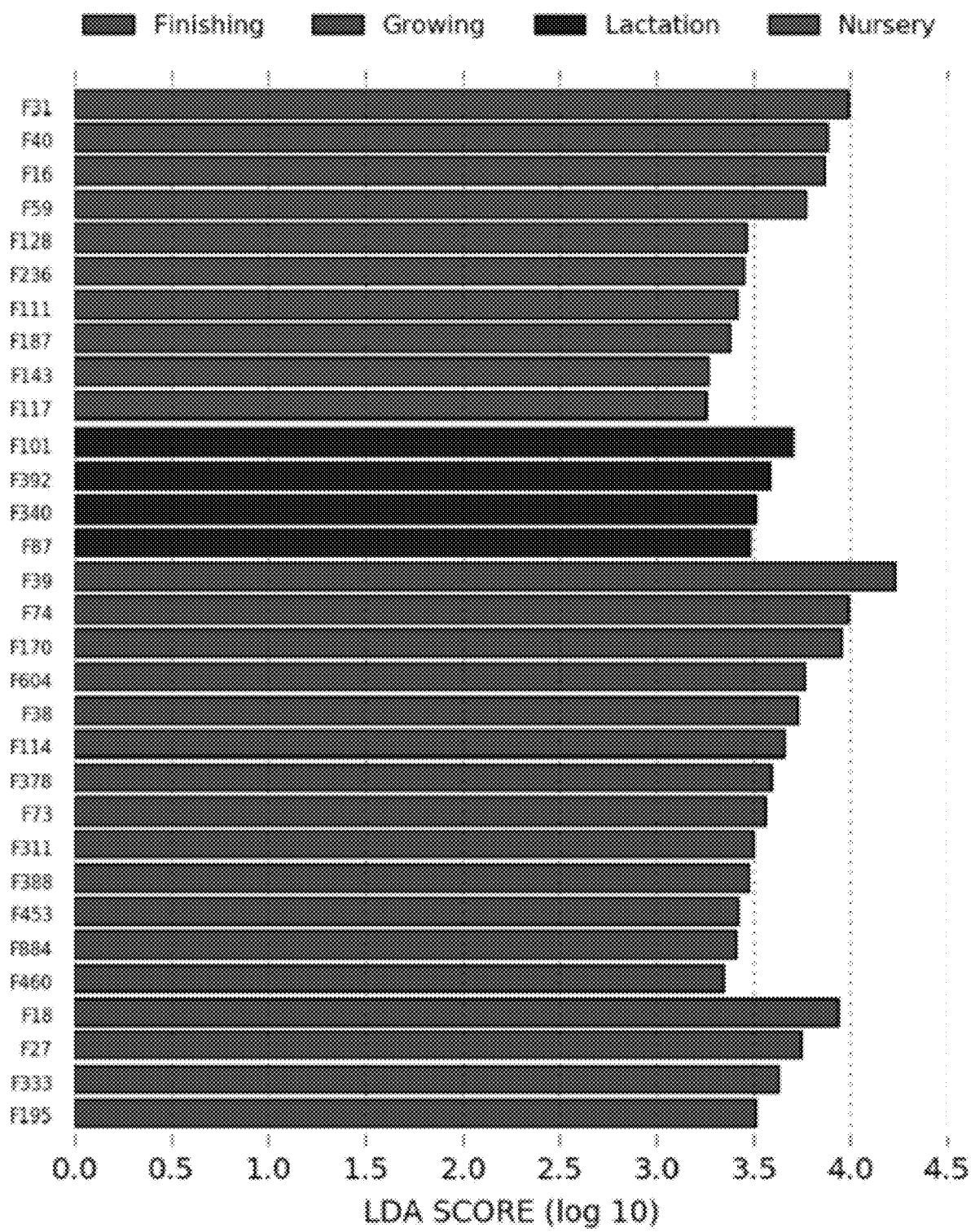
FIG. 15 shows the stage-enriched features identified by LEfSe in control (a) and FMT (b) groups of the validation study based on the top 1000 features (excluding samples from d 22 and 23). The heat maps reflect averaged relative abundances on a log scale of stage-enriched features (LDA>2) in the control (c) and FMT (d) groups with red indicating high abundance and blue indicating low abundance.
Figure 15:
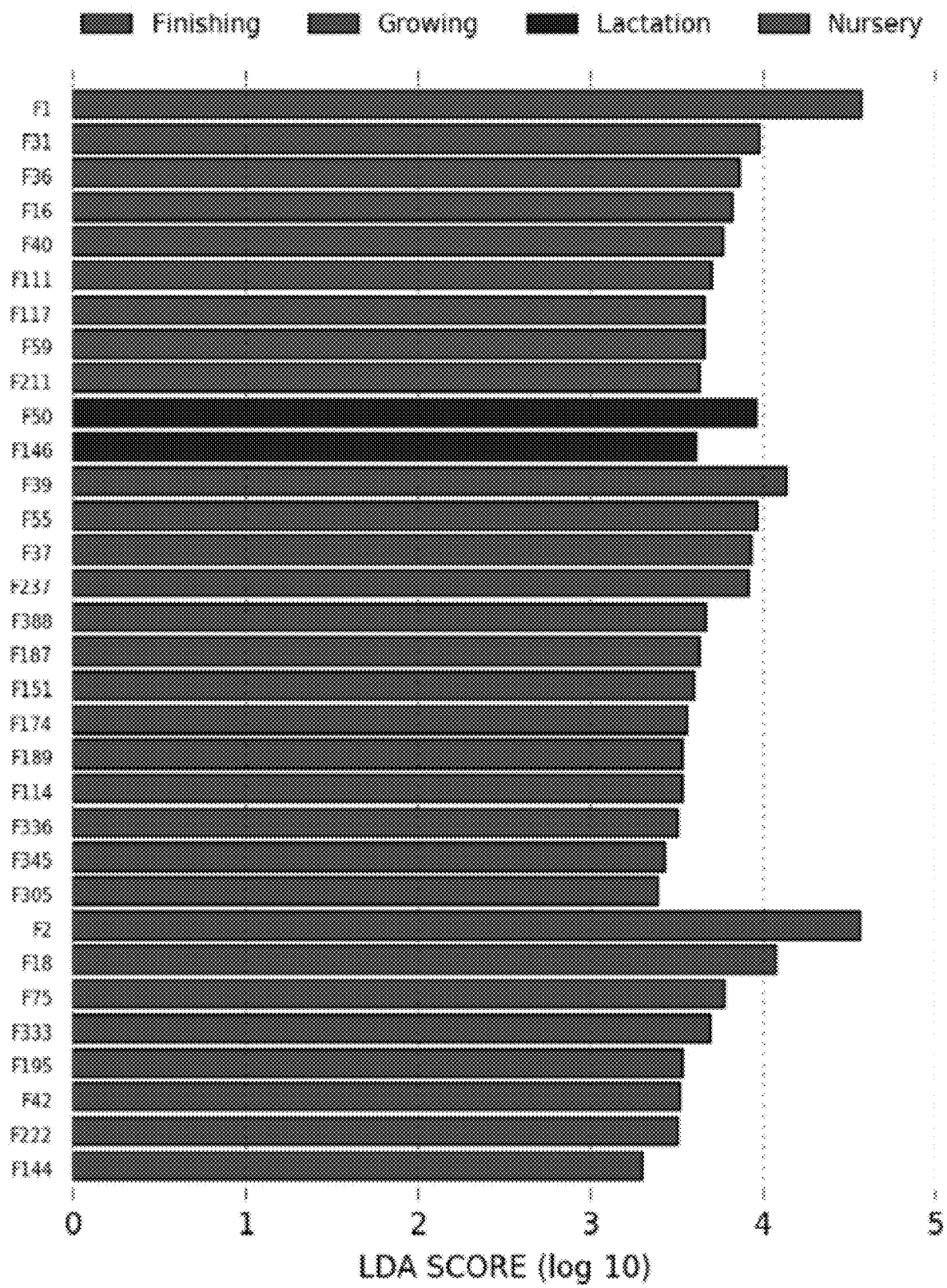
Figure 15:
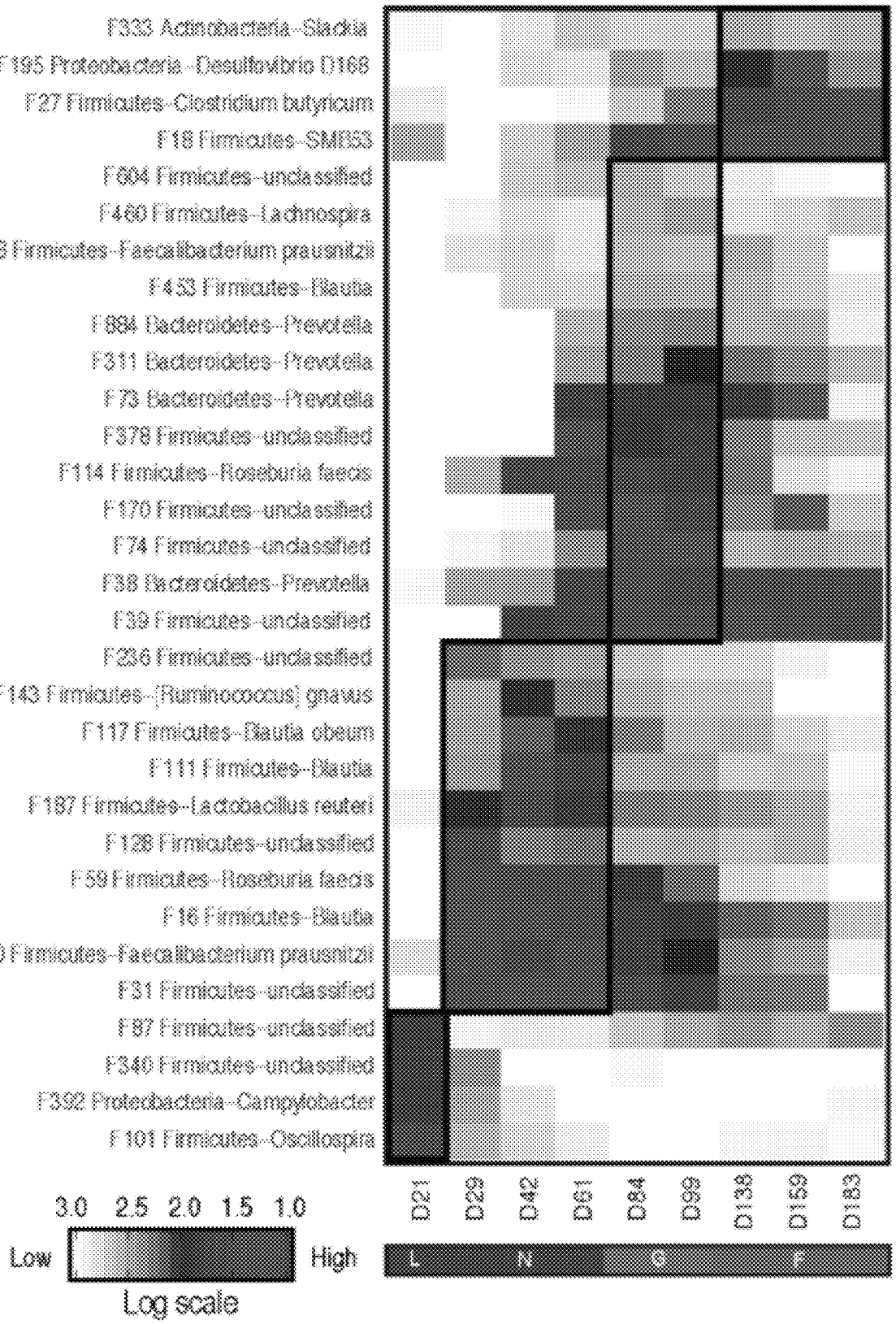
Figure 15:
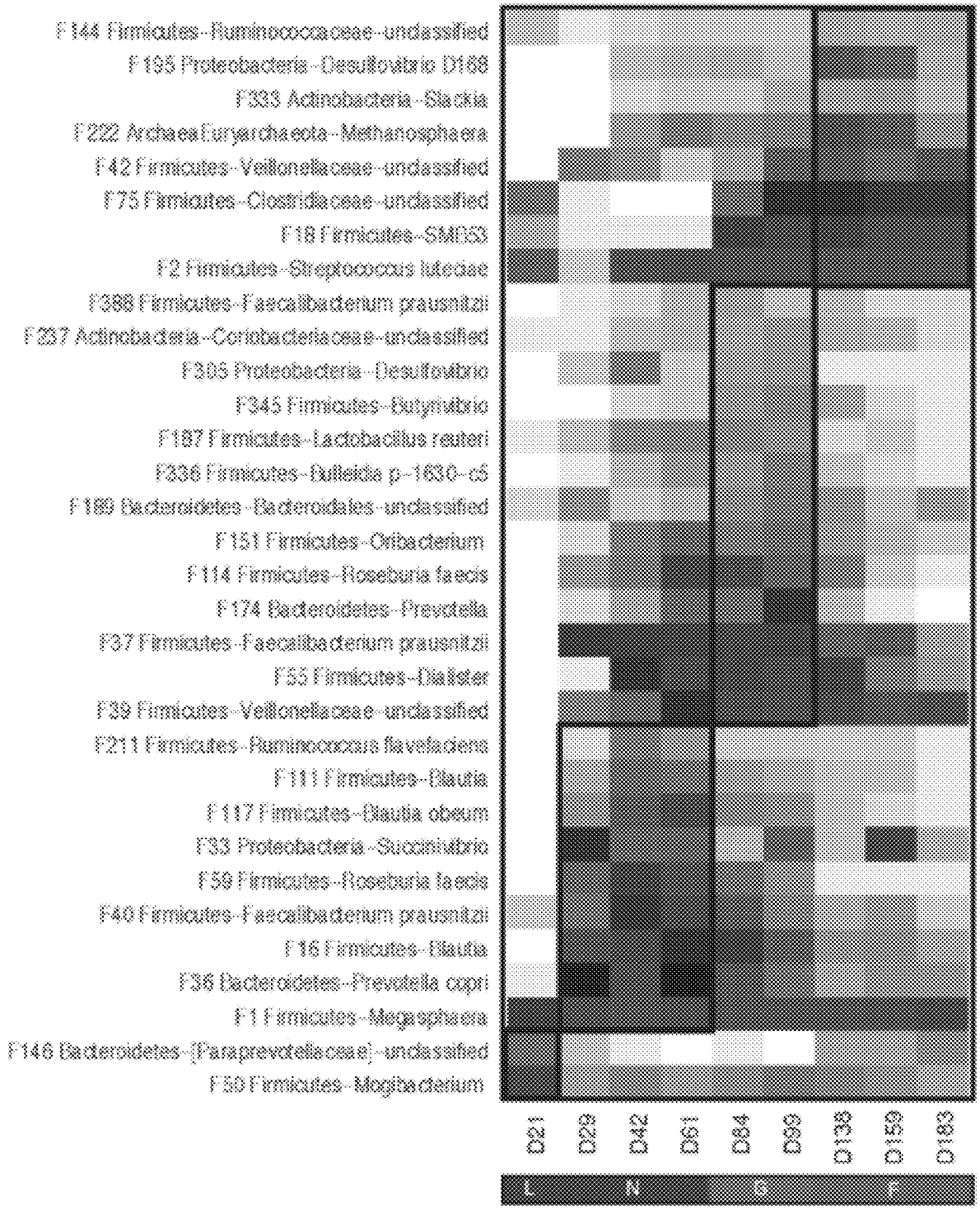

As to the core microbiome, 147 and 125 features were identified from the control and the FMT group in animal trial 2 among the top 700 features, respectively. Moreover, 69 of these core microbiome features were shared among three groups of pigs (Trial 1, Trial2-Control, and Trial2-FMT group (FIG. 14). In addition, both the control (N=31) and the FMT (N=32) groups showed stage-associated swine gut microbiome features in the second trial (FIG. 15) as well. Among these features, two (F87 and F101), six (F16, F40, F59, F117, F128 and F143), four (F170, F114, F388 and F453), and three (F18, F195, and F333) features were shared between test trial and validation control groups at lactation, nursery, growing, and finishing stages, respectively.

Diet Shapes Stage-Specific Swine Gut Microbiome

Permutational multivariate analysis of variance (PERMANOVA) was performed to elucidate the mechanism underlying the assembly of the stage-associated swine gut microbiome. Factors such as age, body weight, diet, gender, individual pigs, and sows were examined. Diet was used as a categorical variable including eight categories: lactation (sow milk), nursery (NP1, NP2, and NP3), growing (GP1 and GP2), and finishing diets (FP1 and FP2) in the test trial. We developed a series of models to determine the most important factors shaping the swine gut microbiome. We first performed PERMANOVA using univariate models. Diet, age, and body weight were all significant factors shaping the swine gut microbiome, with about 35% variation attributed to diet. Variability in individual pigs (PigID) also explained about 12% of variation in the swine gut microbiome, whereas gender and sows had little effect on the swine gut microbiome (Table 6a). Given that age and body weight were highly correlated, we excluded BW in subsequent multivariate models. Diet was the most important factor in the multivariate model, with F value of 22.2 explaining about 35% of variation (Table 6b).

In another multivariate model to determine which nutrients in the diet contributed most to the swine gut microbiome, we broke down the diets into different components including neutral detergent fiber (NDF), crude fiber, crude protein, and crude fat (Table 6c). Since we did not measure the nutrients in sow milk, we excluded the lactation samples from subsequent models. Diet was still the most important variable in the new model, explaining about 34% of the variation (Table 7a). NDF was the most important dietary nutrient in shaping the swine gut microbiome. Specifically, NDF from corn had the strongest effect with a pseudo F value of 66 explaining about 19% of the variation, followed by NDF from soybean (F=20, $R^2$=0.06) and DDGS (F=10, $R^2$=0.03) (Table 7b).

TABLE 6

PERMANOVA analysis of the factors affecting the swine gut microbiome. Data were analyzed using the R program Vegan package. All 16 time points from d 0 to 174 in the test study were used to perform PERMANOVA analysis with univariate models (a) and multivariate model (b) with a sequential order of diet, age, gender, sow origin and PigID. Diet composition was listed in (c).

a.

|  | DF | SumsofSquares | MeanSq | F.Model | $R^2$ | P | Residuals |
|---|---|---|---|---|---|---|---|
| Diet | 7 | 28.162 | 4.023 | 20.518 | 0.354 | 0.001 | 0.646 |
| Age | 1 | 8.969 | 8.969 | 34.065 | 0.113 | 0.001 | 0.887 |
| Bodyweight | 1 | 8.488 | 8.488 | 32.331 | 0.114 | 0.001 | 0.886 |
| Gender | 1 | 0.226 | 0.226 | 0.764 | 0.003 | 0.725 | 0.997 |
| PigID | 17 | 5.245 | 0.309 | 1.047 | 0.066 | 0.313 | 0.934 |
| Sow | 2 | 0.862 | 0.431 | 1.4635 | 0.011 | 0.049 | 0.989 | b.

|  | Df | SumsOfSqs | MeanSqs | F.Model | $R^2$ | Pr(>F) |
|---|---|---|---|---|---|---|
| Diet | 7 | 28.162 | 4.023 | 21.970 | 0.354 | 0.001 |
| Age | 1 | 1.353 | 1.353 | 7.390 | 0.017 | 0.001 |
| Gender | 1 | 0.206 | 0.206 | 1.127 | 0.003 | 0.245 |
| Sow | 1 | 0.380 | 0.380 | 2.074 | 0.005 | 0.021 |
| PigID | 16 | 4.936 | 0.309 | 1.685 | 0.062 | 0.001 |
| Residuals | 243 | 44.497 | 0.183 | 0.560 |  |  | c.

|  | NP 1 | NP 2 | NP 3 | GP[1] 1 | GP 2 | FP[1] 1 | FP 2 |
|---|---|---|---|---|---|---|---|
| Ingredients, % of total diet |  |  |  |  |  |  |  |
| Corn | 38.8 | 44.4 | 47.4 | 61.72 | 68.92 | 73.17 | 75.82 |
| Soybean meal, 48% | 25 | 31.6 | 31.6 | 20.75 | 13.6 | 9.6 | 7 |
| Corn DDGS, >6 and <9% Oil | 0 | 15 | 15 | 15 | 15 | 15 | 15 |
| Chemical composition |  |  |  |  |  |  |  |
| Total CP (%) | 22.9 | 25.4 | 23.6 | 19.6 | 16.7 | 15.1 | 14.1 |
| Crude fat (%) | 5.4 | 6.6 | 6.5 | 3.8 | 3.9 | 4 | 4.1 |
| Crude fiber (%) | 1.8 | 3.5 | 3.5 | 3.4 | 3.2 | 3.2 | 3.1 |
| NDF[2](%) | 5.6 | 11.2 | 11.5 | 11.9 | 12 | 12 | 12.1 |
| NDF from Corn, % | 3.5 | 4.1 | 4.3 | 5.6 | 6.3 | 6.7 | 6.9 |

[1]NP: nursery phase;
GP: growing phase;
FP: finishing phase.
[2]NDF: neutral detergent fiber

TABLE 7

PERMANOVA analysis of the factors affecting the swine gut microbiome (multivariate models). Data were analyzed using R program Vegan package. Samples from nursery, growing and finishing stages in the test study were used to perform PERMANOVA analysis with two sequential orders: diet, age, gender, sow origin and PigID (a); NDF, crude fiber, crude protein, and crude fat, age, sow origin and pig ID (b).

(a)

|  | Df | SumsOfSqs | MeanSqs | F | R2 | P | Residuals |
|---|---|---|---|---|---|---|---|
| Diet | 6 | 17.17 | 2.86 | 19.07 | 0.34 | 0.001 | 0.57 |
| Age | 1 | 0.48 | 0.48 | 3.7 | 0.01 | 0.004 |  |
| Gender | 1 | 0.23 | 0.23 | 1.52 | 0 | 0.113 |  |
| Sow | 2 | 0.64 | 0.32 | 2.13 | 0.01 | 0.006 |  |
| PigID | 13 | 3.68 | 0.28 | 1.89 | 0.07 | 0.001 |  |

TABLE 7-continued

PERMANOVA analysis of the factors affecting the swine gut microbiome (multivariate models). Data were analyzed using R program Vegan package. Samples from nursery, growing and finishing stages in the test study were used to perform PERMANOVA analysis with two sequential orders: diet, age, gender, sow origin and PigID (a); NDF, crude fiber, crude protein, and crude fat, age, sow origin and pig ID (b).

(b)

| | Df | SumsOfSqs | MeanSqs | F | R2 | Pr (>F) |
|---|---|---|---|---|---|---|
| Corn NDF | 1 | 9.9 | 9.9 | 65.97 | 0.19 | 0.001 |
| soybean NDF | 1 | 3.02 | 3.02 | 20.1 | 0.06 | 0.001 |
| DDGS NDF | 1 | 1.57 | 1.57 | 10.47 | 0.03 | 0.001 |
| Crude fiber | 1 | 1.45 | 1.45 | 9.67 | 0.03 | 0.001 |
| Crude protein | 1 | 0.3 | 0.3 | 2 | 0.01 | 0.037 |
| Crude fat | 1 | 0.93 | 0.93 | 6.22 | 0.02 | 0.001 |
| Age | 1 | 0.48 | 0.48 | 3.2 | 0.01 | 0.003 |
| Sow | 2 | 0.67 | 0.33 | 2.22 | 0.01 | 0.003 |
| PigID (strata) | 14 | 3.88 | 0.28 | 1.85 | 0.08 | 0.001 |
| Residuals | 193 | 28.96 | 0.15 | 0.57 | | |
| Total | 216 | 51.16 | 1 | | | |

Figure 16:
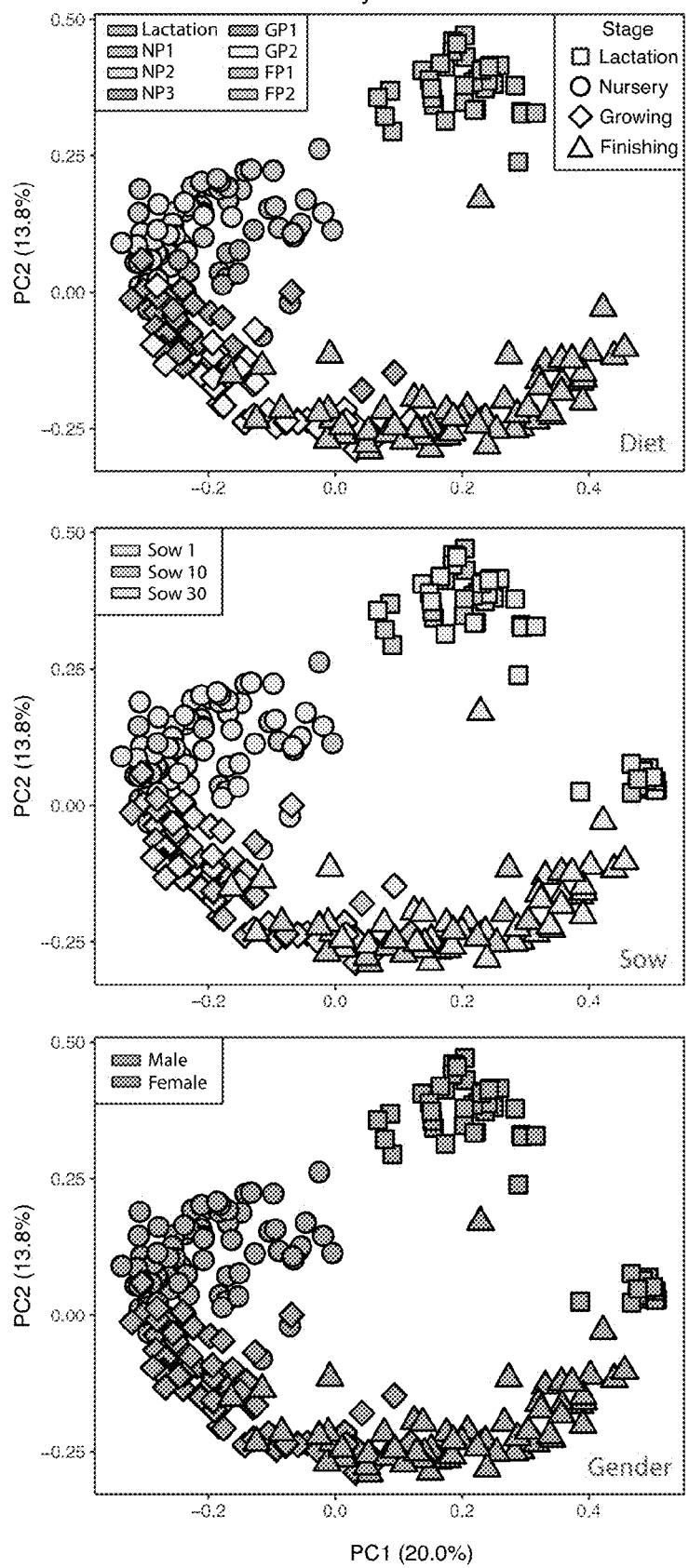
FIG. 16 shows PCoA plots of longitudinal gut microbiome community in the test trial, distinguished by diet, sow and gender. Lactation, nursery, growing and finishing stages are distinguished by shape (square, circle, diamond, and triangle, respectively).
Figure 17:
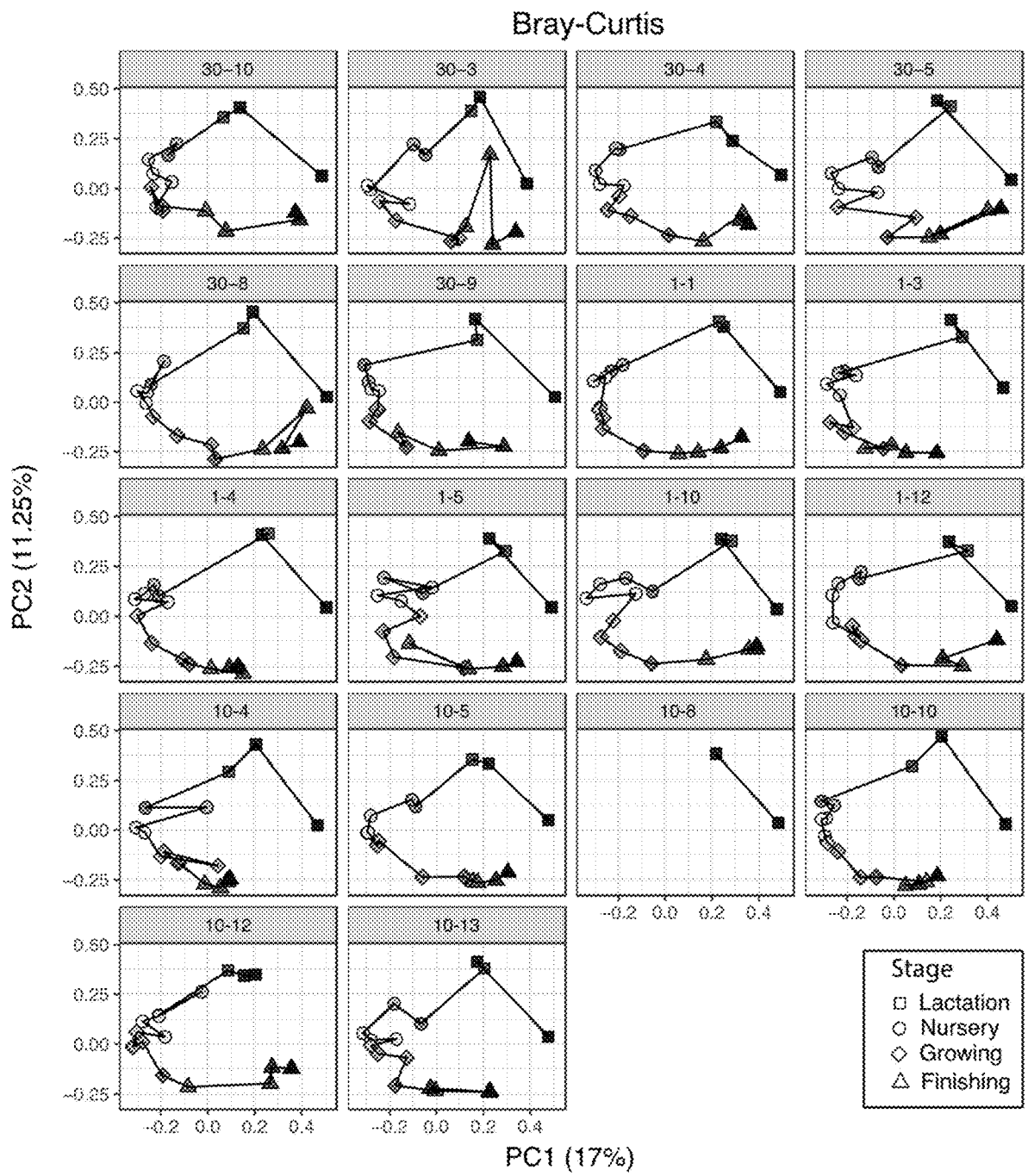
FIG. 17 shows PCoA plots (Bray-Curtis) of longitudinal gut microbiome for individual pigs with their ear notch number shown on each plot. Lactation, nursery, growing, and finishing stages were distinguished by shape (square, circle, diamond, and triangle, respectively). Samples with same color densities were collected on the same day. Missing data or samples from d 0 for certain pigs are not shown.

Consistently, PCoA plot also shows the effect of these factors on the swine gut microbiome. Eight distinct clusters on the PCoA plot based on the Bray-Curtis distance assembled according to diet. No obvious clustering according to gender or sow was observed on the PCoA plots (FIG. 16). Although general succession patterns in the gut microbiome were observed in individual pigs, remarkable inter-pig differences in community structures were demonstrated at different stages (FIG. 17).

Figure 18:
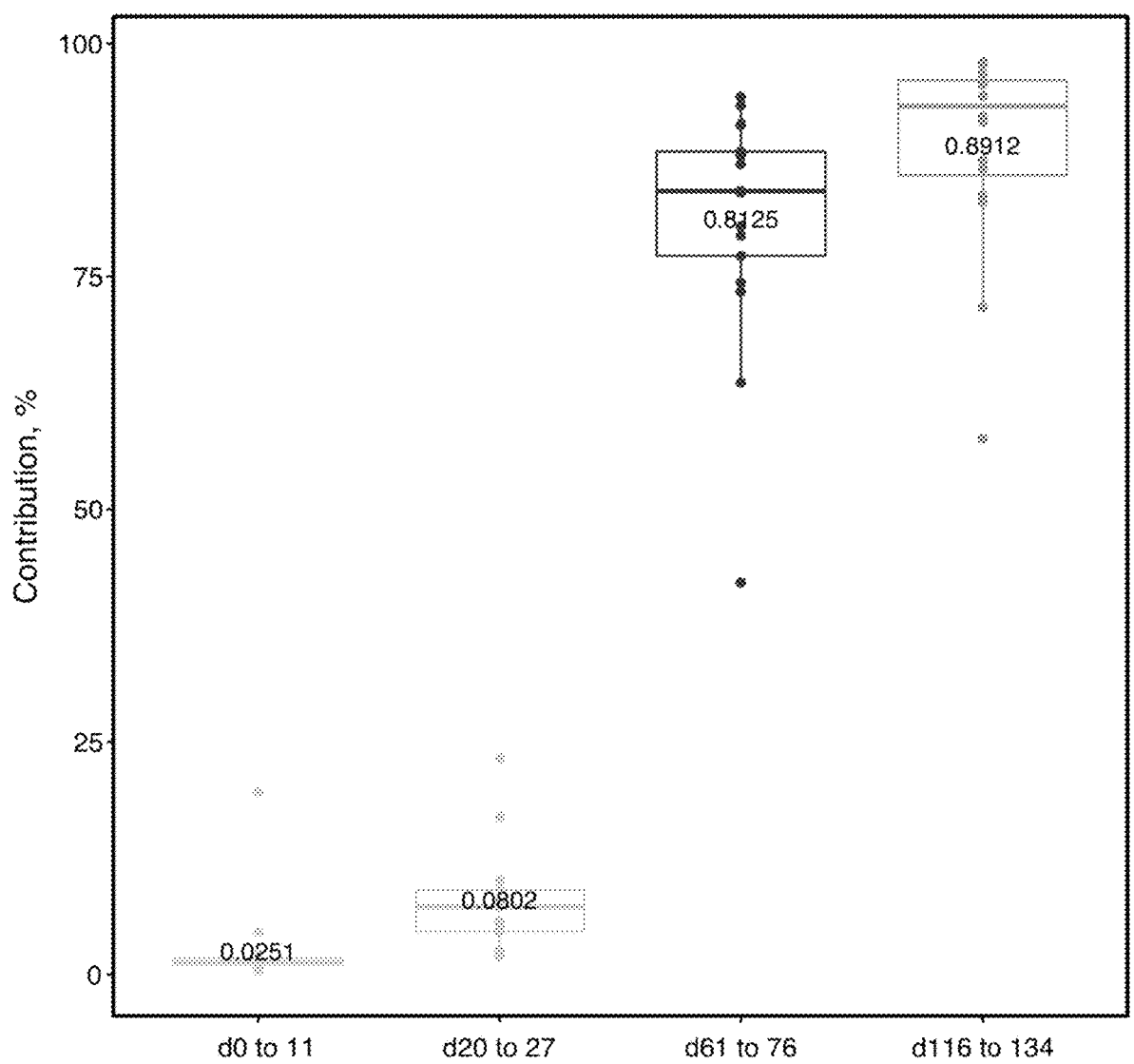
FIG. 18 shows a SourceTracker analysis of the contributions of the early-stage gut microbiome to the later-stage ones. The four box plots show the percentage of contribution from the d 0 sample to d 11 (lactation), d 20 (weaning) to d 27 (nursery phase 1), d 61 (end of nursery) to d 76 (growing phase 1), and d 116 (end of growing phase 2) to d 134 (finishing phase 1).

In addition, to assess whether priority effects, i.e., the order and timing of species arrival, play any roles in the assembly of the swine gut microbiota, we performed source-tracker to measure the contribution of the early stage microbiome members to the later stage ones. A very small percentage of the swine gut microbiome was derived from early time points; only 3% of the lactation stage microbiome originated from the d 0 samples. Furthermore, the lactation stage microbiomes only contributed 8% to the nursery stage gut microbiome when the pigs were introduced solid feed. On the contrary, a remarkable percentage of the later stage microbiome originated from the nursery and growing stage microbiome when solid feed were consumed. The growing stage microbiome contributed 89% to the subsequent finishing stage, whereas 81% of its members originated from the nursery stage (FIG. 18).

Growth Performance-Associated Bacterial Taxa within Each Stage

Figure 8:
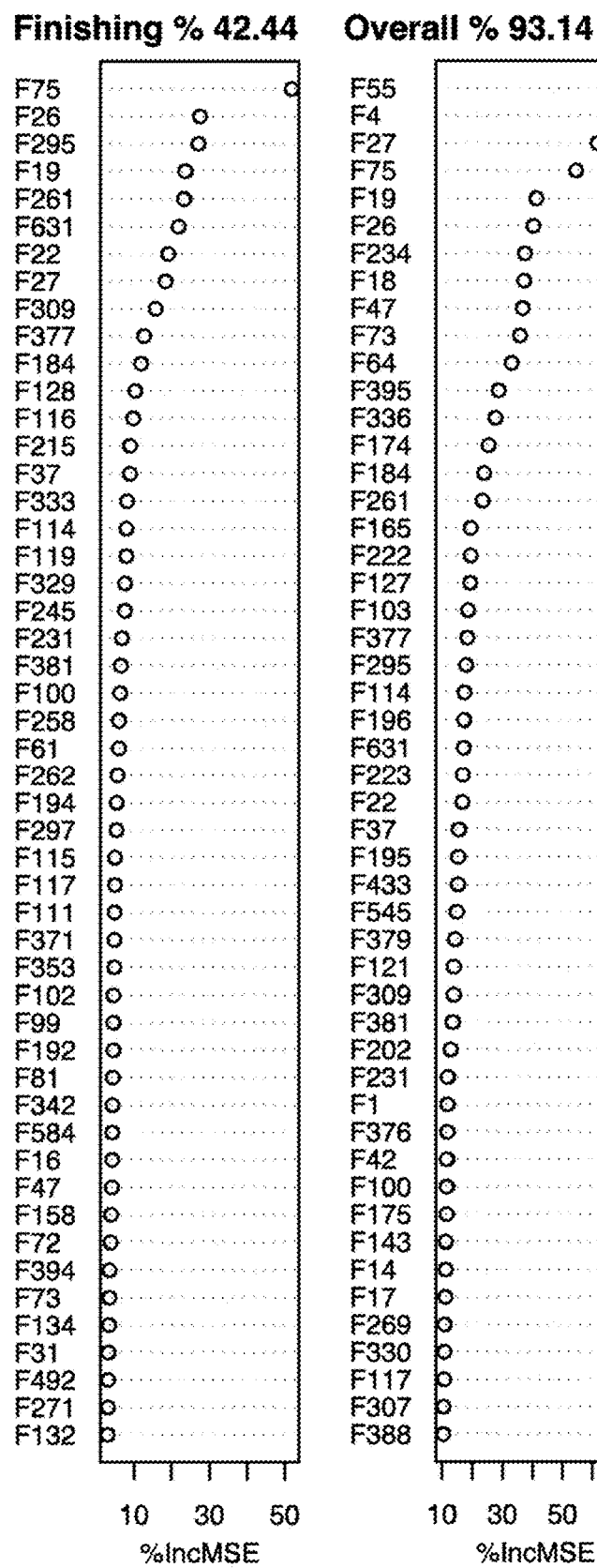
FIG. 8 shows the growth performance-related features identified in the test trial. The top 50 growth-related bacteria identified at the lactation, nursery, growing, and finishing stages are shown. The final column shows the top 50 features across stages (Overall). The top 50 features were selected from the top 500 features for each stage (lactation, nursery, growing, and finishing) or across stages (Overall) using regression-based Random forest algorithm in R.

We next sought to identify growth performance-associated bacterial taxa to be used as potential probiotics. To this end, we first performed regression-based random forest by using body weight (BW) as the outcome and the top 500 bacterial features as predictors for each growth stage in the test trial. The top 50 bacterial features that predict growth performance at each stage are listed in FIG. 8. These features include members of both core and stage-specific microbiomes. For example, F1 and F2 were listed as growth performance-related features at the lactation and nursery stages, whereas F4 was a growing stage bacterium. Feature 27 (*Clostridium butyricum*), a butyric acid producer, together with F4 and F26 were positively correlated with BW at the growing and finishing stages (except on d 146). In addition, F18 and F19 were positively correlated with BW in older pigs (d 90-174 and d 116-174, respectively).

Figure 19:
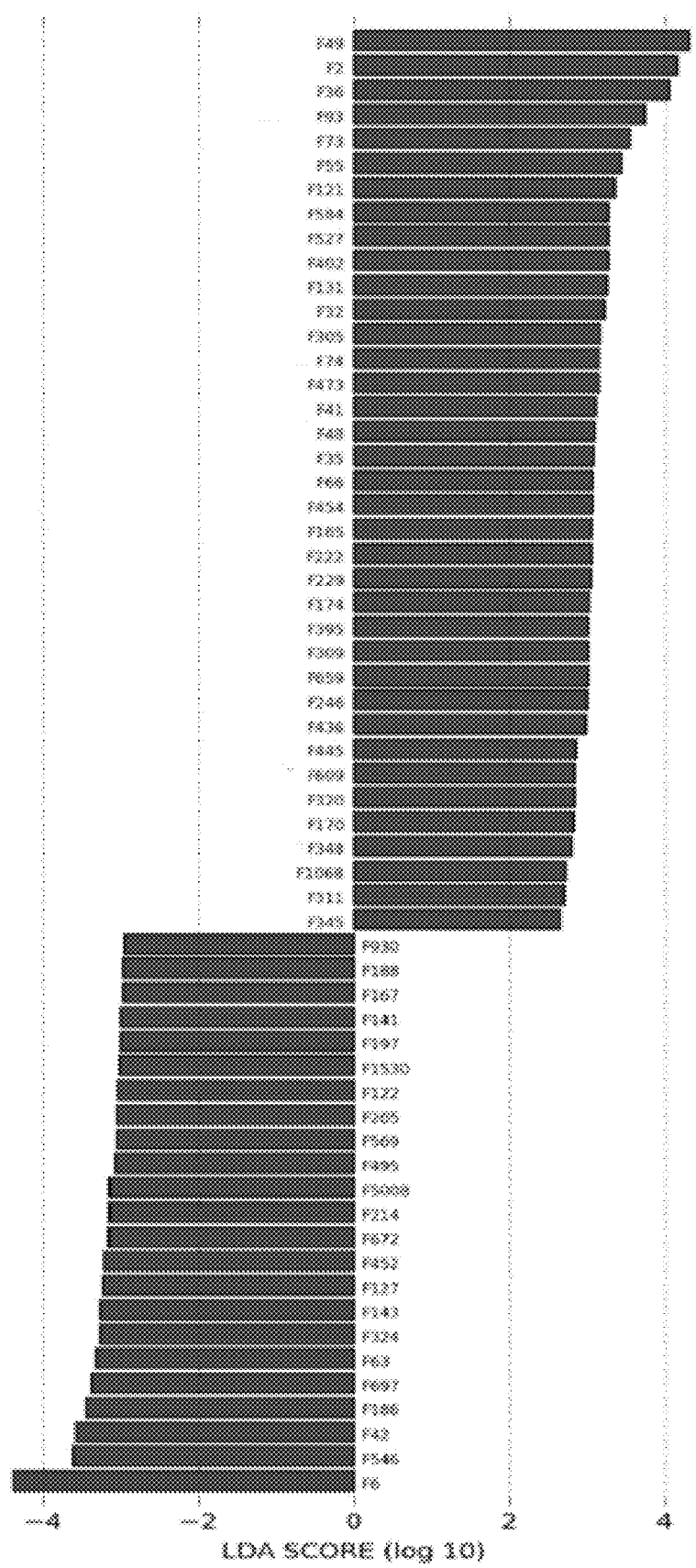
FIG. 19 shows features identified by LEfSe to be differentially represented between the control and the fecal microbiota transplantation (FMT) group in the validation trial on d 42 (a) and d 61 (b), as well as (c) the relative abundances of Feature 2 (right Y axis) and body weight (left Y axis) in the control (light) and the FMT (dark) groups at different time points.
Figure 19:
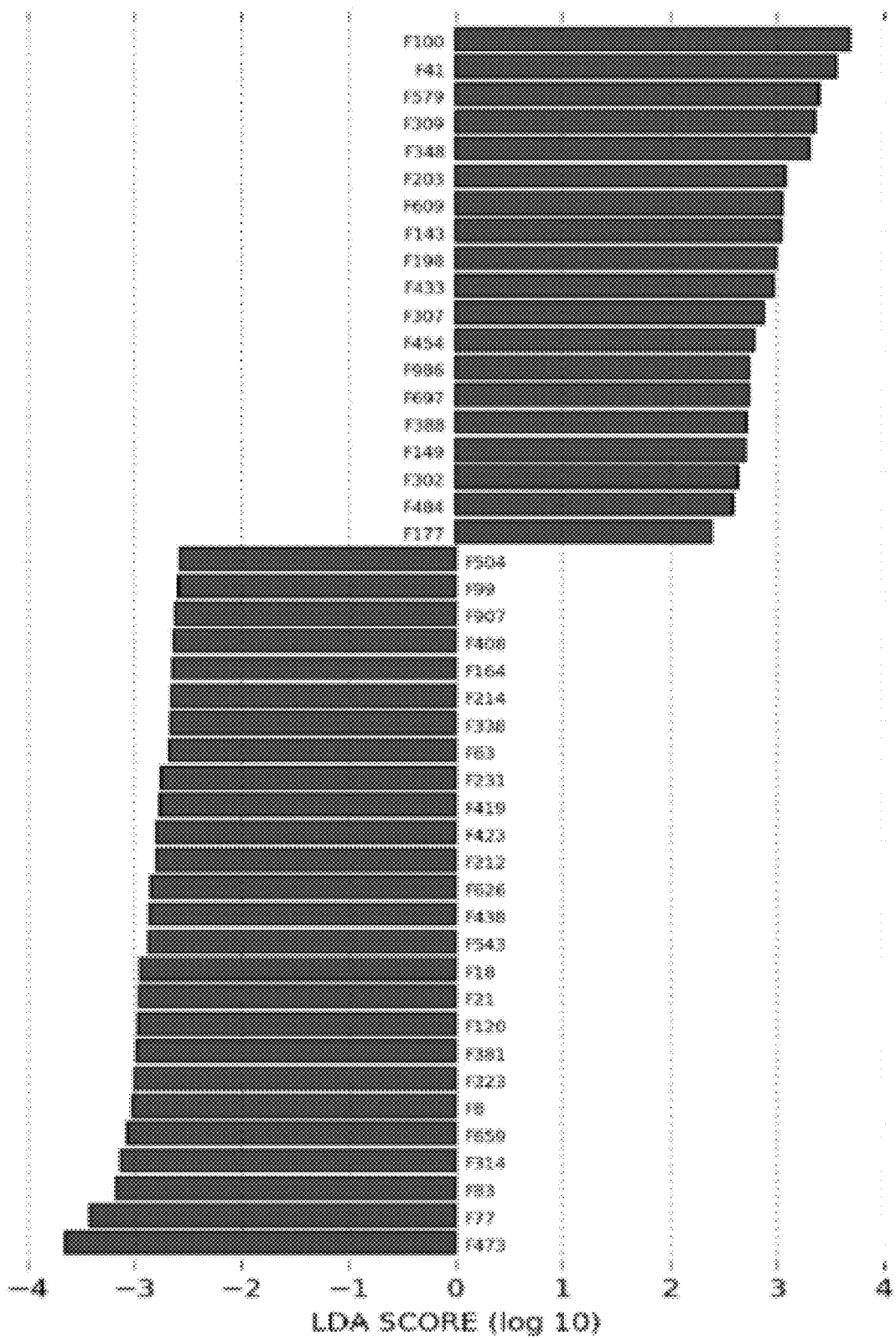
Figure 19:
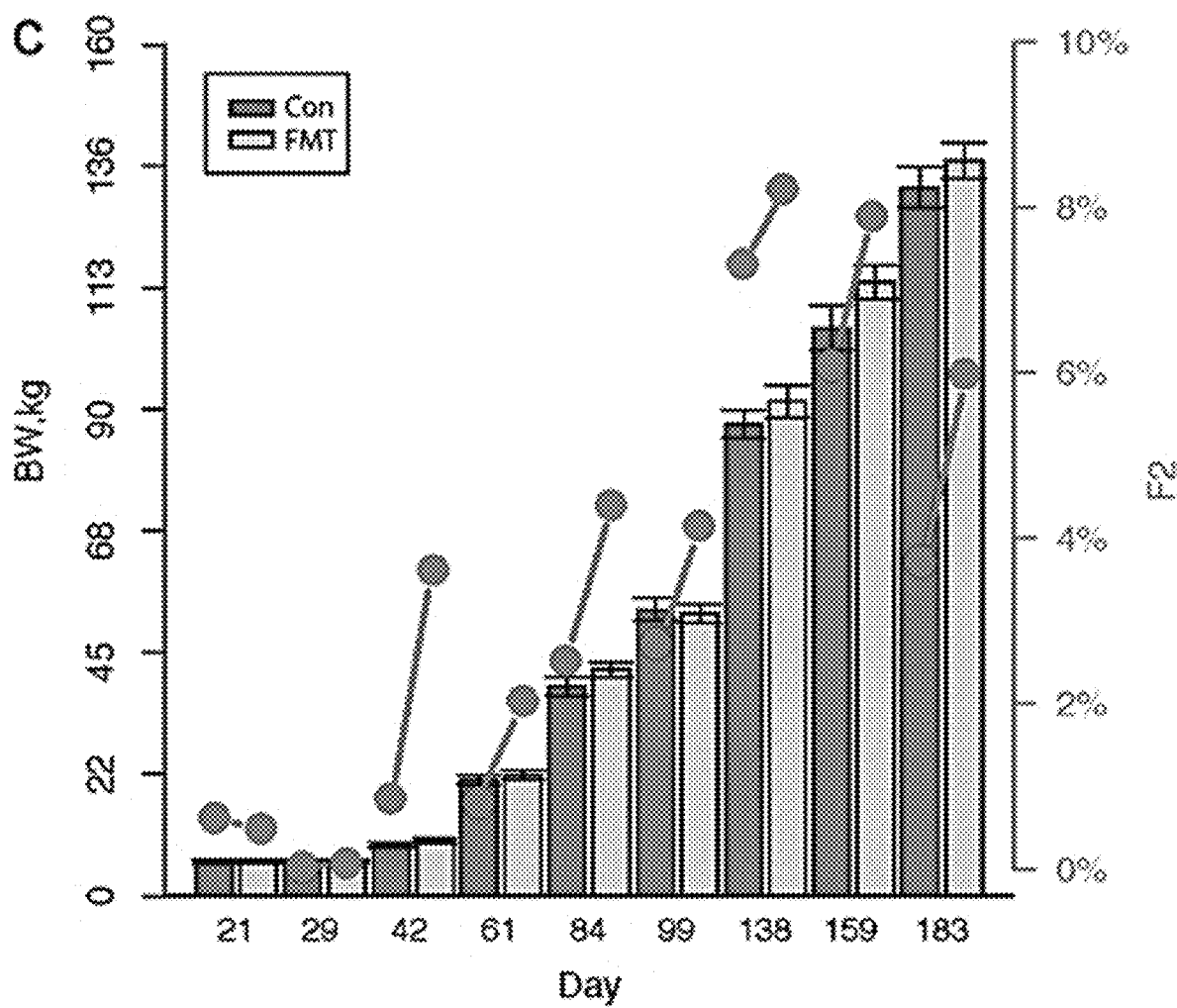
Figure 20:
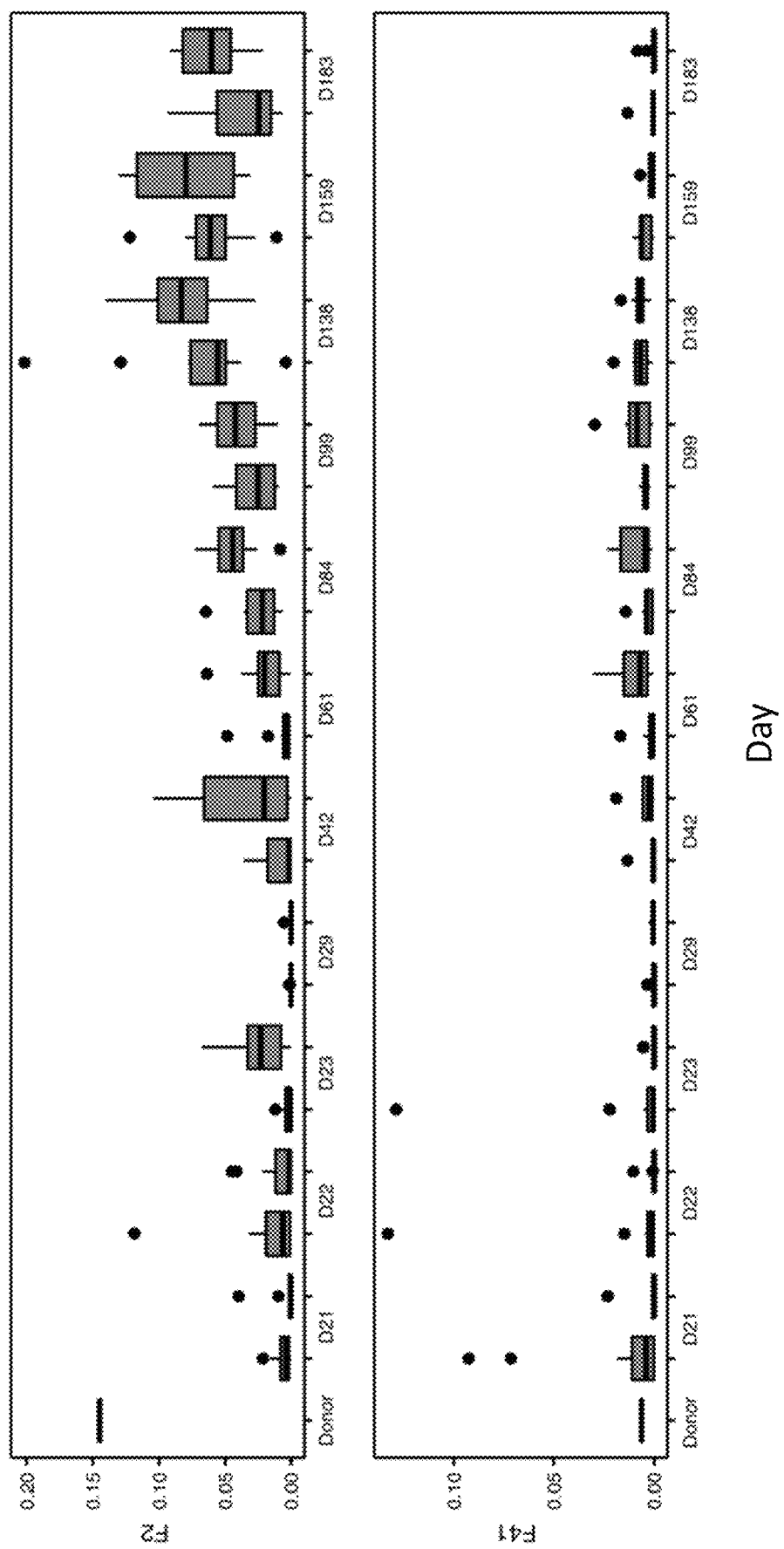
FIG. 20 shows bacterial taxa enriched in the fecal microbiota transplantation (FMT) group at different time points in the validation trial. For each time point, left bars represent the relative abundance of these bacterial features in the control group and right bars represent the relative abundance of these bacterial features in the FMT group.
Figure 20:
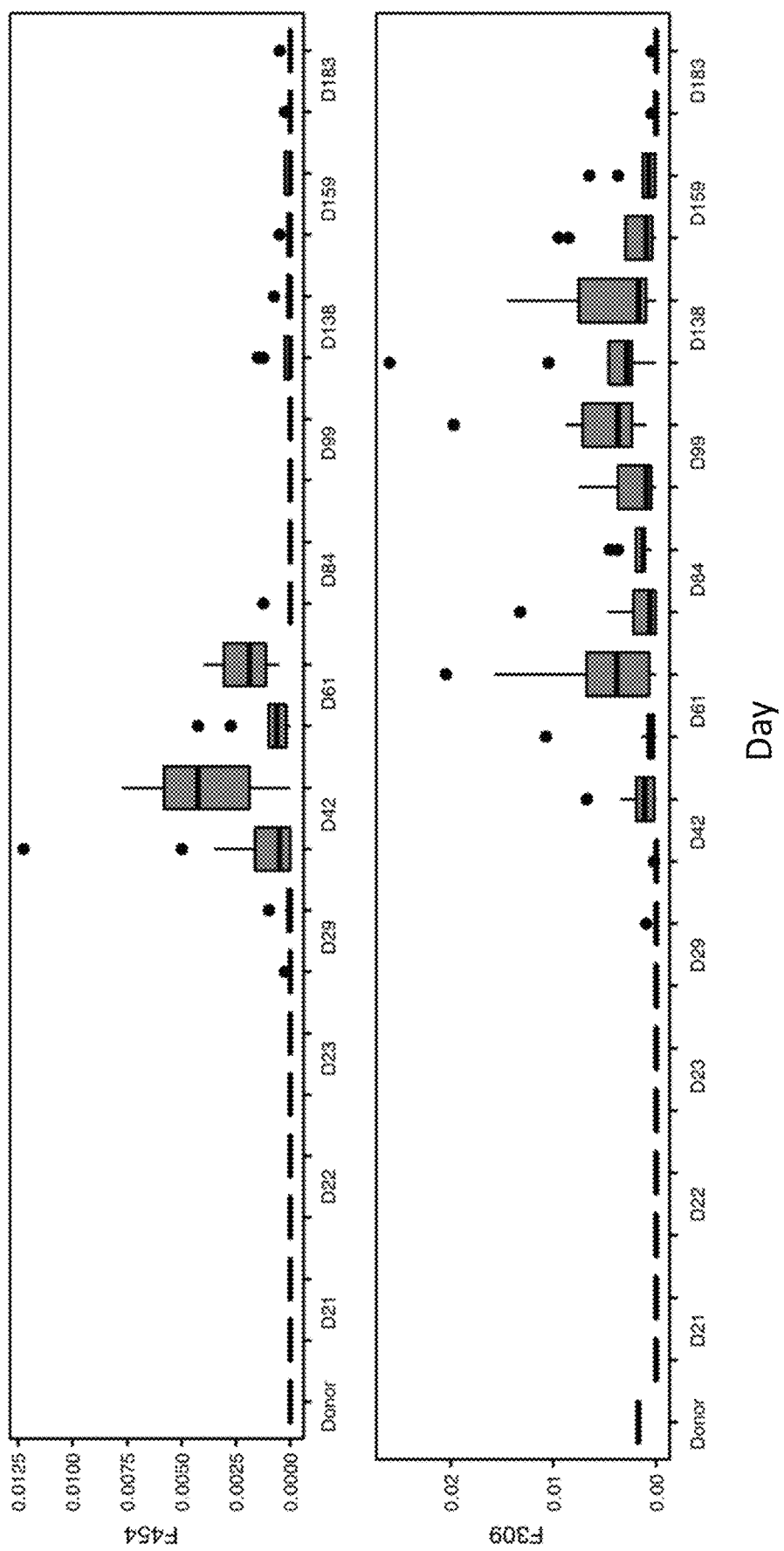
Figure 20:
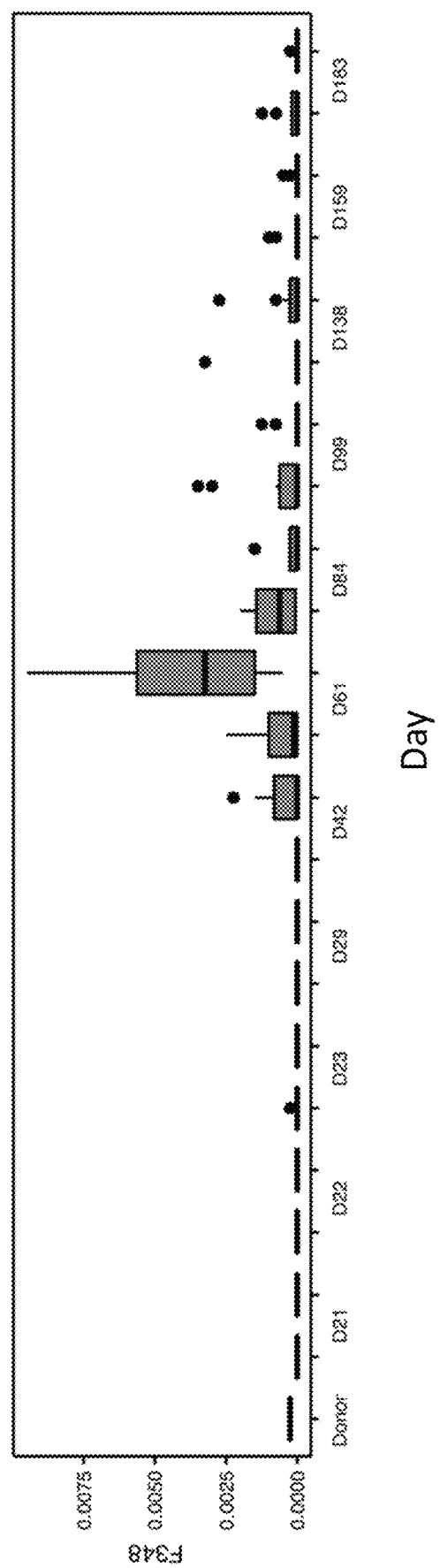
Figure 21:
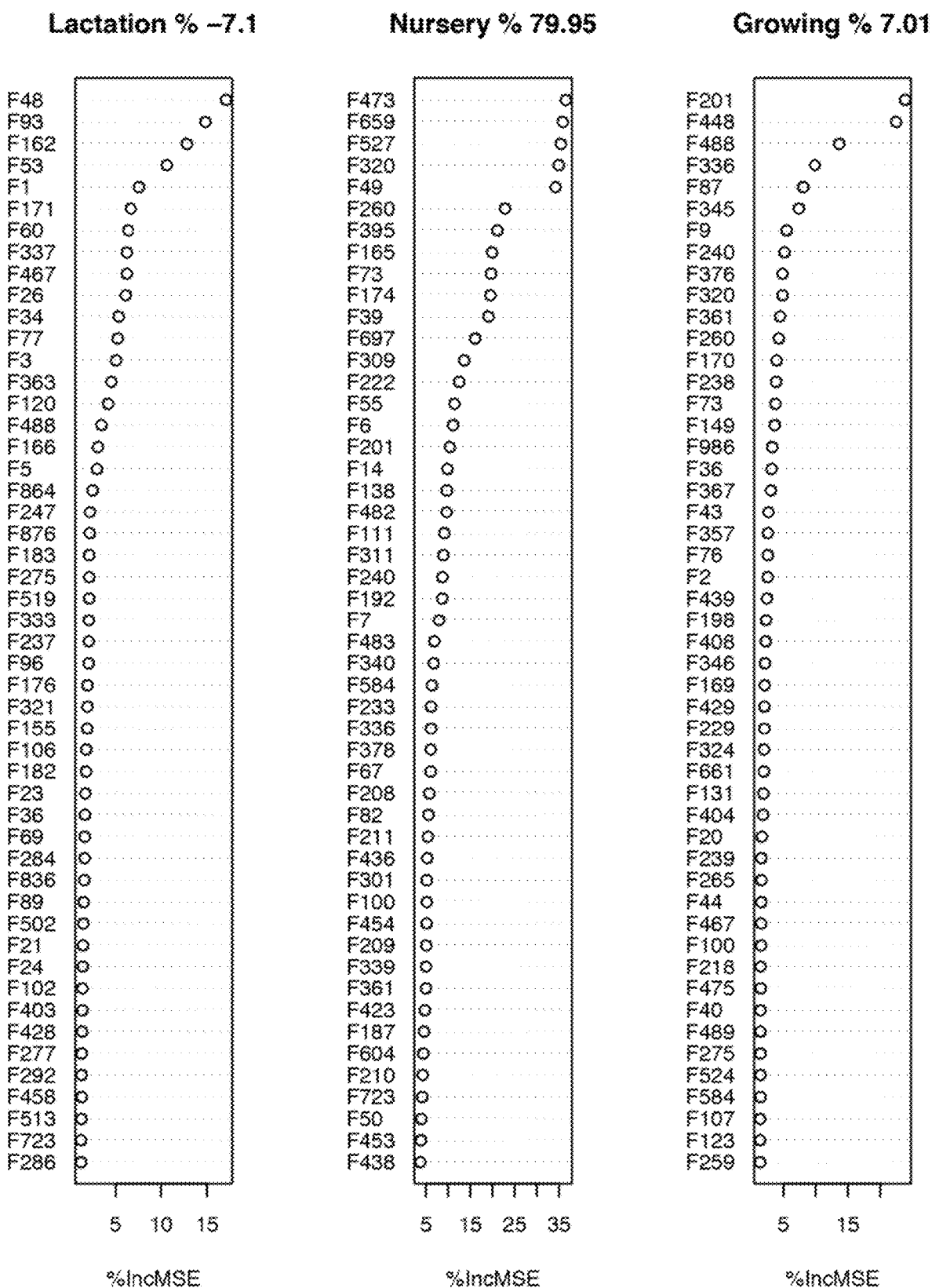
FIG. 21 shows growth performance-related features identified in the validation study. The top 50 beneficial bacteria identified at the lactation, nursery, growing, and finishing stages are shown. The final column shows the top 50 features across stages (overall). The top 50 features were selected from the top 500 features at each stage and across stages (Overall) using regression-based Random forest algorithm in R.

Interestingly, FMT from a growing stage donor did not change the swine gut microbiome at the nursery stage, i.e., the majority of the donor's gut microbiome did not colonize in the recipients, but did enhance growth performance. A deeper analysis of the individual bacterial features by LEfSe identified several features enriched by FMT including F2 (only on d 42), F41, F454, F309 and F348 on d 42 and d 61 (FIG. 19). The relative abundance of these features increased at subsequent time points after FMT (FIG. 20). Notably, F2 and F454 are listed among top features correlated with BW during growing stage and nursery stage, respectively (FIG. 21).

Isolation and Validation of Swine Probiotics that Promote Growth Performance

The stage-specific, growth-enhancing bacteria identified in this study include several strains that are promising probiotics candidates that could be used in the swine industry. For example, one promising candidate, StrepX (also referred to by its associated feature, "F2", herein), is a strain belongs to the Firmicutes phylum, *Streptococcus* genus, and *luteciae* species, based on sequencing of its V4 region of 16S ribosomal RNA and the Greengene database. StrepX was not only enriched by FMT, but also ranks as the 4th most abundant feature in the swine gut. Further, StrepX was identified in four of our previous studies under different conditions. For example, it was enriched in the high growth performance group of a study in which pigs were raised in isolators and fed with milk replacer and creep feed.

To preserve the majority of the swine gut bacteria for future probiotic isolation, we cultured the fecal microbiome from three pigs repeatedly at four different ages (d 20, 61, 116 and 174) using a total of 76 culturing methods with different combinations of media, oxygen, and blood bottle pre-incubation. After three to five days of culturing, all colonies from each plate were collected and preserved individually in 20% glycerol at −80° C. An aliquot of 50 µL of each cultured cell solution was sequenced using Miseq to catalogue the cultivatable bacteria. Using this method, we isolated three StrepX strains and two *lactobacillus* (LactX) strains from pigs at either d 116 or d 174 using modified Gifu anaerobic medium (MGAM; manufactured by HyServe) agar plates cultured at 37° C. under aerobic condition, and validated the identities of the strains by sequencing their 16 rRNA genes using Sanger DNA sequencing.

We next determined that two StrepX strains and one *Lactobacillus* (LactX) can survive a 3 hour incubation in 2% w/v porcine bile. This ability would help these strains survive in the gastrointestinal tract, making them good candidates for direct-fed probiotics.

In Vivo Validation of Swine Probiotics

Figure 24:
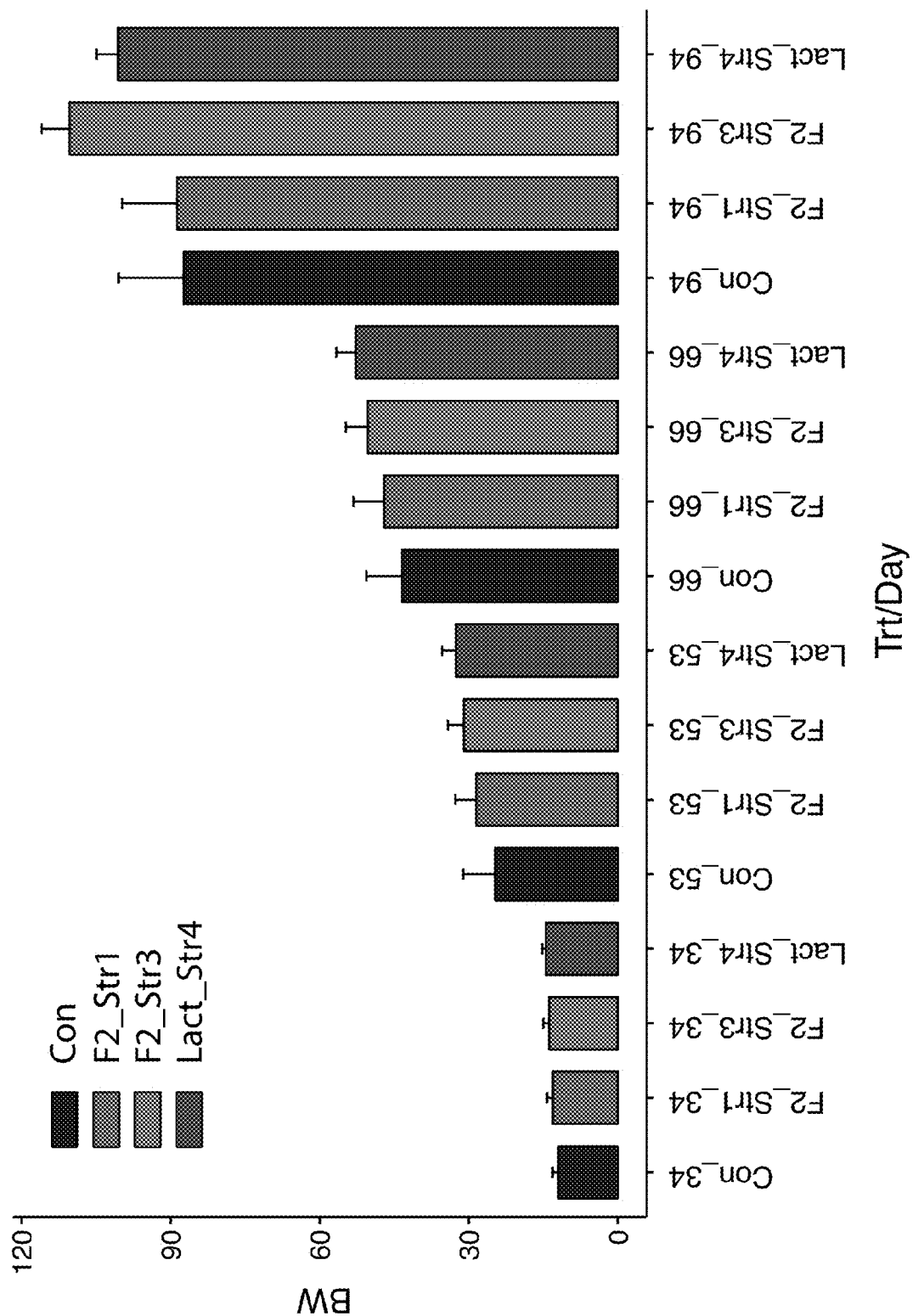
FIG. 24 shows the growth performance of control pigs (Con) and pigs fed with different bacterial strains (F2_Str1, F2_Str3, and Lact_Str4). Body weight was measured at three time points in the nursery phase: d 34, d 53, and d 66, and one in the growing phase: d 94. Strains StrepX_3 (F2_Str3) and LactX (Lact_Str4) significantly increased the body weight of pigs.

We next evaluated the two StrepX strains and one LactX strain in live pigs that were fed using the same 7-stage feeding regimen used in Animal Trial 1. Pure cultures of each isolate stored in MGAM broth were centrifuged and resuspended in PBS with 20% glycerol. The cellular suspensions were adjusted to OD 0.25 to achieve approximately $10^8$ cells/mL density. These pure cultures were preserved at −80° C. until use. A total of 48 pigs at the weaning stage were selected and gavaged with either control, StrepX1, StrepX3 or LactX (12 pigs per treatment/strain) for two consecutive days with 3 mL of each strain solution or vehicle (PBS with 20% glycerol). Booster drench was given at the end of nursery phase 2. The body weight and pen feed intake were monitored for individual pigs from weaning until the first phase of growing stages. Remarkably, we found that piglets gavaged with either StrepX3 or LactX at weaning had a heavier body weight than control group pigs through the nursery stage and growing phase 1 (Table 8 and FIG. 24). Specifically, the piglets gavaged with StrepX3 weighed 1.84 lbs (15.3%), 6.37 lbs (25.8%), and 6.89 lbs (15.9%) more on day 34, 53, and 66 of the nursery phase, and weighed about 22.92 lbs (26.2%) more at the end of growing stage phase 1, while piglets gavaged with LactX weighed 2.5 lbs (20.9%), 7.89 lbs (32.0%), and 9.38 lbs (21.6%) more on day 34, 53, and 66 of the nursery phase, and weighed about 13.22 lbs (15.1%) more at the end of growing stage phase 1.

TABLE 8

Growth performance of pigs fed with different bacterial strains.
The average body of each group of pigs is presented in pounds.

|  | Nursery d 34 | Nursery d 53 | Nursery d 66 | Growing d 94 |
| --- | --- | --- | --- | --- |
| Control | 11.95 | 24.675 | 43.37 | 87.375 |
| StrepX_1 | 13.102 | 28.47 | 47.04 | 88.75 |
| StrepX_3 | 13.79 | 31.04 | 50.26 | 110.3 |
| LactX | 14.45 | 32.56 | 52.75 | 100.6 |

Alpha Diversity

An overall increasing trend in alpha community diversity and richness of the gut microbiome was observed during the pre-harvest lifespan of the pigs, consistent with previously studies [10, 12]. Increased richness and diversity from 10-day pre-weaning to 21-day post-weaning were shown in commercial pigs [12]. Community diversity (Shannon index) plateaued on d 146, whereas richness indices (number of observed features) kept increasing until the end of the experiment when the pigs were shipped for slaughter. The high alpha diversities on d 174 were very comparable to those of the sows, indicating a fully developed swine gut microbiome before market. In our study, we did not observe decreased gut microbiome diversity on the last sampling dates before market, which is inconsistent with previous reports. Han (2018) observed reduced alpha diversities starting on d 63 when antibiotics were supplied in diets [13]. In a recent study, De Rodas and colleagues (2018) reported increased alpha diversity in different locations along the GI-tract from birth to d 84. Interestingly, they also observed decreased diversity in market samples [11]. Of note, pigs in their study were fed antibiotics-free diets, like those in our trial, but were supplemented with pharmaceutical levels of zinc during the nursery stage. Therefore, the differences between these studies on alpha diversity could be due to high zinc levels. Human microbiome diversity increases from infancy to adulthood when the community matures and stays stable before decreasing as people age, likely as a result of changes in diet, dentition, medication, and physiology of gut ecosystems [20]. Although domestic pigs can live as long as 20 years, the pre-harvest pigs raised in this study and in most commercial farms are mainly grown for food production and are reared for 6-7 months only before slaughter. Therefore, it is difficult to determine when the swine gut microbiome plateaus and how the swine gut microbiome changes during aging. Nonetheless, gut microbiome diversity of endpoint pigs were comparable with those of the sows, suggesting that the swine gut microbiome matures after the finishing stage.

Beta Diversity: Factors Shaping the Swine Gut Microbiome

This study provides a comprehensive view of the succession of the swine gut microbiome from birth to market by longitudinally collecting fecal samples from the same set of pigs across different growth stages. Such a study design allowed us to address several important ecological questions regarding the swine gut microbiome: 1) how does the swine gut microbiome change over time across different growth stages? and 2) what are the underlying determinants of these changes?

Figure 22:
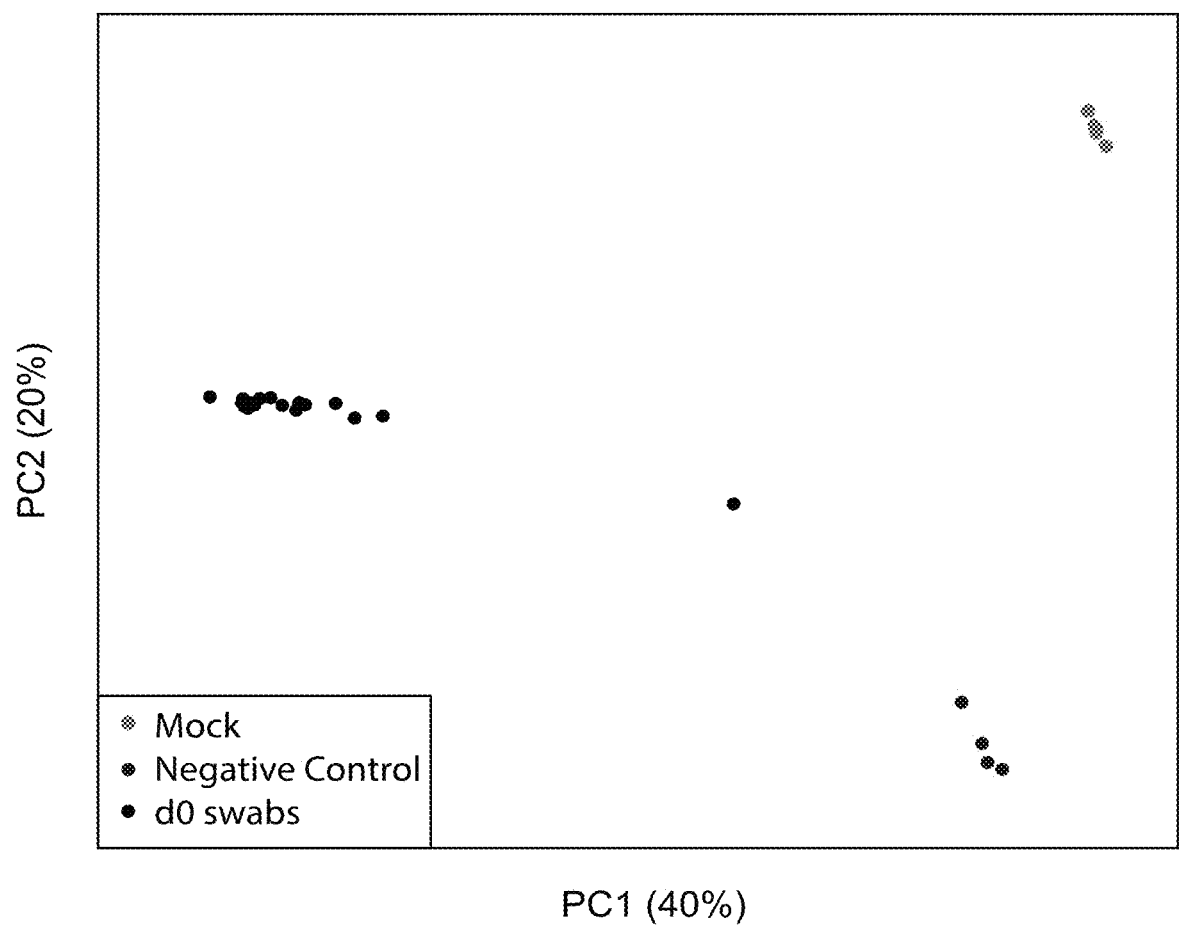
FIG. 22 shows a PCoA plot of negative controls, mock communities, and gut microbiome of day 0 piglets in the test study.

Our study showed consistent patterns of succession of the swine gut microbiome along different growth stages among the three groups of pigs from two different animal trials. At birth, meconium samples showed greater community diversity than the other two lactation samples. Dramatic decreases in community diversity and significant changes in community structure were observed on d 11 and d 20 when the pigs were fed sow milk. Whether the in utero environment is sterile has been a controversial issue in the field of human microbiome area. The meconium samples were collected within six hours after farrowing with possibilities for the pigs to suckle colostrum. Therefore, we can't rule out the possibility of postnatal colonization of bacteria from the colostrum, sow teat skin or the environment. However, given the fact that meconium samples were black and sticky, very different from other lactation fecal samples, and the meconium microbiomes were remarkably different from the day 11 and 20 fecal microbiomes, it is more likely that the meconium microbiomes were vertically transmitted from the sows rather than rapidly colonized by bacteria from other sources. Our study shows that, although the meconium bacterial biomass is low, with very low DNA concentration (less than 10 ng/μl), the meconium microbiomes are unlikely a result of contamination as they were distinct from those of the negative controls, and mock communities (FIG. 22). Thus, our data show that meconium samples harbor a diverse microorganisms (although with low bacterial load) that might serve as seeding bacteria to prime the development of the swine gut microbiome at subsequent time points, or to educate postnatal innate and adaptive immune responses [21]. Colostrum and milk consumption is critical for the development of GI-tract morphology, immune function, and the gut microbiome. Nutrients in milk such as oligosaccharides, amino acids, and fat activate digestive enzymes and chemical secretions, which alter the gut ecosystem for microbiome colonization [22]. The dramatic decrease of community diversity on d 11 indicates that the gut ecosystem during the first 10 days of life does not accommodate a highly diverse microbial colonization.

Another significant change in community structure occurred between d 20 (end of lactation) and d 27 (seven days postweaning), which might be attributed to weaning stress and/or the introduction of solid food. Weaning stress includes dietary and environmental transitions, and separation from the dam and typically results in reduced feed intake and growth performance as well as a high incidence of diarrhea [23]. Stress has been reported to contribute to various degrees of microbial dysbiosis that affect immune and endocrine systems [24]. Diet serves as a major challenge during weaning transitions, causing both physical and metabolic reconstructions in the GI tract. Sow milk is highly palatable and digestible whereas feed is rough, solid, less tasty, and not as easily digested [25]. Abrupt transitions to a solid feed diet induce short-term villus atrophy and crypt hyperplasia, which in turn impair digestive efficiency and gut integrity. A "leaky" gut could cause increased penetration of pathogens and nutrient loss.

Dramatic changes in both community structure and composition were observed 7 days postweaning. PCoA plots based on both Bray-Curtis and Jaccard showed distinct clusters completely separating the lactation and nursery microbiomes. Interestingly, such huge changes in microbiome did not happen in one day. In our validation trial, the microbiomes collected from the first two days (d 22 and 23) were not distinguishable from the end of lactation (d 21) samples. Given the fact that the d 27 samples in Trial 1 and the day 29 samples in Trial 2 were distinct from the d 20 end of lactation samples, we posit that it takes seven to nine days for the swine gut microbiome to adapt to a new diet and gut physiology.

The swine gut microbiome is driven by multiple factors such as host genetics, age, diet, environment, body weight, health, and antibiotics. Longitudinal studies are powerful given that animals serve as their own controls and many of the confounders are taken into consideration. However, it is also challenging in such studies to pinpoint which one is the major driver of the swine gut microbiome given that many of these factors are correlated. For instance, as pigs age, their body weights, rearing environments, and diet types also change accordingly. Therefore, we only selected age as a variable in the PERMANOVA models together with diet, sex, sow origin, and PigID. Diet was arguably the most important factor shaping the swine gut microbiome. Corn NDF in particular, had the strongest effect in shaping the swine gut microbiome. NDF contains most of the structural components in plant cells such as lignin, hemicellulose, and cellulose that cannot be digested by the pigs and are consequently passed to the colon for fermentation by the swine gut microbiota. Our data is consistent with previous studies. Frese et al. (2015) reported that the GI tract catabolic pathways shifted from milk-derived glycan metabolism to plant glycan deconstruction and consumption after a solid feed diet was introduced to the pigs [26]. Our previous findings suggested that neonatal pigs provided with milk replacer along with solid diets during lactation had microbial community structures distinct from those of their sow-fed littermates, suggesting the significant effect of diet on the gut microbiomes of pigs of similar age [6]. Similarly, Bian et al. (2016) also pointed out that the impact of age and diet on gut microbiome succession surpass that of sow genetics [27].

Age is another factor affecting the swine gut microbiome. Age is an indicator for physical maturation, which is accompanied by comprehensive functional transformations in metabolism, immunity, hormone secretion, muscle and bone development, and the nervous system [28, 29]. All these age-dependent biological alterations give rise to changes in microbiome structures [30-32].

"Core" Members, Residents, Passengers, and Origins of the Swine Gut Microbiome

This study also enabled us to address some other important biological questions regarding the swine gut microbiome, including: 1) What is the core gut microbiome? 2) Which bacterial taxa are residents, persisting in the whole pre-harvest section from birth to market? 3) Which bacteria are passengers, present only at a certain point in time? 4) What were the origins of the swine gut microbiome (e.g., sows, diet, or environment)?

A total of 69 core microbiome members were shared between the three groups of pigs in the two animal trials, based on the definition that these bacterial taxa were present at least in one pig of each group at all the time points. Notably, a subset of these members (13 out of 69) were present in at least 50% of the pigs for at least 150 days from birth to market. These members include features 1, 5, 8, 9, 13, 17, 23, 46, 50, 62, 77, 112, and 132. Among these features, five (Features 1, 5, 17, 62, and 132) were detected at all time points including d 0 (meconium), indicating vertical transmission of these bacterial taxa from the sows. These features were early colonizers of the swine gut and persisted throughout the entire pre-harvest lifespan, from sow milk-based lactation stage to the solid-feed based nursery, growing and finishing stages.

Some new colonizers appeared and persisted after the introduction of solid feed. These features include Features 3, 6, 12, 52, 63, and 153. Of note, F3 and F52 were detected in the d 0 samples as well, disappeared during lactation, then re-appeared after the solid feed supplementation in the nursery stage. Therefore, these taxa were likely vertically transmitted as well, but were suppressed during the lactation stage to an undetectable level, and proliferated when the nutrient and environment became more favorable. Many of these features belong to the genus of *Prevotella*, which was the largest genus in the swine gut microbiome at most of the time points during the solid feed stages. Members of *Prevotella* are associated with plant food-based diet and fiber digestion [33]. Interestingly, significant sub-OTU level differences in abundance and dynamics within this genus were observed. For example, members of *Prevotella copri* (Features 3, 6, 14, and 36) proliferated during the nursery phase and gradually decreased at subsequent stages, whereas features of the unclassified *Prevotella* (e.g., F9) were one of the residents of the swine GI-tract, present from the lactation until the end of the finishing stage. The roles that *P. copri* plays in human health has been debatable. In a recent study, De Filippis et al. (2019) detected distinct strains of *P. copri* by metagenome studies and showed that diet might select distinctive *P. copri* populations [34]. Genes were enriched for drug metabolism in individuals on a Western diet whereas genes in people consuming fiber-rich diets were enriched for complex carbohydrate degradation [34]. Introduction of solid fiber-rich feed during the nursery stage explains, at least partially, the increased abundance of *P. copri*. Similar to *P. copri*, members of Megaspheara (F1), and Blautia (F16) also increased postweaning, which is in agreement with previous reports [12]. Like *Prevotella*, members of Megaspheara, and Blautia can also degrade carbohydrate efficiently [35-37]. Therefore, these microbes proliferated postweaning when pigs were provided with plant carbohydrate diets.

Later colonizers appeared during the late growing stage and persisted throughout the entire finishing stage. These late colonizers include Features 4, 10, 18, and 19. Passengers refer to those bacterial taxa that showed up early or at the middle of the pre-harvest section but disappeared or faded out at later stages. Members associated with *E. coli* (F7) belong to the passengers category. In line with previous swine weaning [38-40] and human infant gut microbiome studies [41, 42], *E. coli* was abundant at birth (d 0) and during lactation stage but phased out after weaning, which could be due to the maturation of the immune system or suppression by other bacteria. Mucus presents a critical role for binding and preventing food-borne pathogens away from the host, and the physical structure of the mucosa is age-dependent [43, 44]. Pathogen-binding affinity of the mucus in immature animals is lower than in mature animals [45].

Potential Probiotics

The metabolic property of bacteria directly correlates with feed conversion rate and contributes to the host's nutrient supply. Modulation of the gut microbiome to improve feed efficiency has become a novel strategy in the livestock industry. In our study, we identified top bacterial taxa that are most positively related to BW in adult pigs. Feature 26, associated with *Turicibacter*, was positively correlated with BW on d 90, 104, 116, 130, 159, and 174. Of note, *Turicibacter* is related to host immunity and is sensitive to host GI-tract physiological conditions. *Turicibacter* populations were fewer in immunodeficient mice compared with their wild-type counterparts [46, 47]. Moreover, *Turicibacter* could reduce susceptibility to *Salmonella* infection in mice deficient in the expressions of blood group glycosyltransferase $\beta$-1,4-N-acetylgalactosaminyltransferase 2 (B4galnt2), which is responsible for the synthesis of blood antigens. Hence, *Turicibacter* might play some positive roles in swine-microbiome immune interactions, consequently promoting an enhanced growth performance.

Feature 27 is a member of *Clostridium butyricum* (*C. butyricum*), with positive correlations with BW on d 130, 159, and 174; *C. butyricum* produces butyric acids, which serves as the most efficient energy source for livestock and GI epithelium maintenances. Dietary *C. butyricum* supplementation on weaning piglets has been reported to reduce the diarrhea score and enhance intestinal villus height [48]. Supplementation with *Butyricum* in grow-finishing pigs showed enhanced energy conversion rate [49]. Furthermore, *C. butyricum* is also involved in GI immunosuppressive modulations. Chen and colleagues showed that *C. butyricum* supplementation during weaning suppressed pro-inflammatory response indicated by increased mucosa IL-10 and reduced plasma tumor necrosis factor (TNF)-$\alpha$ [48]. Therefore, *C. butyricum* could enhance growth performance by providing more energy and/or improve the immune system. Features 4 and 18 are all associated with Clostridiaceae. These taxa proliferated in later stages (growing-finishing) and were positively correlated with BW. Of note, F4 was remarkably abundant (about 8% on d 174) at these stages. Features 4 and 18 were positively correlated with BW at almost all the last seven sample collection dates.

Figure 23:
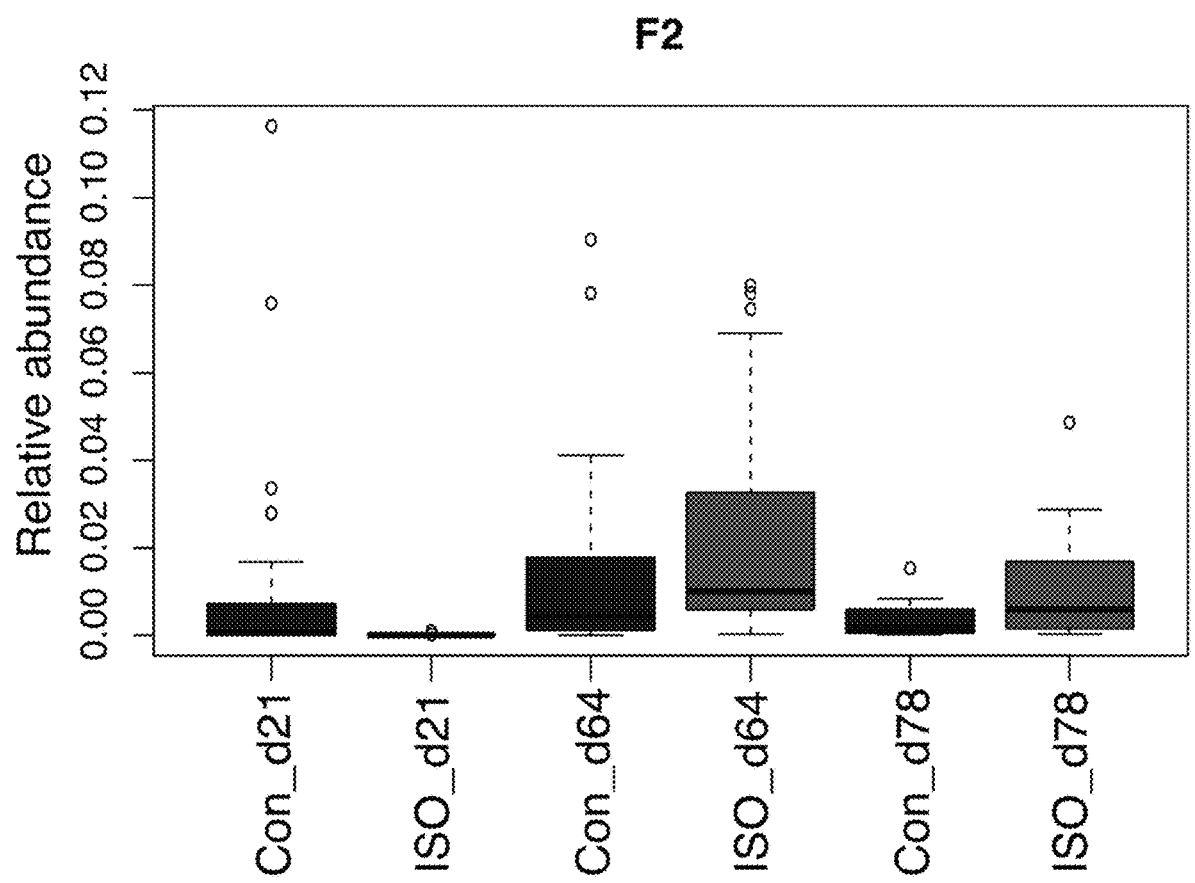
FIG. 23 shows the relative abundances of F2 in control (Con) and isolated (ISO) groups on day d 21, 64, and 78.

Features 2 (*Streptococcus*) and 454 (*Lactobacillus* mucosae) were identified as growth related taxa during the nursery phase in the first animal trial. In the second validation trial, FMT did not significantly change the overall community structure but did improve animal growth performance. Interestingly, abundance of both of these two features were increased by FMT, suggesting the colonization of these features and their possible roles in promoting animal growth. *Lactobacillus* mucosae was first isolated from pigs with mucus binding activity [50]. Members of this group have been reported to decrease epithelial permeability and improve barrier function. In another independent study, we detected improved growth performance in a group of pigs raised in an isolator with creep feed. In that study, F2 was also enriched in the high-performance group (FIG. 23) [6]. Although studies wherein these F2 strains are isolated and fed back to pigs would be necessary to prove their function in growth performance, our data in all these three trials corroborate F2 as a strong probiotic candidate.

CONCLUSIONS

The swine gut microbiome has received growing attention due to the fact that pigs serve as the most important protein source as well as an excellent biomedical model for human diseases. Despite the remarkable advances in our understanding of the swine gut microbiome from recent studies, many key ecological questions still remain unanswered. In this study, we characterized the longitudinal dynamics across all the different growth stages of the pigs in a test animal trial and validated these discoveries in a validation trial.

We observed consistent patterns of changes in swine gut microbiome structures along different growth stages in both animal trials. Diet, especially corn NDG, was the major driver of the swine gut microbiome. We identified 69 core microbiome members shared by the two animal trials. We also identified residents, passengers, early colonizers and later colonizers of the swine gut. The order and time of species arrival, i.e., the priority effects, were more evident at later growth stages when solid feed were introduced. Although FMT did not significantly change the recipients' gut microbiome, it did enrich a few bacterial taxa, which were correlated with the increased growth performance.

Our study answered several of the key ecological questions in the swine gut microbiome and also provide a foundation for studies aimed at improving animal health and production.

REFERENCES

1. McCormack U M, Curiao T, Buzoianu S G, Prieto M L, Ryan T, Varley P, Crispie F, Magowan E, Metzler-Zebeli B U, Berry D, et al: Exploring a Possible Link between the Intestinal Microbiota and Feed Efficiency in Pigs. *Applied and Environmental Microbiology* 2017, 83.
2. Ramayo-Caldas Y, Mach N, Lepage P, Levenez F, Denis C, Lemonnier G, Leplat J J, Billon Y, Berri M, Dore J, et al: Phylogenetic network analysis applied to pig gut microbiota identifies an ecosystem structure linked with growth traits. *Isme Journal* 2016, 10:2973-2977.
3. Yang H, Xiang Y, Robinson K, Wang J J, Zhang G L, Zhao J C, Xiao Y P: Gut Microbiota Is a Major Contributor to Adiposity in Pigs. *Frontiers in Microbiology* 2018, 9.
4. He B B, Bai Y, Jiang L L, Wang W, Li T T, Liu P, Tao S Y, Zhao J C, Han D D, Wang J J: Effects of oat bran on nutrient digestibility, intestinal microbiota, and inflammatory responses in the hindgut of growing Pigs. *International Journal of Molecular Sciences* 2018, 19.
5 Xiao Y, Kong F, Xiang Y, Zhou W, Wang J, Yang H, Zhang G, Zhao J: Comparative biogeography of the gut microbiome between Jinhua and Landrace pigs. *Sci Rep* 2018, 8:5985.
6. Tsai T, Sales M A, Kim H, Erf G F, Vo N, Carbonero F, van der Merwe M, Kegley E B, Buddington R, Wang X, et al: Isolated rearing at lactation increases gut microbial diversity and post-weaning performance in pigs. *Front Microbiol* 2018, 9:2889.
7. Pluske J R, Turpin D L, Kim J-C: Gastrointestinal tract (gut) health in the young pig. *Animal Nutrition* 2018, 4:187-196.

8. McCormack U M, Curião T, Buzoianu S G, Prieto M L, Ryan T, Varley P, Crispie F, Magowan E, Metzler-Zebeli B U, Berry D: Exploring a possible link between the intestinal microbiota and feed efficiency in pigs. *Applied environmental microbiology* 2017, 83: AEM. 00380-00317.
9. Xiao L, Estelle J, Kiilerich P, Ramayo-Caldas Y, Xia Z, Feng Q, Liang S, Pedersen A O, Kjeldsen N J, Liu C, et al: A reference gene catalogue of the pig gut microbiome. *Nat Microbiol* 2016:16161.
10. Lu D, Tiezzi F, Schillebeeckx C, McNulty N P, Schwab C, Shull C, Maltecca C: Host contributes to longitudinal diversity of fecal microbiota in swine selected for lean growth. *Microbiome* 2018, 6:4.
11. De Rodas B, Youmans B P, Danzeisen J L, Tran H, Johnson T J: Microbiome profiling of commercial pigs from farrow to finish. *Anim Sci* 2018, 96:1778-1794.
12. Chen L, Xu Y, Chen X, Fang C, Zhao L, Chen F: The maturing development of gut microbiota in commercial piglets during the weaning transition. *Front Microbiol* 2017, 8:1688.
13. Han G G, Lee J-Y, Jin G-D, Park J, Choi Y H, Kang S-K, Chae B J, Kim E B, Choi Y-J: Tracing of the fecal microbiota of commercial pigs at five growth stages from birth to shipment. *Scientific reports* 2018, 8:6012.
14. Kozich J J, Westcott S L, Baxter N T, Highlander S K, Schloss P D: Development of a dual-index sequencing strategy and curation pipeline for analyzing amplicon sequence data on the MiSeq Illumina sequencing platform. *Applied environmental microbiology* 2013, 79: AEM. 01043-01013.
15. Amir A, McDonald D, Navas-Molina J A, Kopylova E, Morton J T, Zech Xu Z, Kightley E P, Thompson L R, Hyde E R, Gonzalez A, Knight R: Deblur rapidly resolves single-nucleotide community sequence patterns. *mSystems* 2017, 2: e00191-00116.
16. Anderson Mj: Permutational multivariate analysis of variance (PERMANOVA). In *Wiley StatsRef: Statistics Reference Online.* 2017:1-15
17. Segata N, Izard J, Waldron L, Gevers D, Miropolsky L, Garrett W S, Huttenhower C: Metagenomic biomarker discovery and explanation. *Genome Biol* 2011, 12: R60.
18. Breiman L: Random forests. *J Machine learning* 2001, 45:5-32.
19. Girvan M, Newman M E: Community structure in social and biological networks. *Proc Natl Acad Sci USA* 2002, 99:7821-7826.
20. Kong F, Deng F, Li Y, Zhao J: Identification of gut microbiome signatures associated with longevity provides a promising modulation target for healthy aging. *Gut microbes* 2018, 10:1-6.
21. Wilczyńska P, Skarżyńska E, Lisowska-Myjak B: Meconium microbiome as a new source of information about long-term health and disease: questions and answers. *The Journal of Maternal-Fetal & Neonatal Medicine* 2019, 32:681-686.
22. Everaert N, Van Cruchten S, Weström B, Bailey M, Van Ginneken C, Thymann T, Pieper R: A review on early gut maturation and colonization in pigs, including biological and dietary factors affecting gut homeostasis. *Animal Feed Science Technology* 2017, 233:89-103.
23. Kim J, Hansen C F, Mullan B, Pluske J: Nutrition and pathology of weaner pigs: nutritional strategies to support barrier function in the gastrointestinal tract. *Animal feed science technology* 2012, 173:3-16.
24 Curley J P, Jordan E R, Swaney W T, Izraelit A, Kammel S, Champagne F A: The meaning of weaning: influence of the weaning period on behavioral development in mice. *Developmental neuroscience* 2009, 31:318-331.
25. Lalles J-P, Boudry G, Favier C, Le Floc'h N, Luron I, Montagne L, Oswald I P, Pie S, Piel C, Sève B: Gut function and dysfunction in young pigs: physiology. *Animal Research* 2004, 53:301-316.
26. Frese S A, Parker K, Calvert C C, Mills D A: Diet shapes the gut microbiome of pigs during nursing and weaning. *Microbiome* 2015, 3:28-28.
27. Bian G, Ma S, Zhu Z, Su Y, Zoetendal E G, Mackie R, Liu J, Mu C, Huang R, Smidt H, Zhu W: Age, introduction of solid feed and weaning are more important determinants of gut bacterial succession in piglets than breed and nursing mother as revealed by a reciprocal cross-fostering model. *Environmental Microbiology* 2016, 18:1566-1577.
28. Moeser A J, Pohl C S, Rajput M: Weaning stress and gastrointestinal barrier development: Implications for lifelong gut health in pigs. *Animal Nutrition* 2017, 3:313-321
29. Etherton T D, Aberle E D, Thompson E, Allen C E: Effects of cell size and animal age on glucose metabolism in pig adipose tissue. *Journal of lipid research* 1981, 22:72-86.
30. Chong C Y L, Bloomfield F H, O'Sullivan J M: Factors affecting gastrointestinal microbiome development in neonates. *Nutrients* 2018, 10:274.
31. Grosicki G J, Fielding R A, Lustgarten M S: Gut microbiota contribute to age-related changes in skeletal muscle size, composition, and function: biological basis for a gut-muscle axis. *Calcified tissue international* 2018, 102:1-10.
32. Houghteling P D, Walker W A: Why is initial bacterial colonization of the intestine important to the infant's and child's health? *Journal of pediatric gastroenterology nutrition* 2015, 60:294.
33. Wu G D, Chen J, Hoffmann C, Bittinger K, Chen Y Y, Keilbaugh S A, Bewtra M, Knights D, Walters W A, Knight R, et al: Linking long-term dietary patterns with gut microbial enterotypes. *Science* 2011, 334:105-108.
34. De Filippis F, Pasolli E, Tett A, Tarallo S, Naccarati A, De Angelis M, Neviani E, Cocolin L, Gobbetti M, Segata N, Ercolini D: Distinct genetic and functional traits of human intestinal *Prevotella copri* strains are associated with different habitual diets. *Cell Host Microbe* 2019, 25:444-453 e443.
35. Shetty S A, Marathe N P, Lanjekar V, Ranade D, Shouche Y S: Comparative genome analysis of Megasphaera sp. reveals niche specialization and its potential role in the human gut. *PLOS one* 2013, 8: e79353.
36. El Kaoutari A, Armougom F, Gordon J I, Raoult D, Henrissat B: The abundance and variety of carbohydrate-active enzymes in the human gut microbiota. *Nature reviews Microbiology* 2013, 11:497.
37. Chen T, Long W, Zhang C, Liu S, Zhao L, Hamaker B R: Fiber-utilizing capacity varies in *Prevotella*-versus *Bacteroides*-dominated gut microbiota. *Scientific reports* 2017, 7:2594.
38. Pajarillo E A B, Chae J-P, Balolong M P, Kim H B, Kang D-K: Assessment of fecal bacterial diversity among healthy piglets during the weaning transition. *The Journal of general applied microbiology* 2014, 60:140-146.
39. Chen W, Mi J, Lv N, Gao J, Cheng J, Wu R, Ma J, Lan T, Liao X: Lactation stage-dependency of the sow milk microbiota. *Frontiers in microbiology* 2018, 9:945.
40. Mach N, Berri M, Estelle J, Levenez F, Lemonnier G, Denis C, Leplat J J, Chevaleyre C, Billon Y, Dore J:

Early-life establishment of the swine gut microbiome and impact on host phenotypes. *Environmental microbiology reports* 2015, 7:554-569.
41. Rodríguez J M, Murphy K, Stanton C, Ross R P, Kober O I, Juge N, Avershina E, Rudi K, Narbad A, Jenmalm M C: The composition of the gut microbiota throughout life, with an emphasis on early life. *Microbial ecology in health disease* 2015, 26:26050.
42. Bäckhed F, Roswall J, Peng Y, Feng Q, Jia H, Kovatcheva-Datchary P, Li Y, Xia Y, Xie H, Zhong H: Dynamics and stabilization of the human gut microbiome during the first year of life. *Cell host microbe* 2015, 17:690-703.
43. Rachagani S, Torres M P, Kumar S, Haridas D, Baine M, Macha M A, Kaur S, Ponnusamy M P, Dey P, Seshacharyulu P: Mucin (Muc) expression during pancreatic cancer progression in spontaneous mouse model: potential implications for diagnosis and therapy. *Journal of hematology oncology* 2012, 5:68.
44. Brown D, Maxwell C, Erf G, Davis M, Singh S, Johnson Z: The influence of different management systems and age on intestinal morphology, immune cell numbers and mucin production from goblet cells in post-weaning pigs. *Veterinary immunology immunopathology* 2006, 111:187-198.
45. Turck D, Feste A S, Lifschitz C H: Age and diet affect the composition of porcine colonic mucins. *Pediatric Research* 1993, 33:564.
46. Dimitriu P A, Boyce G, Samarakoon A, Hartmann M, Johnson P, Mohn W W: Temporal stability of the mouse gut microbiota in relation to innate and adaptive immunity. *Environmental microbiology reports* 2013, 5:200-210.
47. Kellermayer R, Dowd S E, Harris R A, Balasa A, Schaible T D, Wolcott R D, Tatevian N, Szigeti R, Li Z, Versalovic J: Colonic mucosal DNA methylation, immune response, and microbiome patterns in Toll-like receptor 2-knockout mice. *The FASEB Journal* 2011, 25:1449-1460.
48. Chen L, Li S, Zheng J, Li W, Jiang X, Zhao X, Li J, Che L, Lin Y, Xu S: Effects of dietary *Clostridium butyricum* supplementation on growth performance, intestinal development, and immune response of weaned piglets challenged with lipopolysaccharide. *Journal of animal science biotechnology* 2018, 9:62.
49. Meng Q, Yan L, A X, Zhou T, Wang J, Lee J, Kim I: Influence of probiotics in different energy and nutrient density diets on growth performance, nutrient digestibility, meat quality, and blood characteristics in growing-finishing pigs. *Animal science* 2010, 88:3320-3326.
50. Roos S, Karner F, Axelsson L, Jonsson H: *Lactobacillus* mucosae sp. nov., a new species with in vitro mucus-binding activity isolated from pig intestine. *Int J Syst Evol Microbiol* 2000, 50 Pt 1:251-258.

Example 2. Assessment of the Impact of Bacterial Feature F2 on Growth Performance and Carcass Quality in Grower/Finisher Pigs In Example 1, the inventors discovered that the bacterial feature 2 (F2; SEQ ID NO:1), which was associated with the bacteria strain StrepX (SEQ ID NO:2), is correlated with the body weight of pigs (Wang et al., 2019). This correlation was validated by cross examination with several independent trials. However, the impact of this bacterium on the growth performance and carcass quality in grower/finisher pigs remained unclear.

Previous studies that have looked at the impact of direct fed microbes on growth performance in swine have produced inconsistent results with respect to the ability of the feed additive to improve growth performance to levels that are comparable to those achieved with antibiotics (Liu et al., 2018). Understanding the impact of a selected probiotic on meat quality and food safety in addition to promoting improved growth performance is essential (Markowiak & Śliżewska, 2018).

To better understand the beneficial effects of F2, we continued the trial initiated in Example 1 in which pigs were supplemented with F2 during the nursery stage. Here, we evaluate the effect of F2 supplementation on growth performance across the entire pre-harvest period. We demonstrate that treatment with F2 at weaning increases the growth rate of pigs comparably to treatment with antibiotics, without affecting carcass characteristics.

Materials and Methods

Animal Management and Feeding

On weaning day, a total of 96 pigs (PIC 1050×DNA600) with initial body weight of 6.19±0.3 kg were selected and transferred to a nursery facility for a 40 days nursery trial. In the new facility, there are 24 wired floor pens equipped with a cup waterer and a two-hole feeder. The piglets were housed four per pen (size: 1.5×1.2 $m^2$) throughout the nursery trial with ad libitum access to diet and water. Piglets were grouped into 8 blocks based on weaning body weight within gender and pigs within each block were then allotted to one of three pens, which were randomly assigned to three treatments. Each pen housed 2 gilts and 2 barrows. Hence, a total of 32 pigs were assigned to each treatment. Upon weaning, pigs were stratified by weaning body weight within each gender and then allotted to one of three treatments in phase 1 and phase 2:1) control: corn-SBM based diet; 2) F2: control diet plus F2 gavage; 3) Antibiotics: control diet plus antibiotics. All piglets were fed a common phase 3 diet. Pigs assigned to the F2 treatment group were drenched with F2 (approximately $10^9$ CFU/pig) on weaning day (d 0), on day 1 (d 1) and again at the end of nursery phase 2 (d 28). For the antibiotic treatment group, Carbadox (Mecadox® 10, Phibro Animal Health Corporation, Teaneck, NJ), and tiamulin hydrogen fumarate (Denagard®) plus chlortetracycline hydrochloride (CTC®, Novartis Animal Health US Inc, Greensboro, NC) were added in phase 1 and 2, respectively.

Diets were formulated to meet or exceed NRC (2012) recommendations for nursery pigs. All diets were in mash form. Feed was prepared and feed subsample from each diet was stored at −20° C. for future nutritional analysis. A three-phase dietary regimen was used for phase 1 (d 0-14), phase 2 (d 14-28), and phase 3 (d 28-40) in the nursery stage. Experimental diets were provided during phase 1 and 2, while all pigs were fed a common antibiotic free diet in phase 3. The composition of the diets provided at nursery phase 1, nursery phase 2, nursery phase 3, and the grower/finisher stages are presented in Tables 9-12, below.

TABLE 9

Nursery phase 1 diet composition (as fed)

| | Control | Antibiotics | F2 |
|---|---|---|---|
| Ingredients, % | | | |
| Corn, Yellow Dent | 42.25 | 41.25 | 42.25 |
| Soybean meal, 48% | 19.5 | 19.5 | 19.5 |
| Poultry Fat | 2.5 | 2.5 | 2.5 |
| Monocalcium P | 0.46 | 0.46 | 0.46 |
| Limestone | 0.55 | 0.55 | 0.55 |
| Salt | 0.25 | 0.25 | 0.25 |
| L-Lysine | 0.255 | 0.255 | 0.255 |
| DL-Methionine | 0.163 | 0.163 | 0.163 |
| L-Threonine | 0.0975 | 0.0975 | 0.0975 |
| L-Tryptophan | 0.015 | 0.015 | 0.015 |
| L-Valine | 0.016 | 0.016 | 0.016 |
| Trace Mineral Premix | 0.15 | 0.15 | 0.15 |
| Vitamin Premix | 0.25 | 0.25 | 0.25 |
| Fish Meal, Menhaden | 5 | 5 | 5 |
| Milk, Whey Powder | 20 | 20 | 20 |
| Ronozyme P CT | 0.015 | 0.015 | 0.015 |
| Ethoxiquin (Quinguard) | 0.03 | 0.03 | 0.03 |
| Mecadox | 0 | 1 | 0 |
| Hamlet 300 | 5 | 5 | 5 |
| Milk, Lactose | 3.5 | 3.5 | 3.5 |
| Total | 100 | 100 | 100 |
| Calculate | | | |
| ME (kcal/kg) | 3467 | 3433 | 3467 |
| CP (%) | 21.50 | 21.42 | 21.50 |
| SID Lysine (%) | 1.35 | 1.34 | 1.35 |
| SID Met (%) | 0.49 | 0.49 | 0.49 |
| SID Cys (%) | 0.29 | 0.29 | 0.29 |
| SID M + C (%) | 0.78 | 0.78 | 0.78 |
| SID Threonine (%) | 0.83 | 0.83 | 0.83 |
| SID Tryptophan (%) | 0.26 | 0.26 | 0.26 |
| SID Isoleucine (%) | 0.83 | 0.82 | 0.83 |
| SID Valine (%) | 0.90 | 0.90 | 0.90 |
| SID Leucine (%) | 1.60 | 1.59 | 1.60 |
| SID Histidine (%) | 0.50 | 0.49 | 0.50 |
| SID Arginine (%) | 1.17 | 1.17 | 1.17 |
| SID Phenylalanine (%) | 0.86 | 0.86 | 0.86 |
| SID Tyrosine (%) | 0.59 | 0.59 | 0.59 |
| SID Phe + Tyr (%) | 1.45 | 1.45 | 1.45 |

The vitamin premix provided the following per kg of complete diet: 397.5 mg of Ca as $CaCO_3$, 11,022.9 IU of vitamin A, 1,377.9 IU of vitamin $D_3$, 44.09 IU of vitamin E, 0.0386 mg vitamin $B_{12}$, 4.41 mg of menadione, 8.27 mg of riboflavin, 27.56 mg of D-pantothenic acid, and 49.6 mg of niacin.
The mineral premix provided the following per kg of complete diet: 84 mg of Ca as $CaCO_3$, 165 mg of Fe as $FeSO_4$, 165 mg of Zn as $ZnSO_4$, 39.6 mg of Mn as $MnSO_4$, 16.5 mg of Cu as $CuSO_4$, 0.3 mg of I as $CaI_2$, and 0.3 mg of Se as $Na_2SeO_3$.

TABLE 10

Nursery phase 2 diet composition (as fed)

| | Control | Antibiotics | F2 |
|---|---|---|---|
| Ingredients, % | | | |
| Corn, Yellow Dent | 52.70 | 52.33 | 52.70 |
| Soybean meal, 48% | 25 | 25 | 25 |
| Poultry Fat | 2.5 | 2.5 | 2.5 |
| Monocalcium P | 0.3 | 0.3 | 0.3 |
| Limestone | 0.945 | 0.945 | 0.945 |
| Salt | 0.5 | 0.5 | 0.5 |
| L-Lysine | 0.4 | 0.4 | 0.4 |
| DL-Methionine | 0.199 | 0.199 | 0.199 |
| L-Threonine | 0.16 | 0.16 | 0.16 |
| L-Tryptophan | 0.03 | 0.03 | 0.03 |
| L-Valine | 0.069 | 0.069 | 0.069 |
| Trace Mineral Premix | 0.15 | 0.15 | 0.15 |
| Vitamin Premix | 0.25 | 0.25 | 0.25 |
| Fish Meal, Menhaden | 2.5 | 2.5 | 2.5 |
| Milk, Whey Powder | 10 | 10 | 10 |
| Ronozyme P CT | 0.015 | 0.015 | 0.015 |
| Ethoxiquin (Quinguard) | 0.03 | 0.03 | 0.03 |
| Denaguard 10 | 0 | 0.2 | 0 |
| Chlortetracycline 100 (ADM) | 0 | 0.175 | 0 |
| Hamlet 300 | 2.5 | 2.5 | 2.5 |
| Milk, Lactose | 1.75 | 1.75 | 1.75 |
| Total | 100 | 100 | 100 |
| Calculate | | | |
| ME (kcal/kg) | 3437 | 3425 | 3437 |
| CP (%) | 21.17 | 21.14 | 21.17 |
| SID Lysine (%) | 1.35 | 1.35 | 1.35 |
| SID Met (%) | 0.50 | 0.50 | 0.50 |
| SID Cys (%) | 0.28 | 0.28 | 0.28 |
| SID M + C (%) | 0.78 | 0.78 | 0.78 |
| SID Threonine (%) | 0.84 | 0.84 | 0.84 |
| SID Tryptophan (%) | 0.26 | 0.26 | 0.26 |
| SID Isoleucine (%) | 0.78 | 0.77 | 0.78 |
| SID Valine (%) | 0.90 | 0.90 | 0.90 |
| SID Leucine (%) | 1.55 | 1.54 | 1.55 |
| SID Histidine (%) | 0.49 | 0.49 | 0.49 |
| SID Arginine (%) | 1.18 | 1.18 | 1.18 |
| SID Phenylalanine (%) | 0.86 | 0.86 | 0.86 |
| SID Tyrosine (%) | 0.57 | 0.57 | 0.57 |
| SID Phe + Tyr (%) | 1.43 | 1.43 | 1.43 |

The vitamin premix provided the following per kg of complete diet: 397.5 mg of Ca as $CaCO_3$, 11,022.9 IU of vitamin A, 1,377.9 IU of vitamin $D_3$, 44.09 IU of vitamin E, 0.0386 mg vitamin $B_{12}$, 4.41 mg of menadione, 8.27 mg of riboflavin, 27.56 mg of D-pantothenic acid, and 49.6 mg of niacin.
The mineral premix provided the following per kg of complete diet: 84 mg of Ca as $CaCO_3$, 165 mg of Fe as $FeSO_4$, 165 mg of Zn as $ZnSO_4$, 39.6 mg of Mn as $MnSO_4$, 16.5 mg of Cu as $CuSO_4$, 0.3 mg of I as $CaI_2$, and 0.3 mg of Se as $Na_2SeO_3$.

TABLE 11

Nursery phase 3 diet composition (as fed)

| Ingredients, % | |
|---|---|
| Corn, Yellow Dent | 57.6 |
| Soybean meal, 48% | 29 |
| Corn DDGS, > 6 and < 9% Oil | 7.5 |
| Poultry Fat | 2.5 |
| Monocalcium P | 0.4 |
| Limestone | 1.11 |
| Salt | 0.5 |
| L-Lysine | 0.5 |
| DL-Methionine | 0.184 |
| L-Threonine | 0.1775 |
| L-Tryptophan | 0.024 |
| L-Valine | 0.0575 |
| Trace Mineral Premix | 0.15 |
| Vitamin Premix | 0.25 |
| Ronozyme P CT | 0.015 |
| Ethoxiquin (Quinguard) | 0.03 |
| Total | 100 |
| Calculate | |
| ME (kcal/kg) | 3413 |
| CP (%) | 21.53 |
| SID Lysine (%) | 1.31 |
| SID Met (%) | 0.48 |
| SID Cys (%) | 0.28 |
| SID M + C (%) | 0.76 |
| SID Threonine (%) | 0.81 |
| SID Tryptophan (%) | 0.24 |
| SID Isoleucine (%) | 0.75 |
| SID Valine (%) | 0.88 |
| SID Leucine (%) | 1.61 |
| SID Histidine (%) | 0.49 |
| SID Arginine (%) | 1.20 |

TABLE 11-continued

Nursery phase 3 diet composition (as fed)

| | |
|---|---|
| SID Phenylalanine (%) | 0.89 |
| SID Tyrosine (%) | 0.60 |
| SID Phe + Tyr (%) | 1.48 |

The vitamin premix provided the following per kg of complete diet: 397.5 mg of Ca as CaCO$_3$, 11,022.9 IU of vitamin A, 1,377.9 IU of vitamin D$_3$, 44.09 IU of vitamin E, 0.0386 mg vitamin B$_{12}$, 4.41 mg of menadione, 8.27 mg of riboflavin, 27.56 mg of D-pantothenic acid, and 49.6 mg of niacin.
The mineral premix provided the following per kg of complete diet: 84 mg of Ca as CaCO$_3$, 165 mg of Fe as FeSO$_4$, 165 mg of Zn as ZnSO$_4$, 39.6 mg of Mn as MnSO$_4$, 16.5 mg of Cu as CuSO$_4$, 0.3 mg of I as CaI$_2$, and 0.3 mg of Se as Na$_2$SeO$_3$.

TABLE 12

Grower and finisher diet compositions (as fed)

| | Grower | Grower | Finisher | Finisher | Finisher |
|---|---|---|---|---|---|
| Phase | 1 | 2 | 1 | 2 | 3 |
| BW range | 50-90 | 90-130 | 130-180 | 185-230 | 230-290 |
| Ave BW | 70 | 110 | 155 | 215 | 260 |
| Ingredients | | | | | |
| Corn, Yellow Dent | 53.12 | 59.28 | 65.12 | 69.94 | 77.07 |
| Soybean meal, 48%, high protein, dehulled, sol extracted | 22.5 | 16.5 | 10.9 | 6.25 | 9.25 |
| Corn DDGS, > 6 and < 9% Oil | 20 | 20 | 20 | 20 | 10 |
| Fat (Darling, Yellow Grease) | 1 | 1 | 1 | 1 | 1 |
| Calcium phosphate (monocalcium) | 0.65 | 0.55 | 0.45 | 0.35 | 0.3 |
| Limestone, 2012 NRC | 1.3 | 1.25 | 1.21 | 1.15 | 1.04 |
| Sodium chloride | 0.4 | 0.4 | 0.4 | 0.4 | 0.5 |
| L-Lysine | 0.475 | 0.475 | 0.475 | 0.475 | 0.4 |
| DL-Methionine | 0.077 | 0.057 | 0.0275 | 0.01 | 0.019 |
| L-Threonine | 0.108 | 0.11 | 0.111 | 0.11 | 0.119 |
| L-Tryptophan | 0.0235 | 0.03 | 0.037 | 0.042 | 0.03 |
| Trace Mineral Premix (NB-8534) | 0.15 | 0.15 | 0.1 | 0.1 | 0.1 |
| Vitamin Premix (NB-6508) | 0.15 | 0.15 | 0.125 | 0.125 | 0.125 |
| Ronozyme P CT | 0.015 | 0.015 | 0.015 | 0.015 | 0.015 |
| Ethoxiquin (Quinguard) | 0.03 | 0.03 | 0.03 | 0.03 | 0.03 |
| Total | 100 | 100 | 100 | 100 | 100 |
| Calculate | | | | | |
| ME (Mcal/lb) | 1.51 | 1.52 | 1.52 | 1.53 | 1.53 |
| NE (Mcal/lb) | 1.11 | 1.13 | 1.15 | 1.16 | 1.17 |
| ME (kcal/kg) | 3337 | 3347 | 3360 | 3370 | 3368 |
| CP (%) | 21.29 | 18.93 | 16.73 | 14.90 | 14.10 |
| SID Lysine (%) ME basis | 1.18 | 1.03 | 0.89 | 0.78 | 0.76 |
| Total P (%) | 0.56 | 0.51 | 0.46 | 0.42 | 0.39 |
| Available P (%) | 0.29 | 0.26 | 0.23 | 0.20 | 0.17 |
| Available P (%) with phytase | 0.38 | 0.35 | 0.32 | 0.29 | 0.26 |
| Ca (%) | 0.71 | 0.66 | 0.60 | 0.55 | 0.50 |
| g Total Lysine/ Mcal NSNG ME | 4.05 | 3.56 | 3.09 | 2.71 | 2.59 |
| g SID Lysine/Mcal NSNG ME | 3.52 | 3.07 | 2.65 | 2.31 | 2.25 |
| SID M + C:Lys | 56 | 57 | 57 | 58 | 58 |
| SID Thr:Lys | 61 | 62 | 63 | 64 | 66 |
| SID Trp:Lys | 18 | 18 | 18 | 18 | 18 |
| SID Ile:Lys | 61 | 59 | 58 | 57 | 57 |
| SID Val:Lys | 69 | 69 | 70 | 70 | 69 |
| SID Leu:Lys | 145 | 152 | 161 | 171 | 160 |
| SID His:Lys | 41 | 41 | 42 | 42 | 42 |
| SID Arg:Lys | 94 | 90 | 85 | 81 | 86 |

Mineral mix supplies supplies 80 ppm Fe as Iron Sulfate, 0.30 ppm Se from Na$_2$SeO$_3$, 30 ppm Mn as Manganese hydroxychloride, 12 ppm Cu as Copper chloride tri-basic, and 0.40 ppm I as Ethylenediamine Dihydroiodide per kg of diet in grower and finisher diets.
Vitamin mix supplies 11,023 IU of vitamin A, 1,377 IU of vitamin D3, 44 IU of vitamin E, 4.4 mg of vitamin K as menadione, 27 mg of pantothenic acid as D-calcium pantothenate, 50 mg niacin, 8 mg of riboflavin, and 38 µg of vitamin B$_{12}$ per kg of grower feed, while Vitamin mix supplies 4,409 IU of vitamin A, 551 IU of vitamin D$_3$, 18 IU of vitamin E, 1.76 mg of vitamin K as menadione, 11 mg of pantothenic acid as D-calcium pantothenate, 20 mg niacin, 3.3 mg of riboflavin, and 15 µg of vitamin 12 per kg of finisher feed.

At the end of the nursery stage, all pigs were transferred from the nursery to a finisher barn. A pig was kept with its pen-mate from nursery stage when transferred to the finisher unit. Pigs were fed a 5-phase growing/finishing regime. Phase change was made according to body weight: grower phase 1 (50-90 lbs), grower phase 2 (90-140 lbs), finisher phase 1 (140-185 lbs), finisher phase 2 (185-230 lbs), and finisher phase 3 (230-280 lbs). Typically, pigs were fed with each phase diet for approximately 3 weeks. All pigs had free access to feed and water during the experiment. Pigs were housed in a curtain-sided building with slatted floors, and each 4.9×9.8 feet (1.5×3.0 m) pen was equipped with a single-hole feeder and wean-to-finish cup waterers for ad libitum access to food and water. The ambient temperature was maintained according to SOP #302.01. Daily temperature (min and max) was recorded, and any medication requirement was recorded and reported. The minimum computer-controlled temperature is reported in Table 13, below.

TABLE 13

Minimum computer-controlled temperature

| Day | 1 | 5 | 10 | 21 | 28 | 35 | 50 | 60 | 70 | 80 |
|---|---|---|---|---|---|---|---|---|---|---|
| Temp, °F. | 75.0 | 74.0 | 73.0 | 72.0 | 71.0 | 70.5 | 70.0 | 69.5 | 69.0 | 68.0 |

Sample Collection

Body weight and feed intake were recorded at the end of every phase to calculate the average daily gain (ADG), average daily feed intake (ADFI), and gain to feed ratio (G:F) for each phase.

Rectal swabs and feces were collected from two piglets that were close to the pen average bodyweight in every pen, totaling 48 piglets, at the end of nursery phase 2 and grower phase 2 for a final total of 96 swabs and 96 fecal samples. The Puritan Opti-Swab Liquid Amies Collection and Transport System (Puritan Medical products, Guilford, Maine) was used for swab sampling. Swabs were used in the microbiome analysis and fecal samples were used in the metagenomics and metabolomics analysis.

At weaning (d 0), the end of nursery phase 2, the end of nursery (d 40), and the end of grower phase 2 (d 104) blood samples were collected via jugular venipuncture into evacuated tubes containing EDTA from 1 piglet close to pen average body weight in every pen, totaling 96 samples. Blood samples were centrifuged at 3000 g for 10 minutes at 4° C. The plasma was aspirated to 5 ml polypropylene sample tubes, and stored at −80° C. for metabolomics analysis.

At the end of the trial, a total of 24 pigs (1 pig per pen) were harvested for carcass quality analysis. Longissimus muscle (LM) and fat depths at the $10^{th}$ rib were measured on-line with a Fat-O-Meater probe and hot carcass weight was recorded for each pig/carcass. Following harvest, the loin and belly was removed from one side for further carcass quality analysis.

Carcass Quality

Carcass quality assessment included an assessment of: longissimus muscle (LM) and fat depth, hot carcass weight, loin meat quality (color and marbling score, tenderness, shear force, cook loss, and proximate analysis) and pork belly quality (fatty acid profile analysis, iodine values, belly thickness, and belly firmness).

After the loin and belly were collected, loins were analyzed according to the National Pork Board guidelines for color and marbling scores following a 20 min bloom period. Color was objectively analyzed using a HunterLab MiniScan EZ spectrophotometer, according to the AMSA Color Guidelines. Following color analysis, loins were cut into 2.54 cm thick chops. Following fabrication, paired chops were aged for 10 days and randomly assigned to the following analyses: tenderness, cook loss, and proximate analysis. Instrumental tenderness was determined using Warner-Bratzler shear force following the protocol outlined by the AMSA Sensory Guidelines. Briefly, chops were cooked to an internal temperature of 71° C., then cooled overnight. Six 1.27 cm cores were removed parallel to the muscle fiber direction and sheared perpendicular. The cores were averaged across the chops to create a value for each loin. Cooking loss were conducted on the same chops. A raw weight was taken prior to cooking, followed by a cooked weight, then calculated as (raw weight-cooked weight)/raw weight*100. For proximate analysis, samples were homogenized with liquid nitrogen to form a homogenous powder. Then samples were analyzed by an AOAC approved method for moisture and lipid analysis.

Bellies were subjected to pork quality analysis through fatty acid profile analysis, iodine values, belly thickness, and belly firmness. Bellies were subjected to thickness and firmness measurements described by Browne et al. (2013). For fatty acid analysis, the protocol described by O'Fallon et al. (2007) will be used. Briefly, sections of belly will be liquid nitrogen homogenized. One gram of powdered sample will be weighed into 20 ml glass vials, then 1 mL of C13:0 will be added to the sample as an internal standard. After addition of the internal standard, 0.7 mL of 10 N potassium hydroxide and 5.3 mL of methanol will be added to the tube for derivatization and the tube will be incubated for 1.5 h at 55° C. Following the hot water bath, tubes will be submerged in cold water for 20 min. 0.58 mL of 24 N sulfuric acid will be added to the tubes and then tubes will be re-incubated under the previous conditions. Following the final incubation, 3 mL of hexane will be added to the tubes and tubes will be vortexed for 5 min, then centrifuged for 5 min at 3500 RPM. The hexane layer, containing the FAMES, will be placed into labeled gas chromatography vials. Gas chromatography-flame ionization detection will be used to detect fatty acid concentration. Following separation, fatty acid identity and quantity will be confirmed using external standards and calculated on a weight basis. The fatty acid concentrations observed will be used to calculate iodine values as described by Browne et al. (2013).

Statistical Analysis

Quantitative traits were analyzed using the PROC Mixed of SAS procedure (SAS Institute, Inc., Cary, NC) with treatment as fix effect and body weight block as random effect. Each pen was an experiment unit for ANOVA. Comparisons between treatments were considered significantly different when the p-value is ≤0.05.

Results:

During the entire trial we lost one pig from the antibiotic treatment group (dead) during the nursery period, whereas two pigs from the antibiotic treatment group (prolapse), three pigs from the control group (1 dead, 1 prolapse, 1 dislocate hip), and three pigs from the F2 treatment group (1 dead, 1 prolapse, 1 bloody stool) were lost during the grower and finisher periods. Growth performances are presented in Tables 14-17.

Figure 25:
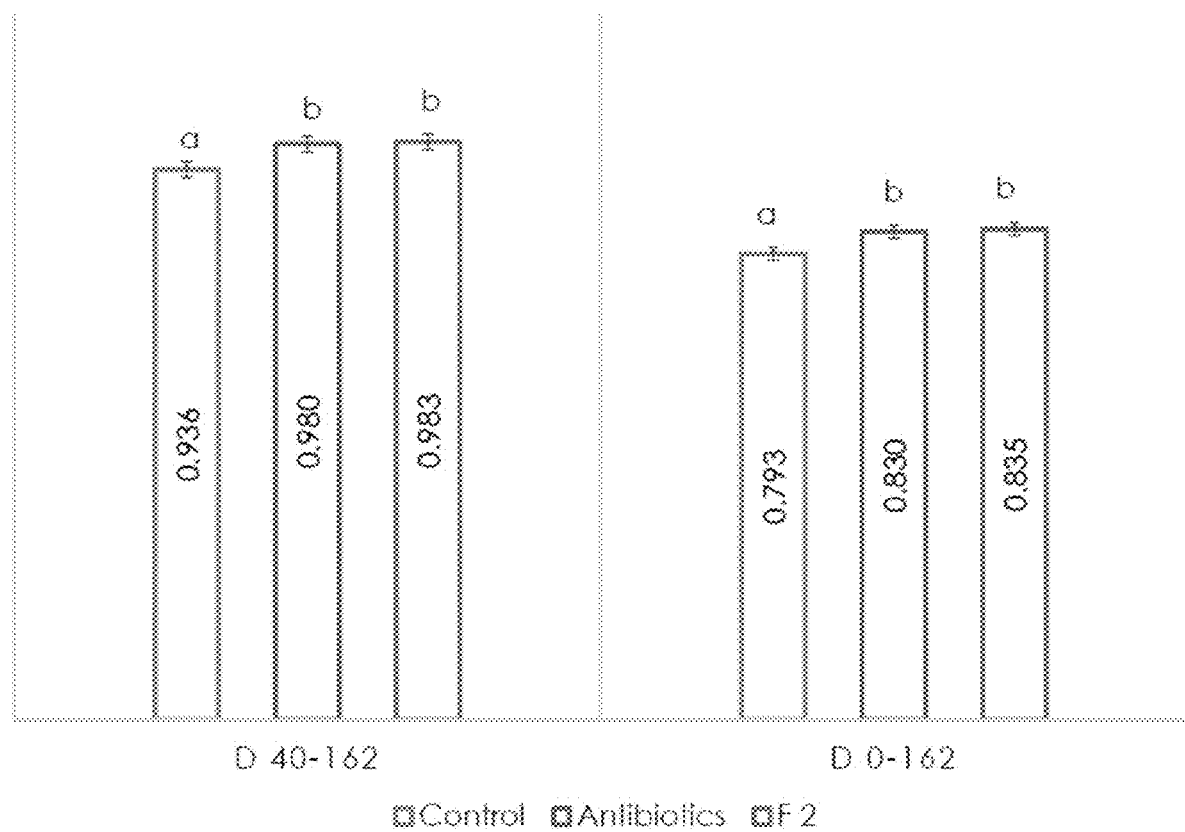
FIG. 25 shows the effect of F2 supplementation and antibiotics on average daily gain (ADG) in wean to market pigs in the third animal trial (i.e. validation trial of F2_Str3). Pigs that were assigned to the F2 treatment group were drenched with F2 on weaning day (d 0), on d 1, and again at the end of nursery phase 2 (d 28). For the antibiotic treatment group, Carbadox (Mecadox® 10, Phibro Animal Health Corporation, Teaneck, NJ), and tiamulin hydrogen fumarate (Denagard®) plus chlortetracycline hydrochloride (CTC®, Novartis Animal Health US Inc, Greensboro, NC) were added in phase 1 and 2, respectively. a.b. The LSmeans without a common superscript differ significantly at p≤0.05.

Pigs fed antibiotics showed an increased average daily gain (ADG) over pigs fed a control diet, while pigs that received the F2 drench on d 0 and d 1 showed an intermediate ADG (p=0.0528) from d 0 to d 7 (Table 14). From d7 onward, F2-treated pigs showed an increase in ADG that was similar to that observed in antibiotic-treated pigs at nursery phase 2 (d 14-28, p=0.0237), grower phase 1 (d77-104, p=0.0134), overall grower-finisher (d 40-162, p=0.047, FIG. 25) and during the entire trial (d 0-162, p=0.033, FIG. 25). A significant reduction in ADG in finisher phase 2 was observed in F2-treated pigs (d 126-134, p=0.0082). This is likely due to the administration of Tylan water medication due to an ileitis outbreak. Compensatory weight gain was observed in the F2-treated pigs in following phase, which led to superior weight gain as compared to the control pigs and antibiotic-treated pigs in finisher phase 3 (p=0.028).

TABLE 14

Effect of F2 and feed additive antibiotics on average daily gain (ADG) in wean to market pigs (LS means)

| | Control | Antibiotics | F2 | SEM | P - Value Trt |
|---|---|---|---|---|---|
| ADG, kg/d | | | | | |
| Nursery | | | | | |
| d 0-7 | 0.002$^a$ | 0.033$^b$ | 0.014$^{ab}$ | 0.008 | 0.0528 |
| d 7-14 | 0.069 | 0.047 | 0.086 | 0.015 | 0.2045 |
| d 0-14 | 0.036 | 0.040 | 0.050 | 0.010 | 0.5769 |
| d 14-28 | 0.430$^a$ | 0.488$^b$ | 0.484$^b$ | 0.015 | 0.0237 |
| d 28-40 | 0.636 | 0.630 | 0.645 | 0.013 | 0.7404 |
| d 0-40 | 0.356 | 0.375 | 0.382 | 0.010 | 0.188 |
| Grower/finisher | | | | | |
| d 40-77 | 0.605 | 0.659 | 0.650 | 0.021 | 0.1728 |
| d 77-104 | 0.795$^a$ | 0.968$^b$ | 0.921$^b$ | 0.036 | 0.0134 |
| d 104-126 | 1.287 | 1.271 | 1.342 | 0.042 | 0.4705 |
| d 126-134 | 1.798$^b$ | 1.768$^b$ | 1.354$^a$ | 0.094 | 0.0082 |
| d 134-162 | 0.987$^a$ | 0.961$^a$ | 1.097$^b$ | 0.033 | 0.028 |
| d 40-162 | 0.936$^a$ | 0.980$^b$ | 0.983$^b$ | 0.013 | 0.047 |
| d 0-162 | 0.793$^a$ | 0.830$^b$ | 0.835$^b$ | 0.011 | 0.033 |

$^{a,b}$The LSmeans without a common superscript differ significantly at p ≤ 0.05.
x.y. The LSmeans without a common superscript tend to be different at 0.05 < p ≤ 0.1.

Body weight (BW) was not different among the treatment groups during the nursery stage (Table 15). The improvement in ADG in the antibiotic-treated and F2-treated pigs resulted in heavier BW at the end of G2 (p=0.0128) and F1 (p=0.0505). The antibiotic-treated and F2-treated pigs were 5.77 kg and 6.37 kg heavier than the pigs fed control diets at study completion (FIG. 26, p=0.0575), respectively.

TABLE 15

Effect of F2 and feed additive antibiotics on body weight (BW) in wean to market pigs (LS means)

| | Control | Antibiotics | F2 | SEM | P - Value Trt |
|---|---|---|---|---|---|
| BW, kg | | | | | |
| Nursery | | | | | |
| Wean (d 0) | 6.21 | 6.20 | 6.16 | 0.03 | 0.351 |
| d 7 | 6.23 | 6.43 | 6.25 | 0.07 | 0.0881 |
| end of phase 1 (d 14) | 6.71 | 6.75 | 6.86 | 0.15 | 0.7808 |
| end of phase 2 (d 28) | 12.33 | 13.08 | 13.17 | 0.29 | 0.1171 |
| end of nursery (d 40) | 19.97 | 20.65 | 20.90 | 0.39 | 0.251 |
| Grower/finisher | | | | | |
| end of G 1 (d 77) | 42.63 | 45.24 | 44.74 | 0.94 | 0.1534 |
| end of G 2 (d 104) | 64.11$^a$ | 71.36$^b$ | 69.60$^b$ | 1.54 | 0.0128 |
| end of F 1 (d 126) | 92.95$^a$ | 99.68$^b$ | 99.79$^b$ | 2.03 | 0.0505 |
| end of F 2 (d 134) | 107.33$^a$ | 113.82$^b$ | 110.62$^{ab}$ | 1.68 | 0.0501 |
| end of F 3 (d 162) | 134.97$^x$ | 140.74$^y$ | 141.34$^y$ | 1.87 | 0.0575 |

$^{a,b}$The LSmeans without a common superscript differ significantly at p ≤ 0.05.
$^{x,y}$The LSmeans without a common superscript tend to be different at 0.05 < p ≤ 0.1.

Unlike ADG and BW, average daily feed intake was never significantly different between the treatments during the entire trial (Table 16). However, the treatments had a significant effect on feed efficiency (presented as gain to feed ratio, G:F) on d 126-134 and on d 134-162 (Table 17). Pigs fed control diets and antibiotic-fed pigs had a higher G:F than pigs fed F2 on d 126-134 (p=0.0058), while a greater G:F was observed in pigs fed antibiotics or F2 as compared to pigs fed control diets on d 134-162 (p=0.0091). The inconsistent effect on G:F in the F2-treated pigs is associated with the weight gain responses after water medication, noted above.

TABLE 16

Effect of F2 and feed additive antibiotics on average daily intake (ADFI) in wean to market pigs (LS means)

| | Control | Antibiotics | F2 | SEM | P - Value Trt |
|---|---|---|---|---|---|
| ADFI, kg/d | | | | | |
| Nursery | | | | | |
| d 0-7 | 0.104 | 0.111 | 0.103 | 0.007 | 0.7346 |
| d 7-14 | 0.172 | 0.172 | 0.167 | 0.013 | 0.9567 |
| d 0-14 | 0.138 | 0.141 | 0.135 | 0.009 | 0.8919 |
| d 14-28 | 0.520 | 0.579 | 0.565 | 0.021 | 0.1686 |
| d 28-40 | 0.963 | 1.000 | 0.994 | 0.024 | 0.527 |
| d 0-40 | 0.488 | 0.521 | 0.518 | 0.015 | 0.2424 |
| Grower/finisher | | | | | |
| d 40-77 | 1.308 | 1.478 | 1.364 | 0.080 | 0.3343 |
| d 77-104 | 2.165 | 2.373 | 2.262 | 0.069 | 0.1416 |
| d 104-126 | 2.985 | 3.041 | 3.140 | 0.108 | 0.6002 |
| d 126-134 | 3.807 | 3.831 | 3.683 | 0.154 | 0.77 |
| d 134-162 | 3.687 | 3.625 | 3.695 | 0.074 | 0.7701 |
| d 40-162 | 2.510 | 2.605 | 2.570 | 0.046 | 0.3549 |
| d 0-162 | 2.011 | 2.091 | 2.063 | 0.035 | 0.2888 |

TABLE 17

Effect of F2 and feed additive antibiotics on feed efficiency (gain to feed ratio, G:F) in wean to market pigs (LS means)

| | Control | Antibiotics | F2 | SEM | P - Value Trt |
|---|---|---|---|---|---|
| G:F | | | | | |
| Nursery | | | | | |
| d 0-7 | 0.000 | 0.235 | 0.101 | 0.085 | 0.1799 |
| d 7-14 | 0.074 | 0.038 | 0.083 | 0.014 | 0.0724 |
| d 0-14 | 0.037 | 0.136 | 0.092 | 0.045 | 0.3232 |
| d 14-28 | 0.826 | 0.849 | 0.858 | 0.016 | 0.3868 |
| d 28-40 | 0.661 | 0.636 | 0.654 | 0.016 | 0.5431 |
| d 0-40 | 0.454 | 0.485 | 0.486 | 0.018 | 0.3619 |
| Grower/finisher | | | | | |
| d 40-77 | 0.469 | 0.463 | 0.479 | 0.024 | 0.8888 |
| d 77-104 | 0.370 | 0.414 | 0.411 | 0.014 | 0.0891 |
| d 104-126 | 0.432 | 0.419 | 0.430 | 0.014 | 0.7747 |
| d 126-134 | 0.473$^b$ | 0.463$^b$ | 0.364$^a$ | 0.022 | 0.0058 |
| d 134-162 | 0.269$^a$ | 0.265$^a$ | 0.298$^b$ | 0.007 | 0.0091 |
| d 40-162 | 0.395 | 0.399 | 0.406 | 0.009 | 0.6959 |
| d 0-162 | 0.409 | 0.420 | 0.426 | 0.009 | 0.4501 |

$^{a,b}$The LSmeans without a common superscript differ significantly at p ≤ 0.05.
x.y. The LSmeans without a common superscript tend to be different at 0.05 < p ≤ 0.1.

Carcass characteristics results are presented in Table 18. Due to low replicates per treatment (n=8), there were no differences observed in carcass characteristics among treatments, with the exception of belly dorsal thickness, which was thicker in F2-treated pigs as compared to control fed pigs with antibiotic-treated pigs as the intermediate (p=0.035). The pigs selected for carcass quality determination had displayed a similar growth rate and final body weight as their original pen mates. Antibiotic-treated and F2-treated pigs had body weights that were 4.7 kg and 5.7 kg heavier and hot carcass weights that were 4 kg and 3 kg heavier as compared to control pigs (p=0.394 and 0.466, respectively). 10

TABLE 18

Effect of F2 and feed additive antibiotics on carcass characteristics (LS means)

| | Control | Antibiotics | F2 | SEM | P - value Trt |
|---|---|---|---|---|---|
| Carcass characteristics | | | | | |
| Live BW, kg | 144.1 | 148.8 | 149.8 | 3.1 | 0.3935 |
| HCW, kg | 104.0 | 108.0 | 107.0 | 2.8 | 0.4663 |
| Yield, % | 72.4 | 72.7 | 71.5 | 0.7 | 0.1183 |
| 10th rib backfat thickness, cm | 2.25 | 2.38 | 2.67 | 0.18 | 0.2642 |
| Longissimus muscle area, cm$^2$ | 49.02 | 51.12 | 47.89 | 1.47 | 0.3187 |
| NPB color Loin | 2.63 | 2.19 | 2.25 | 0.18 | 0.2249 |
| L* | 62.48 | 64.78 | 63.43 | 1.04 | 0.3237 |
| a* | 14.89 | 15.22 | 15.36 | 0.42 | 0.7274 |
| b* | 14.03 | 14.83 | 14.89 | 0.52 | 0.4457 |
| Chroma | 20.47 | 21.27 | 21.41 | 0.65 | 0.5572 |
| Hue Angle, % | 43.28 | 44.06 | 44.12 | 0.48 | 0.4051 |
| Belly, cm | | | | | |
| Length | 77.31 | 73.85 | 74.23 | 2.33 | 0.5249 |
| Width | 24.73 | 25.34 | 25.18 | 0.49 | 0.6077 |
| Dorsal thickness | 3.34$^a$ | 3.68$^{ab}$ | 4.02$^b$ | 0.18 | 0.0347 |
| Ventral thickness | 3.74 | 3.61 | 3.37 | 0.17 | 0.3033 |
| Posterior thickness | 5.17 | 4.97 | 5.46 | 0.27 | 0.4552 |
| Anterior thickness | 4.92 | 5.45 | 4.79 | 0.25 | 0.1786 |

NPB color (Scale from 1 to 5, light = 1, dark = 5)
$^{a,b}$The LSmeans without a common superscript differ significantly at p ≤ 0.05.

To summarize, treatment with F2 at weaning conferred a similar increase in growth rate over control pigs as compared to treatment with antibiotics. Similar to antibiotic treatment, F2 treatment has little or no effect on feed efficiency. In addition, F2 pigs exhibited similar carcass characteristics as control and antibiotic-treated pigs. These results provide strong evidence that F2-supplementation can be used as an antibiotic replacement without having a detrimental impact on pork quality.

Future Studies:

In ongoing work, metagenomics and metabolomics, coupled with 16S rRNA sequencing, will be used to determine how supplementation with F2 during the nursey period alters the piglet gut microbiome through the pre-harvest period. Specifically, we will assess the diversity, membership, structure, composition, stability, and function of the microbiome, as well metabolites found in pig feces and blood, and potential interactions of F2 with other bacterial taxa, including both beneficial bacteria and pathogens. DNA will be extracted from feces by using the PowerSoil kit (Qiagen) and the concentration will be normalized to 10 ng/μl. The microbiome will be characterized by using next-generation sequencing (Illumina Miseq). Sequences will be analyzed by using the QIIME2 software package. Beneficial bacterial OTUs will be identified by using Random Forest, a machine learning approach. DNA extracted from feces will also be analyzed with metagenome tools for species level resolution and functional annotation. Plasma samples and fecal samples will also be subjected to metabolomics analysis.

REFERENCES

Balasubramanian, B., Li, T., & Kim, I. H. (2016). Effects of supplementing growing-finishing pig diets with *Bacillus* spp. probiotic on growth performance and meat-carcass grade qualitytraits. *Revista Brasileira de Zootecnia*, 45, 93-100.

Burnett, G. S., & Neil, E. L. (2010). A note on the effect of Probioticum feed additive on the live-weight gain, feed conversion and carcass quality of bacon pigs. *Animal Science*, 25 (1), 95-98. doi: 10.1017/S0003356100039088

Liu, Y., Espinosa, C. D., Abelilla, J. J., Casas, G. A., Lagos, L. V., Lee, S. A., . . . Stein, H. H. (2018). Non-antibiotic feed additives in diets for pigs: A review. *Animal Nutrition*, 4 (2), 113-125. doi: https://doi.org/10.1016/j.aninu.2018.01.007

Markowiak, P., & Śliżewska, K. (2018). The role of probiotics, prebiotics and synbiotics in animal nutrition. *Gut Pathogens*, 10 (1), 21. doi: 10.1186/s13099-018-0250-0

Ross, G. R., Van Nieuwenhove, C. P., & González, S. N. (2012). Fatty Acid Profile of Pig Meat after Probiotic Administration. *Journal of Agricultural and Food Chemistry*, 60 (23), 5974-5978. doi: 10.1021/jf205360h Rybarczyk, A., Bogusławska-Wąs, E., & Łupkowska, A. (2020). Effect of EM® probiotic on gut microbiota, growth performance, carcass and meat quality of pigs. *Livestock Science*, 241, 104206. doi: https://doi.org/10.1016/j.livsci.2020.104206

Wang, X., Tsai, T., Deng, F., Wei, X., Chai, J., Knapp, J., . . . Zhao, J. (2019). Longitudinal investigation of the swine gut microbiome from birth to market reveals stage and growth performance associated bacteria. *Microbiome*, 7 (1), 109. doi: 10.1186/s40168-019-0721-7

Deposit Information

A deposit of the University of Arkansas Division of Agriculture proprietary bacterial isolates disclosed above and recited in the appended claims has been made with the American Type Culture Collection (ATCC), 10801 University Boulevard, Manassas, Virginia 20110, and has been accepted under the terms of the Budapest Treaty. Specifically, one *Lactobacillus* (LactX) and two *Streptococcus* (StrepX1 and StrepX3) isolates have been deposited. The date of deposit was Dec. 22, 2022. The deposit comprises 5 liquid nitrogen stocks of each isolate, which were found viable on Jan. 20, 2023. All restrictions will be irrevocably removed upon granting of a patent, and the deposit is intended to meet all of the requirements of 37 C.F.R. §§ 1.801-1.809. The ATCC Accession Numbers are PTA-127487 (LactX), PTA-127485 (StrepX1), and PTA-127486 (StrepX3). The deposit will be maintained in the depository for a period of thirty years, or five years after the last request, or for the enforceable life of the patent, whichever is longer, and will be replaced as necessary during that period.

What is claimed:

1. A composition comprising a dried animal feed and a lyophilized isolated bacterial strain comprising *Lactobacillus* strain LactX, wherein LactX is the bacterium deposited at the American Type Culture Collection (ATCC) under accession number PTA-127487, and wherein the composition contains at least $10^8$ colony forming units of LactX per serving.

2. The composition of claim 1 wherein the lyophilized isolated bacterial strain further comprises *Streptococcus* strain StrepX3 or StrepX1, wherein StrepX3 and StrepX1 have the 16S rRNA sequence of SEQ ID NO:2.

3. The composition of claim 2, wherein StrepX1 is the bacterium deposited at the ATCC under accession number PTA-127485, and StrepX3 is the bacterium deposited at the ATCC under accession number PTA-127486.

4. The composition of claim 1, wherein the composition is a direct-fed microbial composition.

\* \* \* \* \*